US009926527B2

(12) United States Patent
Harding et al.

(10) Patent No.: US 9,926,527 B2
(45) **Date of Patent: *Mar. 27, 2018**

(54) MODIFIED ORGANISMS FOR PRODUCING GUMS

(71) Applicant: CP Kelco U.S., Inc., Atlanta, GA (US)

(72) Inventors: Nancy E. Harding, San Diego, CA (US); Yamini N. Patel, San Diego, CA (US); Russell Coleman, San Diego, CA (US); Steven Matzke, San Diego, CA (US)

(73) Assignee: CP Kelco U.S., Inc., Atlanta, GA (US)

(*) Notice: Subject to any disclaimer, the term of this patent is extended or adjusted under 35 U.S.C. 154(b) by 68 days.

This patent is subject to a terminal disclaimer.

(21) Appl. No.: 14/585,094

(22) Filed: Dec. 29, 2014

(65) Prior Publication Data

US 2015/0125932 A1 May 7, 2015

Related U.S. Application Data

(60) Division of application No. 13/599,202, filed on Aug. 30, 2012, now Pat. No. 8,921,077, which is a division (Continued)

(51) Int. Cl.

*C12N 1/20* (2006.01)
*C12P 19/04* (2006.01)

(Continued)

(52) U.S. Cl.

CPC .............. *C12N 1/20* (2013.01); *A61K 9/4816* (2013.01); *A61K 9/7007* (2013.01); *A61K 47/38* (2013.01);

(Continued)

(58) Field of Classification Search

None

See application file for complete search history.

(56) References Cited

U.S. PATENT DOCUMENTS 3,915,800 A 10/1975 Kang et al.
5,175,278 A 12/1992 Peik et al.

(Continued)

FOREIGN PATENT DOCUMENTS

EP 1586652 A1 10/2005
WO 0129196 A2 4/2001
WO 2006096269 A2 9/2006

OTHER PUBLICATIONS

Uniprot Accession No. P74819_9SPHN, published Feb. 1, 1997.*

(Continued)

*Primary Examiner* — Richard C Ekstrom

(74) *Attorney, Agent, or Firm* — Eversheds Sutherland (US) LLP

(57) ABSTRACT

The production of a diutan polysaccharide exhibiting increased viscosity properties as compared with previously produced polysaccharide of the same type of repeating units. Such an improved diutan polysaccharide is produced through the generation of a derivative of *Sphingomonas* sp. ATCC 53159 that harbors a multicopy broad host-range plasmid into which genes for biosynthesis of diutan polysaccharide have been cloned. The inventive methods of production of such an improved diutan polysaccharide, as well as the novel cloned genes required to produce the improved diutan within such a method, are also encompassed within this invention. Additionally, the novel engineered *Sphingomonas* strain including the needed DNA sequence is encompassed within this invention.

1 Claim, 2 Drawing Sheets

*Sphingomonas sp.* ATCC 53159 dpsS dpsG dpsR dpsQ dpsI dpsK dpsL dpsJ dpsF dpsD dpsC dpsE dpsM dpsN atrD atrB dpsB rmlA rmlC rmlB rmlD orf7 orf6 orf5

Secretion Polymerase Lyase TrIV TrIII TrII ——Polysaccharide secretion—— Protein secretion TrI dTDP-rhamnose synthesis Unknown Unknown functions 0 5000 bp 10000 bp 15000 bp 20000 bp 25000 bp pX6 pS8 pS6 pX4

Related U.S. Application Data of application No. 12/892,561, filed on Sep. 28, 2010, now Pat. No. 8,278,438, which is a continuation of application No. 11/264,268, filed on Nov. 1, 2005, now Pat. No. 7,868,167.

(51) Int. Cl.

| | |
|---|---|
| ***C12P 19/06*** | (2006.01) |
| ***A61K 9/48*** | (2006.01) |
| ***A61K 9/70*** | (2006.01) |
| ***A61K 47/38*** | (2006.01) |
| ***C08B 37/00*** | (2006.01) |
| ***C08B 11/12*** | (2006.01) |
| ***C08L 1/28*** | (2006.01) |
| ***C12N 9/10*** | (2006.01) |

(52) U.S. Cl.

CPC .......... *C08B 11/12* (2013.01); *C08B 37/0033* (2013.01); *C08L 1/286* (2013.01); *C12N 9/10* (2013.01); *C12P 19/04* (2013.01); *C12P 19/06* (2013.01)

(56) References Cited

U.S. PATENT DOCUMENTS

| | | | | |
|---|---|---|---|---|
| 5,854,034 | A | 12/1998 | Pollock et al. | |
| 5,985,623 | A | 11/1999 | Pollock et al. | |
| 6,103,671 | A | 8/2000 | Dobson et al. | |
| 6,110,271 | A | 8/2000 | Skaggs et al. | |
| 6,696,561 | B1 | 2/2004 | Pompejus et al. | |
| 6,709,845 | B1 | 3/2004 | Pollock et al. | |
| 8,921,077 | B2 * | 12/2014 | Harding ............... | A61K 9/4816 435/101 |
| 2003/0140818 | A1 | 7/2003 | Pollock et al. | |
| 2004/0259839 | A1 | 12/2004 | Patel et al. | |
| 2006/0019354 | A1 * | 1/2006 | Yamazaki ............... | C12P 19/06 435/101 |

OTHER PUBLICATIONS

Coleman, “Identification and Organization of Genes for Diutan Polysaccharide Synthesis from *Sphingomonas* sp. ATCC 53159,” Journal of the Society for Industrial Microbiology, 2008, http://www.springerlink.com/content/r4329643v8423164/fulltext.html.

Yamazaki et al., “Linkage of Genes Essential for Synthesis of a Polysaccharide Capsule in Sphingomonas Strain S88,” American Society for Microbiology, 1996, pp. 2676-2687, vol. 178, No. 9.

Coleman., “Cloning and Analysis of *Sphingomonas* SP. ATCC 53159,” Polysaccharide Genes, Thesis, all pages, (Summer 2001).

Korean Office Action for Korean Application No. 10-2008-7013201 dated May 21, 2013 (English) (5 pages).

European Search Report for EP Application No. 11 185 331.3 dated May 31, 2013 (4 pages).

Thorne et al., “Increasing the Yield and Viscosity of Exopolysaccharides Secreted by Sphingomonas by Augmentation of Chromosomal Genes with Multiple Copies of Cloned Biosynthetic Genes,” Journal of Industrial Microbiology and Biotechnology, vol. 25, pp. 49-57, 2000.

* cited by examiner

MODIFIED ORGANISMS FOR PRODUCING GUMS

CROSS REFERENCE TO RELATED APPLICATIONS

This application is a divisional application of U.S. patent application Ser. No. 13/599,202, filed Aug. 30, 2012, which is a divisional application of U.S. patent application Ser. No. 12/892,561, filed Sep. 28, 2010, now U.S. Pat. No. 8,278,438, which is a continuation of U.S. patent application Ser. No. 11/264,268, filed Nov. 1, 2005, now U.S. Pat. No. 7,868,167. The contents of these applications are hereby incorporated by reference.

FIELD OF THE INVENTION

The present invention describes the production of a diutan polysaccharide exhibiting increased viscosity properties as compared with previously produced polysaccharide of the same type of repeating units. Such an improved diutan polysaccharide is produced through the generation of a derivative of *Sphingomonas* sp. ATCC 53159 that harbors a multicopy broad-host-range plasmid into which genes for biosynthesis of diutan polysaccharide have been cloned. The plasmid provides the capability within the host *Sphingomonas* strain to produce multiple copies of genes for such polysaccharide synthesis. In such a manner, a method of not just increased production of the target diutan polysaccharide, but also production of a diutan polysaccharide of improved physical properties (of the aforementioned higher viscosity) thereof is provided. Such a diutan polysaccharide has proven particularly useful as a possible viscosifier in oilfield applications and within cement materials. The inventive methods of production of such an improved diutan polysaccharide, as well as the novel cloned genes required to produce the improved diutan within such a method, are also encompassed within this invention. Additionally, the novel engineered *Sphingomonas* strain including the needed DNA sequence is encompassed within this invention.

BACKGROUND OF THE INVENTION

Polysaccharides or gums are primarily used to thicken or gel aqueous solutions and are frequently classified into two groups: thickeners and gelling agents. Typical thickeners include starches, xanthan gum, diutan gum, welan gum, guar gum, carboxymethylcellulose, alginate, methylcellulose, gum karaya and gum tragacanth. Common gelling agents include gelatin, gellan gum, starch, alginate, pectin, carrageenan, agar and methylcellulose.

Some polysaccharides, or more particularly stated, biogums, such as xanthan, gellan, welan and diutan have been produced via fermentation from microbes for many years. Such biogums exhibit varied characteristics such as viscosity modification capabilities that have permitted their utilization in many different applications. Included within such a list are gelling agents for foods, such as confectionery jellies, jams and jellies, dessert gels, icings and dairy products, as well as components of microbiological media. Furthermore, thickening agents are utilized for myriad end-use applications to modify the viscosity of target liquids. Of particular interest is the ability of such gums to impart viscosity modification to underground and/or underwater petroleum liquids to facilitate collection thereof, although many other different possible end-uses exist (including cement production, as one example). Different biogums have been produced from different bacterial sources, such as xanthan gum, from *Xanthomonas campestris*, gellan gum, from *Sphingomonas elodea*, welan gum from *Sphingomonas* sp. ATCC 31555, and diutan gum (S-657), from *Sphingomonas* sp. ATCC 53159. Genetic modifications of such strains have been undertaken in the past to effectuate significant changes in the resultant gum materials produced through the aforementioned fermentation procedures. Such modifications have permitted such changes as removal of acyl groups to create different gum materials exhibiting different physical properties. Generally, such genetic modifications have been of the type to either alter the composition of the target biogum ultimately through altered gene expression within the host organism, or increase the yield of the target biogum, through introduction of a plasmid that exhibits gene amplification alone (such as in U.S. Pat. Nos. 5,854,034, 5,985,623, and 6,284,516, to Pollock et al. and U.S. Pat. No. 6,709,845 to Pollock alone).

Diutan gum (also known as heteropolysaccharide S-657) is prepared by fermentation of strain *Sphingomonas* sp. ATCC 53159 and exhibits thickening, suspending, and stabilizing properties in aqueous solutions. Diutan generally exhibits a hexameric repeat unit consisting of four sugars in the backbone (glucose-glucuronic acid-glucose-rhamnose) and a side chain of two rhamnose residues attached to one of the glucose residues. Details of the diutan gum structure may be found in an article by Chowdhury, T. A., B. Lindberg, U. Lindquist and J. Baird, Carbohydrate Research 164 (1987) 117-122. Diutan was shown to have two acetyl substituents per repeat unit within Diltz et al., Carbohydrate Research 331 (2001) 265-270. Both of these references are hereby incorporated by reference in their entirety. Details of preparing diutan gum may be found in U.S. Pat. No. 5,175,278, which is hereby incorporated by reference in its entirety. Diutan may be produced from the *Sphingomonas* strain by utilizing standard fermentation techniques such as using carbohydrate sources (glucose, maltose, and the like, as non-limiting examples), a nitrogen source, and additional salts.

The physical characteristics imparted by such a diutan biogum in its wild-type form are desired by certain industries, particularly in terms of its viscosity modification properties and/or water retention characteristics. Unfortunately, diutan has proven difficult to produce cost effectively. Furthermore, such cost issues militate against widespread utilization of diutan currently since the degree of viscosity exhibited by such a biogum is insufficient to supplant other less expensive, but effective, biogums (such as xanthan gum, as one example). As such, it has been an established need to provide a method to produce such an effective diutan at lower cost, at the very least, and/or to provide a manner of producing a biogum of the diutan type that exhibits a significant improvement in physical properties as well. To date, the only mention of production of any types of related sphingans (without any demonstrations for diutan specifically) is in terms of higher yield (within the Pollock et al. patents mentioned above). There has been no discussion or fair suggestion of any manner of providing a method for producing an improved diutan gum of higher molecular weight that exhibits any improvement in viscosity measurements via such a production method.

BRIEF DESCRIPTION OF THE INVENTION

It has now been realized that amplification of certain novel isolated DNA sequences for diutan biosynthesis within a host *Sphingomonas* organism not only permits increased production of diutan gum therefrom, but also produces a diutan gum that exhibits increased viscosity properties. Such a novel DNA sequence (that is introduced within a host organism via any well-known method, such as, without limitation, a plasmid) thus provides the desired results that have been sought after for diutan synthesis methods. A distinct advantage of such utilization of these genes amplified on a plasmid is the relatively simple nature of incorporating such an isolated DNA sequence into diutan synthesis procedures. Another advantage is the ability to produce such higher viscosity properties for the target diutan gum, while potentially increasing the fermentation production efficiency, if necessary.

Accordingly, this invention includes a diutan gum exhibiting an improvement in a number of different viscosity measurements. Among these are: i) an intrinsic viscosity of greater than 150, preferably higher than 155, more preferably higher than 160 dL/g; ii) a sea water 3 rpm viscosity greater than 35, preferably higher than 37, more preferably higher than 40, and most preferably higher than 42 dial reading; iii) a sea water 0.3 rpm viscosity greater than 35,000, preferably higher than 39,000, more preferably higher than 40,000, and most preferably higher than 41,000 centipoise (cP); and a PEG low shear rate viscosity greater than 3500, preferably higher than 3700, more preferably higher than 3900, and most preferably higher than 4000 cP. Also, this invention encompasses a method of producing such a diutan gum, as defined in any of those terms above, through the introduction of a specific cluster of genes into a host *Sphingomonas* organism and permitting fermentation of said organism to produce a resultant diutan gum.

Furthermore, this invention encompasses the specific DNA sequences and any vector (such as a plasmid) to provide multiple copies of the genes or increased expression of the genes by use of a stronger promoter, and the like. Additionally, the genetically modified strain of *Sphingomonas* containing multiple copies of the diutan biosynthetic genes defined by such unique isolated DNA sequences is also encompassed.

Such a unique isolated DNA sequence has been found to require at least one diutan biosynthetic enzyme being a DpsG polymerase. In another possible embodiment, such a diutan biosynthetic enzyme will include a DpsG polymerase and a glucose-1-phosphate thymidylyltransferase; a dTDP-6-deoxy-D-glucose-3-5-epimerase: a dTDP-D-glucose-4,6-dehydratase; and a dTDP-6-deoxy-L-mannose-dehydrogenase. In yet another possible embodiment such a diutan biosynthetic enzyme will include a dpsG polymerase and a rhamnosyl transferase IV; a beta-1,4-glucuronosyl transferase II; a glucosyl isoprenylphosphate transferase I; and a glucosyl transferase III. In still another possible embodiment, such a diutan biosynthetic enzyme comprises a dpsG polymerase and polysaccharide export proteins dpsD, dpsC, and dpsE. In yet another possible embodiment, such a diutan biosynthetic enzyme will include a rhamnosyl transferase IV; a beta-1,4-glucuronosyl transferase II; a glucosyl isoprenylphosphate transferase I; glucosyl transferase III; a glucose-1-phosphate thymidylyltransferase; a dTDP-6-deoxy-D-glucose-3-5-epimerase; a dTDP-D-glucose-4,6-dehydratase; and a dTDP-6-deoxy-L-mannose-dehydrogenase. Generally, the diutan biosynthetic enzyme of the inventive method and within the inventive product may be selected from the group consisting of polymerase; lyase; rhamnosyl transferase IV; beta-1,4-glucuronosyl transferase II; glucosyl transferase III; polysaccharide export protein; secretion protein; glucosyl-isoprenylphosphate transferase I; glucose-1-phosphate thymidylyltransferase; dTDP-6-deoxy-D-glucose-3-5-epimerase; dTDP-D-glucose-4,6-dehydratase; dTDP-6-deoxy-L-mannose-dehydrogenase and combinations thereof. Further encompassed within this invention then is an isolated nucleic acid molecule (in addition to DNA which may be present on the target chromosome) which encodes at least one diutan biosynthetic enzyme as shown in SEQ ID NO: 5, 7, 9, 11, 13, 15, 17, 19, 21, 23, 25, 27, 29, 31, 33, 35, 37, 39, 41, and 43, or an enzyme which is at least 95% identical to SEQ ID NO: 5, 7, 9, 11, 13, 15, 17, 19, 21, 23, 25, 27, 29, 31, 33, 35, 37, 39, 41, and 43.

The inventive method (as well as the products made thereby) thus concern sphingan gums, particularly diutan types, including, without limitation, S88, S60, and S657.

As noted above, the present invention is the culmination of development and realization that specific DNA sequences that are introduced in multiple copies within certain *Sphingomonas* strains can provide increased biosynthetic production of high viscosity diutan polysaccharide. The engineered bacteria containing such genes for increased production produce significantly greater amounts of diutan polysaccharide compared to non-engineered bacteria and create the aforementioned resultant high viscosity properties.

The DNA sequences that are introduced within the host organism (in any well-known form, such as, again, as one non-limiting example, a plasmid) to generate the aforementioned increased production and increased viscosity properties (through what is believed, without any reliance upon any specific scientific theory, an increase in molecular weight range properties) according to the present invention may be isolated, recovered and cloned by techniques that are readily available in the art. Thereafter, the DNA is delivered into bacteria of the genus *Sphingomonas* in multiple copies (via plasmid, other known manner) or increased expression of the genes via a suitable, e.g., stronger promoter. After insertion into the target bacteria, the production of diutan can be determined by fermenting the engineered bacteria and comparing the yield in terms of amount produced and quality produced. Increased production and viscosity increases can both be determined by comparing diutan production via the inventive method in comparison with the wild type diutan-producing strain (ATCC 53159).

DETAILED DESCRIPTION OF THE INVENTION

Figure 1:
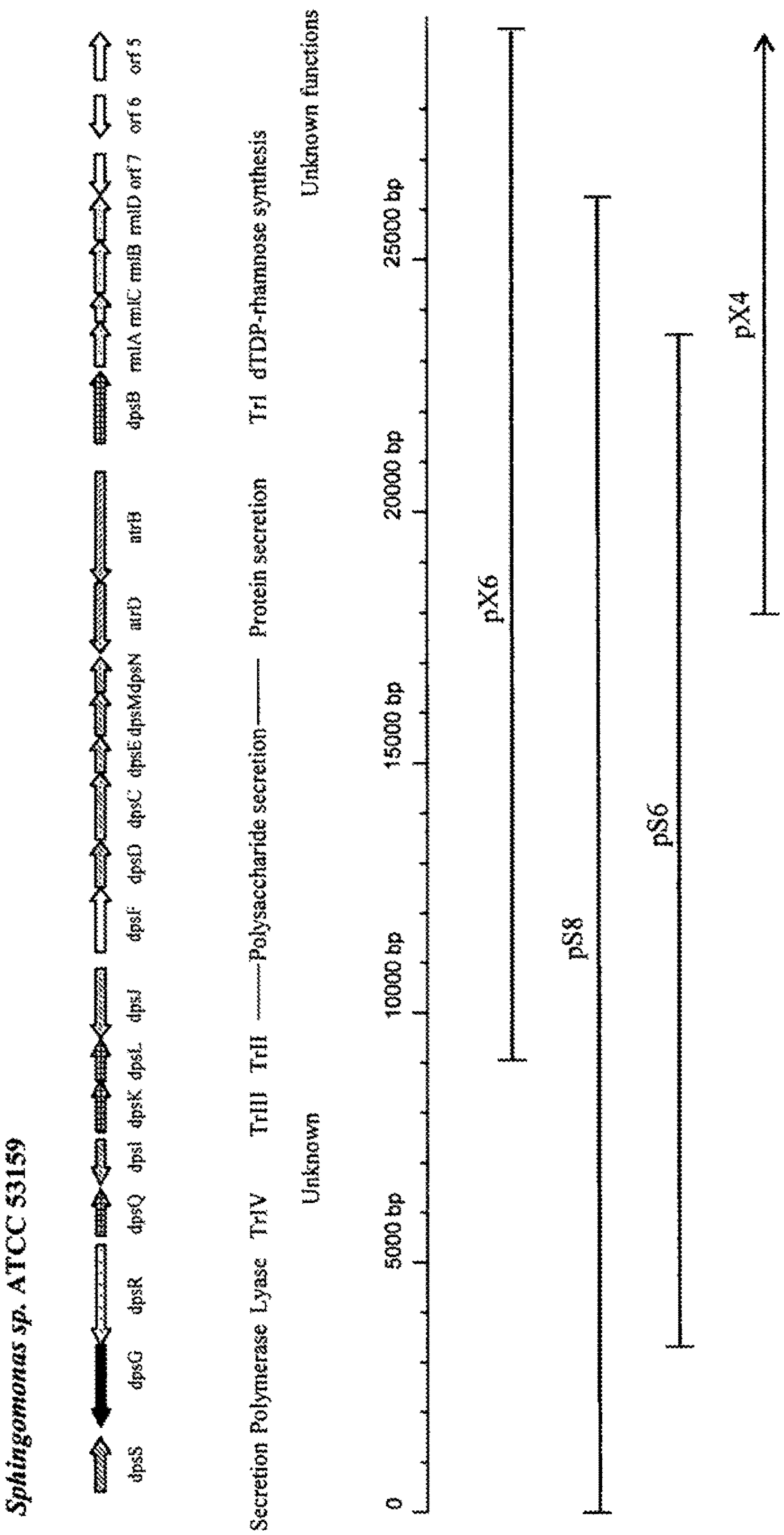
FIG. 1 is a diagrammatic representation of the isolated genes for diutan gum biosynthesis. Putative or known genes are indicated. The segments inserted into different plasmids are also indicated.

The following terms shall be used throughout the specification in connection with the present invention and have the meaning indicated:

The term "*Sphingomonas*" is used throughout the specification to refer to strains of gram-negative bacteria from the genus *Sphingomonas.*

The term "increased producer" or "increased production" is used throughout the specification to describe engineered bacteria containing multiple copies of DNA sequences isolated from the same strain which produce significantly greater (at least about 5% more on a weight by weight basis) diutan polysaccharide compared to wild-type bacteria of the same strain.

The term "isolated" is used to describe DNA which has been removed from a microorganism and subjected to at least some degree of purification, i.e., one or more purification steps, and which can be cleaved or cut by restriction enzymes, cloned into multiple copies or inserted into plasmid vectors or otherwise inserted or incorporated into bacteria.

The term "sequence" is used to describe a specific segment of DNA which is identified by its nucleotide units. The term "inserted" is used throughout the specification to describe the process and outcome of transferring DNA segments isolated from the chromosomal DNA of a diutan-producing *Sphingomonas* strain into the *Sphingomonas* strain (via a plasmid, as one non-limiting example). Such isolated DNA may be introduced first into, again as one non-limiting possibility, the desired plasmid (here pLAFR3), by well-known techniques in the art, and then transferred, for example, by conjugation or mobilization into a recipient *Sphingomonas* bacterium. After insertion into a recipient *Sphingomonas* bacterium, the plasmid containing the relevant DNA sequence will replicate in the recipient cell to give several (at least two and usually 4-10) copies of the DNA segment necessary for increased production of high viscosity (again, believed to be high molecular weight range) diutan polysaccharide. The use of conjugation or mobilization to transfer the plasmid vectors into recipient bacteria is generally effective. Electroporation or chemical transformation of competent cells with purified DNA may also be used. Other vectors or bacteriophages can be used to transfer DNA into the host cell. Maintaining the DNA segments on plasmids (or other well-known delivery vectors) in the recipient diutan-producing *Sphingomonas* is not necessary. It is routine to introduce additional copies of a DNA segment into the bacterial chromosome so that the segments are replicated each generation by the same mechanism that replicates the bacterial DNA. Alternatively, increased expression of the genes may be achieved by using stronger promoter elements.

The term "gene amplification" is used to refer to either increased copies of genes, for example by cloning the target genes on a multicopy plasmid (such as from 4 to 10 copies) or insertion of multiple copies (such as from 4 to 10) of the genes into the bacterial genome, or alternatively increased expression of genes by modification of promoter elements to increase gene expression. Both of these methods and others can result in increased amounts of the encoded proteins.

The term "biosynthesis" is used throughout the specification to describe the biological production or synthesis of diutan by *Sphingomonas* bacteria. Diutan polysaccharide is synthesized from individual carbohydrate units in a series of steps controlled by a large number of enzymes of the bacteria.

The relevant DNA sequence which is incorporated into the recipient bacteria in any selected form (such as, again, preferably, but not necessarily, plasmid form) encodes genetic information which is known to be beneficial or essential for the biosynthesis of increased production and increased molecular weight diutan polysaccharide. Additionally, though, the particular inventive DNA sequence (such as within plasmid pS8) is believed, without relying on a specific scientific theory, to induce, not just increased production, but also an increase in number of repeating units polymerized within the individual polymers of the diutan itself. As a result, it is believed that such an increase in repeating units produces the resultant high viscosity properties surprisingly provided by the diutan gum. A molecular weight increase has been hypothesized due to measured increases in intrinsic viscosity which is related to molecular weight by a power law relationship. For a linear polymer (like diutan gum), intrinsic viscosity is thus known to be essentially proportional to molecular weight in that respect.

The isolation of the relevant DNA sequences that are the basis of this inventive method and that generate the increased viscosity diutan polysaccharide is accomplished via standard techniques and methods. Such sequences may thus be generated from a diutan-producing *Sphingomonas* strain that has been cultured using standard procedures. Extraction of the DNA can then be performed, for example, through initial centrifugation and resuspension of the bacterial cells and then subsequent elution of the DNA through purification columns. After purification is completed, the isolated DNA can be digested with restriction endonucleases and cloned into the desired plasmid or other delivery vector and subsequently transferred to a recipient strain. Other techniques as are known in the art can be used without limitation.

The cloning of DNA in the present invention relies on general techniques and methods which have become standard in the art. It is noted that any number of methods may be used to clone the DNA segments according to the present invention and the present invention is not limited, for example, to the use of plasmid cloning vectors. For example, the DNA fragments may be cloned by insertion into a bacteriophage vector.

The cloned DNA sequences can be then introduced to a *Sphingomonas* strain via a plasmid or other delivery vector. The genetically modified *Sphingomonas* strain can then be used to produce diutan by fermentation. Basically, a suitable medium for fermentation is an aqueous medium which generally contains a source of carbon such as, for example, carbohydrates including glucose, lactose, sucrose, maltose or maltodextrins, a nitrogen source such as, for example, inorganic ammonium, inorganic nitrate, organic amino acids or proteinaceous materials such as hydrolyzed yeast, soy flour or casein, distiller's solubles or corn steep liquor, and inorganic salts. A wide variety of fermentation media will support the production of diutans according to the present invention.

Carbohydrates can be included in the fermentation broth in varying amounts but usually between about 1 and 10% by weight (preferably 2-8%) of the fermentation medium. The carbohydrates may be added prior to fermentation or alternatively, during fermentation. The amount of nitrogen may range from about 0.01% to about 0.4% by weight of the aqueous medium. A single carbon source or nitrogen source may be used, as well as mixtures of these sources. Among the inorganic salts which find use in fermenting *Sphingomonas* bacteria are salts which contain sodium, potassium, ammonium, nitrate, calcium, phosphate, sulfate, chloride, carbonate and similar ions. Trace metals such as magnesium, manganese, cobalt, iron, zinc, copper, molybdenum, iodide and borate may also be advantageously included.

The fermentation can be carried out at temperatures between about 25° and 40° C., with a temperature range of about 27° and 35° C. preferred. The inoculum can be prepared by standard methods of volume scale-up, including shake flask cultures and small-scale submerged stirred fermentation. The medium for preparing the inoculum can be the same as the production medium or can be any one of several standard media well-known in the art, such as Luria broth or YM medium. More than one seed stage may be used to obtain the desired volume for inoculation. Typical inoculation volumes range from about 0.5% to about 10% of the total final fermentation volume.

The fermentation vessel may contain an agitator to stir the contents. The vessel also may have automatic pH and foaming controls. The production medium can be added to the vessel and sterilized in place by heating. Alternatively, the carbohydrate or carbon source may be sterilized separately before addition. A previously grown seed culture can be added to the cooled medium (generally, at the preferred fermentation temperature of about 27° to about 35° C.) and the stirred culture can be fermented for about 48 to about 110 hours, producing a high viscosity broth. The diutan polysaccharide can be recovered from the broth by the standard method of precipitation with an alcohol, generally isopropanol.

Preferred Embodiments of the Invention Including Detailed Descriptions of the Drawings The following examples are provided to illustrate the present invention. The description of the examples should not be misconstrued to limit the scope of the present invention in any way.

DNA Sequence Isolation/Plasmid Production

To undergo the initial isolation and determine the proper sequence for the inventive results described previously, a gene library of the ATCC 53159 organism was constructed as follows: Chromosomal DNA was isolated from *Sphingomonas* sp. ATCC 53159 and partially digested with Sau3AI restriction endonuclease. DNA fragments in the range of 15 to 50 kb were purified from an agarose gel and ligated into BamHI digested cosmid cloning vector pLAFR3 (in accordance with Staskawicz, et al., "Molecular characterization of cloned avirulence genes from race 0 and race 1 of *Pseudomonas syringae. Glycinea*", J. Bacteriology. 1987. 169: 5789-94), isolated from *Escherichia coli* strain JZ279 (from Harding, et al., "Genetic and physical analysis of a cluster of genes essential for xanthan gum biosynthesis in *Xanthomonas campestris*", J. Bacteriology. 1987. 169: 2854-61). Ligation reactions were packaged in λ phage particles (using Gigapack III Gold packaging extract, from Stratagene, La Jolla, Calif.) and transfected into Library Efficiency *E. coli* DH5αMCR cells (Life Technologies, Rockville, Md.). Approximately 10.000 tetracycline resistant colonies were pooled to form the gene library. From this library, individual sequences were then isolated. The work undertaken in this instance involved the isolation of specific genes for polysaccharide biosynthesis from the *Sphingomonas* ATCC 53159 organism.

Such genes for polysaccharide biosynthesis are typically identified by complementation of mutants defective in polysaccharide synthesis, particularly those blocked in the first step, glycosyl transferase I. Since initially no transferase I defective mutants of ATCC 53159 were available, complementation of transferase I defective mutants of *Sphingomonas elodea* and *Xanthomonas campestris* were utilized to identify genes for diutan polysaccharide biosynthesis. Plasmid pLAFR3 can be transferred from its *E. coli* host to other gram-negative bacteria by tri-parental conjugation using a helper plasmid that supplies IncP transfer functions (in accordance with Ditta, et al., "Broad host range DNA cloning system for gram-negative bacteria: construction of a gene bank of *Rhizobium meliloti*", Proc. Natl. Acad. Sci. 1980. 77:7347-51.). RK2 type plasmids have an estimated copy number in *E. coli* of five to seven per chromosome (Figurski et al., "Suppression of ColE 1 replication properties by the Inc P-1 plasmid RK2 in hybrid plasmids constructed in vitro", J. Mol. Biol. 1979 133: 295-318.).

The gene library of ATCC 53159 chromosomal DNA in *E. coli* was transferred into a nonmucoid mutant (GPS2) of *S. elodea* ATCC 31461, by triparental conjugation, selecting for tetracycline and streptomycin resistance. The helper plasmid used was pRK2013 (in *E. coli* strain JZ279), which contains a narrow-host-range origin of replication but exhibits trans acting functions needed to mobilize pLAFR3. Plasmid pRK2013 was not replicated in *Sphingomonas* strains. *S. elodea* ATCC 31461 produces the polysaccharide gellan. Both gellan and diutan polysaccharides have the same tetrasaccharide repeat unit, comprised of [→4)-α-L-rhamnose-(1→3)-β-D-glucose-(1→4)-β-D-glucuronic acid-(1→4)-β-D-glucose(1→]. Diutan, however, also includes a side chain comprised of two rhamnose molecules attached to one of the glucose residues, and is modified by acetyl, whereas gellan has no side chain sugars and is modified with acetyl and glyceryl. The mutant GPS2 is defective in the first step of polysaccharide biosynthesis, i.e., transfer of glucose-1-phosphate from UDP-D-glucose to the bactoprenyl phosphate lipid carrier by glucosyl transferase I-enzyme. From tetracycline selection plates, polysaccharide-producing (mucoid) colonies were isolated from a background of non-mucoid colonies. Clones restoring polysaccharide production presumably contained the ATCC 53159 gene encoding glucosyl transferase I plus approximately 20-25 kb of adjacent DNA. Plasmid DNA was isolated from eight mucoid GPS2 transconjugants and transferred to *E. coli* strain DH5α (Life Technologies) by electroporation. The plasmids were isolated from *E. coli* to obtain sufficient DNA for double-digestion with restriction endonucleases HindIII/EcoRI (which cut either side of the BamHI restriction endonuclease site in the polylinker), to excise the insert DNA from the vector. The sizes of the insert DNA in the clones were determined by gel electrophoresis. The end sequences of several plasmids were determined by sequencing from primers specific to plasmid sequences flanking the BamHI site of the vector. The sequences were analyzed by comparison to sequences in computer databases using BLASTX. Two of these plasmids, pS8 and pS6, are presented in FIG. 1. Similarly, the ATCC 53159 gene library was transferred into a rifampicin-resistant nonmucoid *X. campestris* mutant defective in transferase I (CXC109) (such as in the Harding et al. reference noted above) through triparental conjugation selecting for resistance to tetracycline and rifampicin. *X campestris* produces xanthan polysaccharide, the synthesis of which is also initiated by transfer of glucose-1-phosphate from UDP-D-glucose to the bactoprenyl phosphate lipid carrier by transferase I enzyme (Ielpi et al., "Sequential assembly and polymerization of the polyprenol-linked pentasaccharide repeating unit of the xanthan polysaccharide in *Xanthomonas campestris*", J. Bacteriology. 1993. 175: 2490-500). Plasmids were purified from mucoid transconjugants and the end sequences determined as described above. Two of these plasmids pX6 and pX4 are presented in FIG. 1.

The S657 DNA cloned in plasmids pS8 and pX6 was completely sequenced by double-stranded shotgun sequencing at Lark Technologies Inc., (Houston, Tex.). These sequences were analyzed to identify the genes for diutan biosynthesis (presented in FIG. 1). Gene functions were designated based on homology to other genes in databases, in particular to the published genes for biosynthesis of S-88 sphingan (such as within the aforementioned '516 Pollock et al. patent), GenBank accession number U51197 and gellan (GenBank AY217008 and AY220099). Genes were identified (FIG. 1) that encoded the transferases for the four sugars of the backbone and four genes for dTDP-rhamnose synthesis. Genes for secretion of the polysaccharide were based on homology to genes for biosynthesis of other polysaccharides. Two genes encode proteins homologous to proteins involved in protein secretion. Two genes putatively encode a polymerase and a lyase. The insert in plasmid pX6 contained 17 genes including gene dpsB encoding transferase I (which initiates the first step in diutan synthesis), genes for secretion and four genes for dTDP-rhamnose synthesis, but lacks the genes for transferases II, III and IV and the putative genes for polymerase and lyase Plasmid pS8 contains 20 genes of the dps gene cluster, including genes for all four backbone sugar transferases, the four genes for dTDP-rhamnose synthesis, and genes for secretion of the polysaccharide, including the putative genes for polymerase and lyase, but lacks the genes of unknown function, orf6 and orf7. Plasmid pS6 contains genes for secretion and the four sugar transferases but does not have all genes for dTDP-rhamnose synthesis or the gene for polymerase. Plasmid pX4 contains only a small part of the dps region but includes the gene encoding transferase I and the four genes for dTDP-rhamnose synthesis that were reported by Pollock et al. to be sufficient to result in an increase in production of polysaccharide in *Sphingomonas* strains.

Strain Production

The four plasmids described above were then introduced within *Sphingomonas* strain ATCC No. 53159 by triparental conjugation as described above to form the novel S657 engineered strains (S657/pS8, S657/pS6, S657/pX6 and S657/pX4. Fermentation was followed, as described above, thereafter in order to produce a biogum material as noted below. All four plasmids had a beneficial effect on diutan productivity; however, the pS8 plasmid surprisingly also provided extremely large increases in diutan viscosity, and increase in molecular weight. The DNA sequence ofpS8 (26278 bps) (DNA Sequence No. 1) is provided and the encoded genes are listed in Table 1 below, and in diagram form in FIG. 1. The insert DNA in plasmid pS8 includes genes dpsG through rmlD and a portion of genes dpsS and orf7.

The following gene table is basically a list of the genes represented by the DNA sequence for insert in plasmid pS8 as provided within FIG. 1

TABLE 1

Genes on pS8 plasmid insert

| Start | End | Name | Description |
|---|---|---|---|
| 2* | 1054 | dpsS | (partial) homologous to gelS |
| 2738 | 1113 C | dpsG | putative polymerase |
| 4895 | 2898 C | dpsR | putative lyase |
| 5093 | 6031 | dpsQ | putative rhamnosyl transferase IV |
| 7082 | 6111 C | dpsI | unknown |
| 7121 | 8167 | dpsK | beta-1,4-glucuronosyl transferase II |
| 8164 | 9030 | dpsL | glucosyl transferase III |
| 10467 | 9079 C | dpsJ | unknown |
| 11076 | 12374 | dpsF | unknown |
| 12389 | 13306 | dpsD | putative polysaccharide export protein |
| 13341 | 14687 | dpsC | putative polysaccharide export protein |
| 14687 | 15394 | dpsE | putative polysaccharide export protein |
| 15405 | 16286 | dpsM | putative polysaccharide export protein |
| 16270 | 16968 | dpsN | putative polysaccharide export protein |
| 18454 | 17060 C | atrD | putative secretion protein |
| 20637 | 18451 C | atrB | putative secretion protein |
| 21229 | 22641 | dpsB | glucosyl-isoprenylphosphate transferase I |
| 27757 | 23635 | rmlA | glucose-1-phosphate thymidylyltransferase |
| 23632 | 24198 | rmlC | dTDP-6-deoxy-D-glucose-3-5-epimerase |
| 24202 | 25263 | rmlB | dTDP-D-glucose-4,6-dehydratase |
| 25263 | 26129 | rmlD | dTDP-6-deoxy-L-mannose-dehydrogenase |
| 26277* | 26146 C | orf7 | (partial) unknown function |

*First in-frame codon, the start codon is not present

Diutan Production

Diutan production by the engineered plasmid-containing *Sphingomonas* S657 strains compared to the S657 wild-type strain without a plasmid was determined in three sets of fermentations run in the same liquid media in Applikon 20L fermentors, with agitation and aeration. For the plasmid containing strains, the antibiotic tetracycline at 5 mg/L was added throughout the fermentation to ensure retention of the plasmid. KOH was added as needed to control pH. Two seed stages were used with 1% to 6% inoculum transfers. Media used for fermentation contained corn syrup as carbohydrate source, an assimilable nitrogen source and salts. Nutrients that can be used for fermentation are well known in the art and include a carbohydrate, for example, glucose, sucrose, maltose or maltodextrins, a nitrogen source, for example inorganic nitrogen as ammonium or nitrate, organic nitrogen such as amino acids, hydrolyzed yeast extract, soy protein, or corn steep liquor, and additional salts containing for example, chloride, phosphate, sulfate, calcium, copper, iron, magnesium, potassium, sodium, or zinc.

As a measure of the resultant diutan production, broth viscosity and precipitated fibers were determined. The viscosity of the fermentation broths was measured via a Brookfield viscometer run at 60 rpm with a spindle #4, and the results are shown in Table 2. At the end of the fermentation, the broths were treated with the well-known introduction of glucoamylase enzyme to hydrolyze any remaining oligosaccharides from the corn syrup. The diutan gums produced were then precipitated from an aliquot of broth with two volumes of isopropyl alcohol. The fibers were collected on a filter and dried. In Table 2, the term DWY means the total precipitable dry weight yields of biogums after hydrolysis of excess oligosaccharides from corn syrups.

Clearly the resultant material is in higher yield with plasmids pX4, pX6, pS6 or pS8 carrying additional copies of genes for diutan biosynthesis present therein. However, with the pS8 plasmid, there was an unexpected high increase in broth viscosity relative to the increase in dry weight yield indicating that some factor in addition to increased amount of diutan produced was affecting the viscosity.

TABLE 2

Fermentation of plasmid-containing strains

| Strain | Run #1 | Run #2 | Run #3 | av. | % Increase |
|---|---|---|---|---|---|
| DWY | | | | | |
| S657 | 34.3 | 32.2 | 33.9 | 33.5 | — |
| S657/pS8 | 37.1 | 35.4 | 35.9 | 36.1 | 8.0% |
| S657/pX6 | 38.4 | 37.6 | 33.5 | 36.5 | 9.1% |
| S657/pS6 | | | 37.6 | | 12.3% |
| S657/pX4 | | | 36.4 | | 8.8% |
| Broth Viscosity | | | | | |
| S657 | 5150 | 4950 | 5550 | 5217 | — |
| S657/pS8 | 6650 | 6850 | 6850 | 6783 | 30.0% |

TABLE 2-continued

| Fermentation of plasmid-containing strains | | | | | |
|---|---|---|---|---|---|
| Strain | Run #1 | Run #2 | Run #3 | av. | % Increase |
| S657/pX6 | 5400 | 6250 | 5125 | 5592 | 7.2% |
| S657/pS6 | | | 6675 | | 28.0% |
| S657/pX4 | | | 5525 | | 5.9 |

Clearly, there was a higher yield of resultant material with any of the four plasmids present therein, whereas the pS8 and pS6 plasmids permitted a highly unexpected increase in broth viscosity thus indicating high product quality as well. The quality, i.e. viscosity, of the resultant diutan gum products was then determined.

Diutan Rheology in Applications Tests

These diutan gum samples were then analyzed in terms of potential beneficial uses within two different areas: oilfield additives for oil recovery and cement additives for water retention and quick set-up.

The oilfield industry relies upon what is termed a "sea water viscosity" (SWV) test as an estimate of acceptable performance for gums for oil recovery. Such a test basically is an indicator of the effectiveness of a gum to increase viscosity in briny conditions of water (to replicate recovery from seabeds, for example).

The prediction of the viability of a resultant gum as a proper viscosity modifier for oil recovery purposes is generally accepted in terms of viscosity modification of a test sea water formulation. Such a "Synthetic Seawater" formulation is produced by mixing 419.53 grams of Sea Salt (ASTM D-1141-52) in 9800 grams deionized water. For the seawater viscosity test, 0.86 grams of the sample gum is added to 307.0 g Synthetic Seawater and mixed at approximately 11,500 rpm in a Fann Multimixer (Model 9B5, part number N5020) for 35 minutes. At the end of 35 minutes, the solution is cooled to approximately 26° C. before the viscosity is measured. For the 3-rpm reading, the sample is placed on the Fann sample platform (Fann model 35A; Torsion spring MOC 34/35 F0.2b; Bob B1; Rotor R1) and the speed is adjusted to 3 rpm by turning the motor to low speed and setting the gearshift in the middle position. The reading is then allowed to stabilize and the shear stress value is read from the dial and recorded as the SWV 3 rpm dial reading (DR). For the 0.3-rpm reading, a Brookfield viscometer is used (Brookfield LV DV-II or DV-II viscometer, with LV-2C spindle) to measure the viscosity. The speed of the spindle is set to 0.3 rpm and the spindle is allowed to rotate at least 6 minutes before the viscosity is recorded as the SWV-0.3 rpm reading and expressed in centipoises (cP). For cement applications, the PEG LSRV test (a low shear rate viscosity using polyethylene glycol as dispersant as outlined below) provides an indication as to effectiveness of performance of a viscosity modifier to that industry. Such a test measures the viscosity of a 0.25% solution of biogum in Standard Tap Water (STW). STW is prepared by adding 10.0 grams NaCl and 1.47 grams $CaCl_2.2H_20$ to 10 liters deionized water. For the viscosity measurement, 0.75 grams of biogum is added to 4.5 grams Polyethylene Glycol 200 (CAS 25322-68-3) in a 400-mL beaker and thoroughly dispersed. Then, 299 grams of STW are added to the beaker and mixed for approximately 4 hours using a low-pitched, propeller-style stirrer at 800±20 rpm. After the 4-hr mixing time, the beaker is placed in a 25° C. water bath and allowed to sit undisturbed for approximately 30 minutes. The viscosity is then measured using a Brookfield LV viscometer equipped with a 2.5+ torque spring (or equivalent instrument such as Model DVE 2.5+) at 3 rpm using the LV I spindle after allowing the spindle to rotate for 3 minutes and expressed in centipoises (cP).

The diutan samples produced above were tested in this manner: the results were as follows:

TABLE 3

| Rheology of diutan from plasmid-containing strains | | | | | | | | |
|---|---|---|---|---|---|---|---|---|
| | SWV3 rpm | | | SWV-0.3 rpm | | PEG LSRV | | |
| Strain | Run #1 | Run #2 | Run #3 | Run #1 | Run #2 | Run #1 | Run #2 | Run #3 |
| S657 wild-type | 25 | 26 | 22 | 24400 | 28600 | 2820 | 3150 | 2280 |
| S657/pS8 | 42 | 43 | 47 | 41500 | 38800 | 4720 | 4980 | 4920 |
| S657/pX6 | 25 | 29 | 26 | 25000 | 29100 | 2860 | 3400 | 3270 |
| S657/pS6 | — | — | 22 | — | — | — | — | 2270 |
| S657/pX4 | — | — | 24.5 | — | — | — | — | 2950 |

SWV = viscosity in sea water
LSRV = low shear rate viscosity

Unexpectedly, there are definite increases in viscosity exhibited by the inventive diutan gums produced by some of the engineered plasmid-containing strains Most surprisingly, however, is that the increase in viscosity for SWV at 3 rpm for the pS8 strain is 80%, whereas the same analysis made for the pX6 strain is merely 9.6% over the wild-type results. Plasmids pS6 and pX4 had no significant increase. Likewise, the lower SWV rpm test reveals an increase of 51.5% over the wild-type for the pS8 type versus just over 2% for the pX6. Finally, the polyethylene glycol LSRV test showed that the pS8 results were in excess of 77% viscosity increase over the wild-type gum, as compared with less than 16% increase for the pX6 diutan, and 7.2% increase for pX4 and no significant increase for plasmid pS6. Again, the highly unexpected results in these terms shows the drastic improvements accorded diutan gum production via the utilization of the needed gene sequence exemplified within the pS8 plasmid, as one manner of introducing such a sequence within a target diutan-producing bacterium.

Thus, the inventive diutan produced via the introduction of pS8 exhibited surprisingly increased viscosity measurements on all three counts, particularly as compared with the wild type and pX6 plasmid-produced varieties. Thus, it was expected that such a novel diutan would function extremely well under typical oilfield conditions and within cement applications.

Fundamental Explanation for Rheology Improvement

The previous examples showed that diutan from the S657/pS8 strain showed a significant increase in rheological parameters. Such a substantial increase in the sea water and PEG low shear rate viscosity measurements thus cannot be attributed to the increase in productivity alone since the pX6 strain also exhibited similar, if not greater, yield results. Indeed, in the prior example illustrated by Table 2, the dry weight yields (alcohol precipitable matter) increased by 8.0%, while the rheological parameters increased significantly more for the S657/pS8 strain (52-80%). A fundamental study was pursued to explain why rheological improvements are obtained with strain S657/pS8 over the wild-type strain.

Intrinsic viscosity is a well-known technique in polymer science to infer the molecular weight of macromolecules (C. Tanford, 1961. *Physical Chemistry of Macromolecules*. John Wiley & Sons, New York). The intrinsic viscosity is obtained by plotting the reduced viscosity (viscosity normalized for concentration) versus the solution concentration, and extrapolating a linear regression of the data to zero concentration (the y-intercept of the plot). Surprisingly, the resultant gums exhibited increases in intrinsic viscosity as noted below in the following table.

Five diutan samples, two from the wild-type strain (Control 1, Control 2) and three from the S657/pS8 strain (Sample 1, Sample 2, Sample 3) were evaluated for intrinsic viscosity, neutral sugars, and organic acid analyses. These samples were purified by alcohol precipitation, re-hydrated, treated with hypochlorite, treated with glucoamylase, treated with lysozyme, and finally treated with protease (in that sequential order). They were then recovered at a 4:1 CBM: Broth ratio, dried and milled. CBM is an azeotropic isopropyl alcohol/water mixture including ~82% by weight of the isopropyl alcohol.

The samples were tested for moisture content by performing the following: generally, two 0.7 gram aliquots of sample were tested using a Mettler HB 43 halogen moisture balance. The results from the two trials were then averaged and these results were utilized for moisture correction.

After obtaining the moisture data, a 0.2% solution of the gum was prepared in 0.01M NaCl on a moisture corrected basis. For these trials 200 grams total of the 0.2% solution were prepared. The gum was weighed on an analytical balance to the nearest ten thousandth and added to the water weighed to the nearest thousandth. The samples were stirred for two hours using a 2.5 inch diameter propeller mixer @1000 rpm in a 400 ml tall form beaker.

Following initial hydration, each sample was diluted to 0.02% using 0.01 M NaCl. This was done by weighing 20 grams of the 0.2% solution into a 400 ml beaker, then adding back 180 mls of the diluent. The diluted samples were mixed for an additional 30 minutes. The final dilutions ultimately used for determining the intrinsic viscosity were prepared from this sample. Each diutan sample was evaluated at the following concentrations: 0.004%, 0.008%, 0.010%, and 0.012%.

Figure 2:
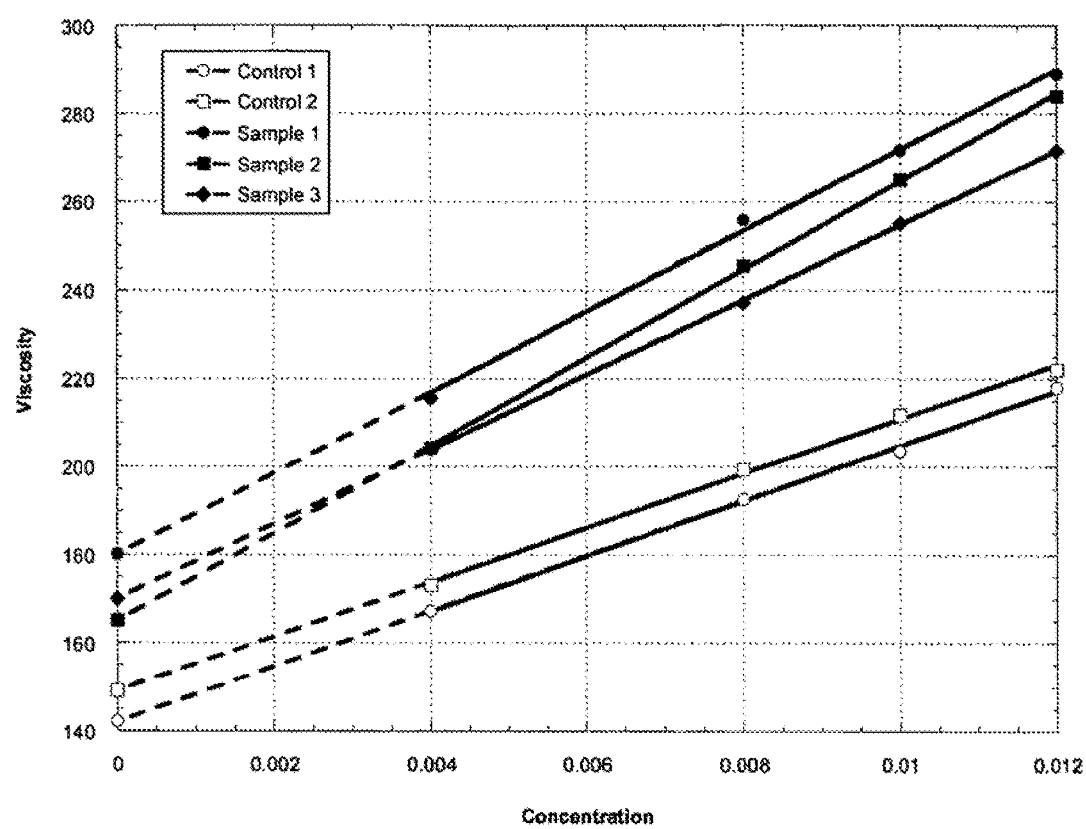
FIG. 2 is a graphical representation of the improvements in intrinsic viscosity measurements achieved by such inventive diutan biogum materials.

Viscosity measurements were carried out using the Vilastic® VE System. Prior to measurements the Vilastic was calibrated with water to less than 2.0% error. The samples were measured using the Timer program @2 Hz, a strain of 1 and a shear rate of approximately 12 l/sec, all at a constant temperature of 23° C. Five measurements were made for each sample and averaged. The averaged viscosity data were then used to calculate the intrinsic viscosity. FIG. 2 and Table 4 below provide the final results of these trials.

TABLE 4

Comparison of Diutan Based on Intrinsic Viscosity Calculations

| Diutan Sample | Measured Solids | Intrinsic Viscosity |
|---|---|---|
| S657 Control 1 | 93.76 | 138.3 |
| S657 Control 2 | 92.42 | 143 |
| S657/pS8 Sample 1 | 91.7 | 170.7 |
| S657/pS8 Sample 2 | 91.4 | 162.2 |
| S657/pS8 Sample 3 | 91.94 | 162.8 |

These results indicate that the S657/pS8 strain consistently produced diutan with significantly higher intrinsic viscosity; in fact the average reduced viscosity for the inventive strains was 165.2, whereas the control was 140.7, all at similar measured solids levels. This finding indicates that diutan produced by S657/pS8 is higher in molecular weight than the wild-type control.

FIG. 2 is the graphical representation of these trends showing the consistent higher intrinsic viscosity measured at similar solids content between the control and inventive strains.

To determine if the higher viscosity diutan gum from S657/pS8 had the same composition as diutan from the wild-type strain, the composition was determined by testing for neutral sugars and organic acids. The purified sample used for intrinsic viscosity measurements were used for neutral sugar analysis. An aliquot of each purified sample was hydrolyzed to component sugars by hydrolysis with trifluoroacetic acid (100° C./~18 hr). The hydrolysate neutral sugars were quantified by high-performance anion-exchange chromatography with pulsed amperometric detection. The hydrolysate organic acids were quantified by high-performance ion-exclusion chromatography with chemically suppressed conductivity detection. Table 5 summarizes the results from the neutral sugar analysis. As shown, the neutral sugar profile for the S657/pS8 strain is nearly identical with the neutral sugar profile for the S657 wild-type strain. Although both results are different from the theoretical values, these results indicate that the structure of the repeat unit of the diutan gum produced using pS8 is the same as that for wild-type and that any increase in viscosity imparted by the pS8 material is due to longer chains, meaning higher molecular weight.

TABLE 5

Neutral sugars and organic acid analysis for pS8 and wildtype (control) diutan strains

| | Strain | % Rhamnose | % Glucose | % Acetate |
|---|---|---|---|---|
| Sample 1 | S657/pS8 | 32 | 19 | 8.9 |
| Sample 2 | S657/pS8 | 32 | 19 | 8.2 |
| Sample 3 | S657/pS8 | 32 | 17 | 8.6 |
| Control 1 | S657 wildtype | 30 | 18 | 8.6 |
| Control 1 | S657 wildtype | 33 | 20 | 8.7 |
| AVERAGE | S657/pS8 | 32 | 18.3 | 8.6 |
| AVERAGE | S657 wildtype | 31.5 | 19 | 8.65 |
| THEORETICAL | — | 46 | 30 | 8 |

The greatly improved seawater viscosity and PEG low shear rate viscosity of the diutan produced by the S657/pS8 engineered strain is thus attributable to an increase in molecular weight or length of the diutan molecule, i.e., more repeat units per molecule and not to a change in its composition and thus not to changes in the repeat structure itself. Nor can this improved rheology be due solely to increase in amount of diutan produced. Although four plasmids, pS6, pS8, pX4, and pX6, with different portions of the cluster of genes for diutan biosynthesis cloned, were evaluated, and all showed some increase in productivity, only plasmid pS8 showed the unexpected and very high increase in rheological parameters of the recovered diutan product.

A comparison of the genes for diutan biosynthesis cloned in the tested plasmids suggests that the most likely gene to be responsible for the increase in molecular weight is the gene dpsG, since this gene is present in pS8 and not in the other plasmids. Gene dpsG encodes a hydrophobic membrane protein with strong homology to other membrane proteins involved in polysaccharide synthesis. A portion of the protein has homology to proteins for polymerase, an enzyme which catalyzes the linkage of repeat units to form the high molecular weight polysaccharide. The homologous gene gelG in S60 has been postulated to function as a polymerase for gellan synthesis (Harding, N. E. et al. 2004.

"Organization of genes required for gellan polysaccharide biosynthesis in *Sphingomonas elodea* ATCC31461". *J. Ind. Microbiol. Biotech.* 31:70-82. Sa-Correia, I. et al. 2002. "Gellan gum biosynthesis in *Sphingomonas paucimobilis* ATCC 31461: Genes, enzymes and exopolysaccharide production engineering". *J. Ind. Microbiol. Biotechnol.* 29: 170-176.). Homologues of dpsG have also been isolated from *Sphingomonas* strains ATCC 31554 and ATCC 21423 producing polysaccharides S88 and S7 (Pollock et al. U.S. Pat. Nos. 5,854,034, 5,985,623 and 6,284,516, and Pollock, T. J. U.S. Pat. No. 6,709,845). It is thus very likely that additional copies of the gene for polymerase may have an effect on increasing the molecular length of the diutan molecule. It cannot be ruled out that other genes in the diutan biosynthetic gene cluster may be required in combination with dpsG to achieve the observed increase in viscosity. Likely candidates would be the genes dpsB, dpsL, dpsK and dpsQ encoding the sugar transferases I, II, III, and IV, in particular the gene dpsB which encodes transferase I that adds the first sugar of the repeat unit to the lipid carrier. Other important genes may be dpsD, dpsC and dpsE, which are homologous to genes gumB and gumC that have been shown to increase the molecular weight of xanthan when amplified on a multicopy plasmid. It is possible that all genes cloned in plasmid pS8 may be required to achieve the dramatic increase in viscosity.

While the invention will be described and disclosed in connection with certain preferred embodiments and practices, it is in no way intended to limit the invention to those specific embodiments, rather it is intended to cover structural equivalents and all alternative embodiments and modifications as may be defined by the scope of the appended claims and equivalence thereto.

DEPOSITS

The following bacterial strain was deposited with the Patent Depository at the American Type Culture Collection at 10801 University Boulevard, Manassas, Va. 20110, on Oct. 21, 2005, pursuant to the Budapest Treaty for the International Recognition of the Deposit of Microrganisms: *Sphingomonas* strain S657 with plasmid pS8.

What we claim is:

1. A genetically modified strain of *Sphingomonas* comprising increased expression or multiple copies on a plasmid of a coding sequence, wherein the coding sequence comprises an isolated nucleic acid molecule which encodes SEQ ID NO: 5, 7, 9, 11, 13, 15, 17, 19, 21, 23, 25, 27, 29, 31, 33, 35, 37, 39, 41, and 43, or an at least 95% homologous coding sequence.

* * * * *

SEQUENCE LISTING

```
<160> NUMBER OF SEQ ID NOS: 45

<210> SEQ ID NO 1
<211> LENGTH: 26278
<212> TYPE: DNA
<213> ORGANISM: Sphingomonas sp. ATCC53159

<400> SEQUENCE: 1

gatcaacggc gccttgctcg gacggcacaa attcgtcctg gtcaatgtgt ccacggtcgc      60

ctcttcgata ctgttccagc tgttcccgct tgtcgtcgcc tggatgatcg gcccggacct     120

gcgaacgctg ctgatcgccg cgctcgttgg ccgggcggtt ccgatgatcg gcatgctgcc     180

cgcgctgtat cgaaaccttt tgcgcggcaa cacgccgcgt tttcacgcca gcgaggcgcg     240

cttcctgata ggctatggcg ggtgggcctc gctcacgacc gtggtagcga ccgtgctcat     300

gatggcggac cgcttcctga ttggcgcact tcttgggccc gtcgccgtga ccatctacac     360

ggccccccctg caactcgcac agcgcgtatc gctgctgccc tccgcactgt ccgccgcgct     420

gttcccgcgc ctgcccagcg cgacgccggc ggagcgcatg gcgcttcaga tccgctcgct     480

gtcgctgatc atgggcggcc ttaccgggat gatcggcggc ggactattgc tggccgcgcc     540

gtttctcgat ctctggatcg gcaagtcgct cggccatgcg ggaacgccgg tcgcgctctt     600

cctgttcttc ggcgcatggt ggaatgcgct ggcgatcatt tcgttcagcg gcctgcaggc     660

gagcggacgg ccgaaagcga gcgcgatcgt ccagggggca gagctgctac ccgtgttgat     720

cgcgctgtat gcagggatcc gatggggcgg cgtgaccggc gccgcagcgg tctttctggg     780

acgctccgcc ctggatttcg tcctgttgac ctggcaggca ggcctgctcc gccagacggt     840

gaagcaagta tccgtatgcg gcgccgttct caccgtcgcg atgctcgtgg gcgcgaccta     900

tcgctattcg gtgccgctct ggtgcgtact cagcgcctgc tgcctggtcg cgctggcagc     960

ctgctcctgg tggacattgg cgcgccagga caaggcactg ctgattggac gattgagccg    1020

aattctacca aagcagcggc aactcgacct atagcctttc cgcaatgcac cgatggacca    1080

caccaacccg ttttaattga cacacacaaa tgctacaccg acaaagacac aggccgagag    1140

cgatatagaa gcgctatgcc tagccccagc gtcataaaga tgaacgggtc attgtcacct    1200

tgcgacagga ctgaccgcgt atttaaaaga acagccagga aagttgctac ggcgagctca    1260
```

-continued

```
agcgggtagc catctccgct catcttaaga ccacgaaacg cgagcaaaat cattaacgta   1320

atcatcgtgc cgtatagcga aacaaaaccc agcaagccgt aatcagccgc tacggacagg   1380

aaaccactgt cgatcgatag gaagccttgc tgattacgcc acccgacagc gccagcaccc   1440

tctcccgggc catagccgaa gaaagggcgg cgagcgatgg caggcacgcc caagcgaaac   1500

tgctcctgcc tgccttgatt gctaagttga gaagcgcctc caccgagaac acggttgtgg   1560

acggcaggca cgaacatgac cgccagcgac agcgccacca tcaaggcggg atacgtcaac   1620

gtcagcgaaa tgccgacaag cccgcccttt gtggtccgcc accgccgaat tgcccaaata   1680

agcaaataca cggtatgcgc caccaatccc cccaccattg ccagtcgaga accgctaaga   1740

aatccggacg caactacaag aaaatcgaag aaaatccaaa atgccaatct ccctacgcca   1800

cgggaattcg ctatacggtg cagcacgaaa ggaatcgtca aagccgtcaa ctctccccag   1860

acaagcggac tgctgaaagt cgtcaaaacg cggtaagtac cccggaaacc gggcgtaagc   1920

actacggtaa gaaactgctc atcaacgcgc aggaagctcg gaatcgagta ggcccagagg   1980

acgtgcttca cccggaactc cagcacgcca atcgccatca gcacgcccac gcaccaaaac   2040

aagcgcgtaa cccaccactc cggggtgcgc gtgtcggtcc cgatcagcca tagcgagatg   2100

aatgccatcg gcgtcaccgt cagaacgatg ccaatcaacc gcggaattgt ttgcgaggcc   2160

gctggggtcg caatggaggc gacgatctgg accataatga aggcaagcaa tagtcgcgat   2220

gggatcggcg ccgcccgcat aatcgccgcc atctcggatc gaaacttttt cgagaccgaa   2280

agcgagatca tgagcgtgag caatgcgatc gaaccgatca tccgcctgat cgagatccaa   2340

ggcaaaccac caacgctgag cgcaagatag ttcggccaca cgagcgccgc caccatatag   2400

gcgaggtata gttttgccag caggcgagta ggcgcctgcc gcgcctcggg tagcgcccag   2460

atcactacga gcgccatcag aacgaggggc acggccggga tcgccagcat ctggagcggc   2520

agaactgcgg cgagcaggcc gtagactgcg gcaagaaaca tcacgctgac cagcagaacg   2580

gtacgccgcg ccgcgatcgt cacgcctgat cgctcggctt tgtagacggg cagtaccggg   2640

atcgctggct ttgtcagaaa ccgaaccagt cgcaacctgc gaagccgctg catcgctccg   2700

tggaaggccg ggcgacgaaa cgccgaggta gtcgtcatct gcaagtcccc aacaagtccc   2760

caagaggcgc tgccgctcgc atgatcgaag ggttcgcgaa aagcaaggtc gatacgccgc   2820

actccctgcg atgtgccgcc ggatcgcagg agggcacggg cggcgccggc gcaaggccgc   2880

tcaccgcccg cccccgctca ggcgcggtac aggttgtact gatccgccgt agcgctcagt   2940

gtcgccgcgc tgcggattgc gcccatcgcc cccgcggtca tcatgtcgac accgatcttg   3000

ctgacgagcg cgatctgcga ggacgcggca gtacctatag acagcgtact gcccaccgtg   3060

gccaccgtcg caagcggcgt tgccgtgcta gcggcgccgg cacccgccag cagcgcagcg   3120

gcctgcgcgg ccgcgccggt gacgaggctg tccttgaccg tcgccgccgc gctggcgctc   3180

gacgcggtca ccagcgcctg cacctgggcg gcgctgatcg cgccatcgcg gatctcgatg   3240

tcgccgaccg ttccgctgaa tgcggtcgag aacgggctgc cgacatacag cccccaggat   3300

tcggcgggcc gggtcgtgcc ggtcatcgtc gctgtgccgc gttgcatgcc gtctacgtac   3360

agaatcgcgg ttttccgcgt gctgtcgtag gtcagggcga tcttgtgtgt ggcagcatca   3420

agcagcttgg cgccgctcgt caccattgtc tggctgacgc ccgcggcgtt gcgcatggtg   3480

aagctcagtt ccccattggc ctgcagcgaa accgaccagc tctggaagat gccaagaatt   3540

tgcccggccg tggccgtagc cgagtcccgc ttgaggtcga agctgagcgt gaacgccgac   3600
```

-continued

```
aatgcgtaaa tctgccgcga atagctccgg tttagttcca cccccgtgcc cgtcgagacg   3660
tggaaggcgc tgcccacgac cgccgacacg tccaccgcct ttgtcgtctg gccggtattc   3720
cagtgcgaaa ggtccacgac gccgctgttg ctgaacgaca gatcgagcag cagcgacgga   3780
tttgccgcct tcgcagtcga cagttcggta gtcacctgag cggcagcagc gctcgacacg   3840
ggcggctggt acccgacgcc gggaacgatc aaatcgctga gccgcgccgt agccccatcg   3900
ttgaggccat agatcttgcg gatcgttgcc gagtcactcg tcagcgtacg attgcctgtc   3960
tgcacgatat tgctcgagga gcttgtgacg gtgatcaggt ccgcaacatt gttcttgatc   4020
gtcgcgccat tggttttgtc gaggcgaatc caaaatgatg tgccatccac ttgcgatatc   4080
acgctattgg attcgatatt gacattaacg ccgttaacaa cgttgatacc gtggtaataa   4140
ccattcagat agataagatt gtttttgatg tttacattga catagggaag attaccggcc   4200
tcgtcattca tgaaaatccc ttgcgcgcca gagcccgcgc cctgcatgat gacgttattg   4260
gagatggtga tgttggtatt gcccttgacc ttgcccgccg tgaagaactg aatggcgtcg   4320
ggatgttcgg tgcccacggg aaacaggttc gtgaacgaat ttccgtcgat gacaagattg   4380
ttcatctcag tgaagttcgt atgatcgcgc cggttgtcgt ggaagctgct gttctggacc   4440
accatgccat cgacgttgta ggcctcaagg cccagaccga agtggtcgat agacgaattc   4500
tgcatcgtca ccgacgtgct gttgcgcacg aacaagcccg ccccttcga gagcgaaggg   4560
tcaccagtgc cgccgctgaa ccgcacgccg tccaaaacga tgttggccga accctggatc   4620
gtattcagtc gattccagtc atcggcgggc ttgtaatcgg tcgcagcgac catgtttttg   4680
acggtaacgt tgctactgtt cccgatcacc agcttttgga tattgaccgg gttcgacgag   4740
tcgagcgact caattgtcac catgctggta aacgtcttgg tcattacagt gagatctgtg   4800
tagaccccgg cggcaagctt gatggtttcg ccacccttcg ccgccgcgat tgcagcattc   4860
aactccgtct gattcttgac aatgatatcc ggcatgttga cttaccccgt acgcacgaac   4920
ccgggccgat attgaccctt ccattgtcat aaataccaga acagccatga aatttgctcg   4980
aagggataca gttaagaact cccttctacg gggccgcatg ccgggcccat gcacgcccga   5040
ctttcgccgg caccgtctcg acggcgcaac acagtgcagc tactagggtg cgatgcagat   5100
gctcccaacg cccgatgtca gcatactcgt ggtcgctttc aactcgaccg agtatatcga   5160
agactgcctg cgcggcatcg ccgaaggagc gggcaagacc ccccacgaag ttctgctgat   5220
cgacaatggc gacgggcgaa ccgaagcgct ggtccggcag cggttccacc acgtccgcat   5280
cgttcccagt gagggcaata ttggtttcgg ggccggcaat aatcgcctgg cagcgcaggc   5340
tgccggcccg ctcctgctgc tcgtcaaccc cgatgccatt ccccagcccg gcgcaatcga   5400
tcagttggtc acctttgcca aacagcatcc cgaggcggcg gcatggggcg gccgttccta   5460
ctcgcccagc ggcgatctag aacccgcaaa tttcatgtcc ctgccgacgc ccgccgactt   5520
tctgacggcg attttcaacg cgcgtgcgct acgcagcggc gggctgcaag aaggcgcgac   5580
cacccccgga gcggtcgagg tgttgaatgg cggcttcatg atggtacgca ccgatgtctg   5640
gcaggcgatc ggcggttttg acgagagctt ttttctttat tcggaagaga tcgatctctt   5700
ccagcgaatc cgcacgttgg ggcacaaggt gctcgtcgac ccctcggtca aagtggtaca   5760
caatacgggg agtggtcagt cgatgtccca gaaccgcctg atgtatctca cgaccgggcg   5820
catgcactat gcgcgaaagc attttggcgc actcggcacc cttgccaccg ggtgcgcgct   5880
ttggctgatc gccgccaaat acacgttggt cggggcggca ctctggcgcc tgtcgccgcg   5940
gacgggcacg cgatacaaag agctgagcaa cgggtggcgt gccgtattta gcaatcctgg   6000
```

```
ccgatggtgg agcggctatc cgcgtcgcta aaagtccagc tccccccccc ctaaaggcgc   6060
cgttgggagg cggacgcatc gttgcaacaa cgcgcccgcc tttcagacct tcagttcccc   6120
gccggcgttg cgccgctgcc gcgaagctgc ggcggtgcgc tgtagccggc ctgatatttc   6180
acggtttccc gcgccttctt caggcggtcg ttgagctgtg cgtcagccgc cttgccgaag   6240
cgctcggtac gcagcccgct gagcgcgatc tcgcgcgcct ggtcggccgg caccggcagc   6300
accgtggtcg acgtgatgat attcgcggtc agtccctgct gggtcggcag gatgaacatc   6360
tcctgtgccg gcagcgacgc gatcttggca gcgatttccg gcggcagcgc agcggtgtcg   6420
atctgcgacg gcgcgcgacg gaactggaca ttgtccgccg agagcttggc ggttagctgg   6480
tccagcgtct tcagcggcgc gaattgcttg agctttgcgg ccgagctcgg cggagcgaag   6540
acgacctgat cgatcgcgta gatcttgcgc tgcgcgaacc gctccggatg cgcggcctga   6600
tatttctcga tctcggcatc ggtcggctgg gcgatgccgc cggcgatctt gtcgcgcagc   6660
atggcggtga ggatcagctc gtcggcccgg cgctcctgga tcaggaaggc aggcgtcttg   6720
tccagcttct gctcgcgggc gaccttggcg aggatcttgc gctcgatgat gcgctgcagc   6780
gccagctgct cggccagctt gcgatcggtc cccgggggta cctgggaggc ctgcagttcg   6840
gcattcagct cgaagacggt gatttcttcg ccatcgacgc tggcgaccac ctgccccttg   6900
tcgagcttgc cgcccttgcc gccacatccg gagacggcca gcgcggccgc agccaccgcc   6960
gtaaccaggt acaatttctt catgaagacc tccccgccgg cacggaattg cgcacggcac   7020
aaacttctac ttgaacctat tcggacgggc gggcatccgc aatagcgttg gcagtgcagc   7080
atggttctaa gcggagccag gcggcaacaa gggggacgag atggcagaag cgaacgcggt   7140
agatggaaag gcctccaagc cgctgaaaat gtgccttgca gcgtcgggcg gcggccatct   7200
ccggcaaatc ctcgatctgg aatcggtgtg gcgcgaacac gattatttct tcgttactga   7260
agataccgcg ctcggccgga gccttgccga aaaacatccc gtcgaactgg tggagcacta   7320
tgcgctcggc caggccaagc tgggccatcc cttgcgcatg ctgggcggcg catggcgcaa   7380
cctgcgccag agcctttcga tcctgcgccg gcacaagccg gatgtggtga tttccaccgg   7440
cgcgggcgca gtctatttca ccgcgctgct cgccaaactg tcgggcgcca agttcgtcca   7500
tatcgaaagc ttcgcgcgct tcgaccaccc gtctgccttc ggcaagatgg tgaagggcat   7560
cgcgacggtg acgatcgtcc agtcggcggc gctgaaagaa acctggcctg atgccgagct   7620
gttcgatccg ttccgcctgc tcgatacacc gcgcccgccc aagcaggcgc taatcttcgc   7680
gacggtcggc gccaccctgc ccttcccgcg gctggtgcag gcagtgctcg acctgaagcg   7740
cgccggcggg ctgccgggca agctgatcct gcaatatggc gaccaggacc tgcccgatcc   7800
cggcatcccc gacgtcgaga tccgccgtac catcccgttc gacgatctgc agctgctgct   7860
gcgcgatgcg gatatggtga tatgccacgg cggcaccgga tcgctggtca cggcgctgcg   7920
cgccggctgc cgggtcgtcg cctttccgcg ccgccacgat ctgggcgagc attatgacga   7980
tcaccaggaa gagatcgccc agaccttcgc cgaccggggc ctgctccagg cggtgcgcga   8040
cgagcgccag ctcggcgccg ctgtggaagc ggccaaggca accgagccgc agctggcgac   8100
caccgaccac acggccctcg cggcgcggct gcgccagctg ctggcgcagt ggagtgccaa   8160
gcgatgagca cgccccggat cagcgtcgtc atcccgcact ataacgatcc gcaatccttg   8220
cggctctgcc tggatgcgct ggagcggcag acgatcggtc gcgacgcgtt cgagatcatc   8280
gtcggcgaca acaattcgcc ctgtgggctc gcggcggtgg aggcggcggt cgccggacgt   8340
```

```
gcgcggatcg tgaccattct ggaaaagggg gcgggccccg cgcgcaacgg ggcggcagcc   8400
gcagcgcgtg gcgagatcct cgcctttacc gacagtgact gcgtggtgga gcccggctgg   8460
ctggcgggcg gcacgaccag ggtcgcgcct ggccgtttca tcggcgggca catgtatgtg   8520
cgcaagcccg aagggccgcc gaacggcgcc gaggcgctgg agatggcgct ggcgttcgac   8580
aatgaaggct atgtgcggcg cacccagttc acggtcaccg caaacctgtt cgtgatgcgc   8640
gccgatttcg aacgggtcgg cggcttccgc gttggcgtgt ccgaggatct ggaatggtgc   8700
caccgggcga tcgccagcgg cctcaccatc aactatgcac cggatgcatc ggtgggccac   8760
ccgccccggc ccgactggtc ggccctgctg gtgaagacgc ggcgcatcca gcgcgaactc   8820
tatctgttca acatcgagcg gccgaagggc aggctgcgct ggctggtccg ttccgtggcg   8880
caaccggcga tgatcccaca ggacgtggcc aagatcctgc gcacaccggg taccaagggc   8940
gcgcgcctcg ctgcggtcac cacgctggtc cggctgcggc tgtggcgcgg cggcgccggc   9000
ttgttgcagt tgctcggccg cgacatctga tcgaccggcg atcggccgac gagcgcgtcg   9060
ccggccgatc gcattgcatc agacggtggc cagcgcgtct tccagcgtgc cgctgtcgag   9120
ccgcaggcgg ccgatcatca gccacagata gaccggcagc gtatcgtcgg tgaagcggaa   9180
gcggcaatcg ccgtcctgcg tttcggattc gaggccgagt tgaccggtga gctcgcccag   9240
ctcctgctcg acctgcgccg ccgtgatgtg cgcgcccggc agcagatcca ccacggcttg   9300
gccgctgaac cagccatccg ccgagcgcga ggcctcgccc agcgccgcga cgagtggatc   9360
gtagcggccg ccgacgaact tgcgcatctc gatcaccgcg cgcggcggca tgcggccctc   9420
gatctcaagg atcgcctggt cgagcgcacg acgcagatgc ccggcgtcga ccgtgaggcg   9480
gccctggtcc agggcttcca gcgcggaatg gtggcacagc agccgcgcga aatagggcga   9540
ccccagcgcg agcaggtgga tcatgtgagt caggtccgga tcgaagcgaa cgcccgaggc   9600
ggtttcgccg agcgcgatca tctcctgcac ctccgattcc tccagccggg gcatcggcag   9660
gccgatgacg ttgcggcgga tcgacggcgc ataaccgatc agctcctgca ggttcgaggc   9720
gacgcccgcg atcaccagct ggacgcgcgc cgaacggtcc gacaggttct tgatcagctc   9780
ggcgacctgc tgacggaagg cggaatcgct gacgcgatca tattcgtcga ggatgatcag   9840
cacgcgtgtg cccgtgatgt cggcgcacag gtcggccagt tcgccgggcc cgaagctgcc   9900
cgtcggcagg cggtcggcca agttgccgcc gctctccgcc tcgccggcgt tgggcgccac   9960
gccgcgatgg aacagcagcg gcacgtcttc cagcacggcg cggaagacat cgctgaaatt  10020
cgcgttcgca ccgcaggtcg catagctgac gatatagctg gattcgcggg cgacatcggt  10080
cagcacgtgg agcagcgagg tcttgccgat gccgcgctcg ccatagagca cgacatggct  10140
gcgctggctc tcgatcgagg agattaggcg cgccagcacg ccgaggcgcc cggcgaagct  10200
cgaccgatcg gccaccggct gggtgggtgt gaagaaggtc gccagcgcga accgggcgcg  10260
cgtgatctcg cggcgctcgt cgcggcggcg atccagcggg cggtccagcg cggaggcacg  10320
gaaggttggg aaatccgggc gaccacggcc gctatgggca tcgcgatgcg gcaccactgt  10380
cgcagtcagc gggaaatagc cctcttcttc aggttcttct cgacggccga acggccacaa  10440
gaatctcagc gcggaaccta cagccactcg aacacctctt aaattcgtgc gccatcggca  10500
ccgacggcgc accctggttc gcgccccctg gcgccccctc ctaacgaacc cacgccttgc  10560
ctggcctatc ggcgcttgaa gaactcgtac ggtttgatca ccaaggcgat gtacgccagg  10620
accagagcga tcgtcaaaat tgcaaagacg tgataattct cattgcccag ataattggcg  10680
acggcgcaac cgactgcggg cggcaaatag ctgatcatcg tgtcccggac tgccgaatcg  10740
```

```
gcttgggacc gttgcaggaa tataacgatc aggccggcaa atatcgcgat ggtgacccaa  10800
tcatagggcg tctgcatgca tgtcctttct attcgacacc ggaatcgaac catttccggc  10860
gacgctattg cacgcactag cagtgcgcgc ggccgctcgc taggtagcgc cgcaccggat  10920
aaaccgacgt taagatggcg cggctcgatc gaaatggagt caaacgggct tgcccggccg  10980
accgaagcat ggcgccatgg cgcatgcacc gtattgtgac cacgcaaacc gcgagggtca  11040
ttcgatgcgg ttgcttgtac aggaggccat tgataatgaa gccgagaccc gggggaacct  11100
ttatgcaagt aaatttcaat cgacaggctc gcaagctcgg tgccggcaat gcgctcgcgc  11160
gggggggcc cgtgcttgcg ctgcttgcga ccgcggcatg gacacaacct gcgctggcgc  11220
agcgacaggc atttgagtcc cgcccctccg gtagcgagcg acaggtcgat attcgcgcga  11280
cggggtcgct ggaatatgac gacaacgtcg tgctgaacga ccagcggatc acggacggcg  11340
cgcgtggcga tgtgatcgca tcgcccgggc tggacgtgac cctagttctg ccccgcgcca  11400
ccgggcagct ctacctcacc ggcaatgtcg gatatcgctt ttacaagcga tataccaact  11460
ttaaccgcga gcagatctcg ctcaccggcg gcgcagatca gcggttcgcc tcctgcgtcg  11520
tgcacgggga agtcggctat cagcgccacc tcaccgacct gtccagcatc ttgatccagg  11580
acaccacgcc tgcgctcaac aacaccgaag aggcccggca gtacaccgcg gatatcggct  11640
gcggcgcgac ctacggcctg cggcctgccg tttcctacac ccgcaacgaa gtgcgcaaca  11700
gccttgccga gcgccgatac gcggactcga ataccaacac ctttaccgca cagcttggcc  11760
tgacttcgcc tgccctgggg accgtggcgg tatttgggcg tatgtccgac agcagctatg  11820
tccatcgcgt ccttcccggc attaccggcc aggacgggat gaagagctac gcggccggcg  11880
tccagctcga gcgctcggtg gccaaccgac tccatttcaa cggctcggtg aattacaccg  11940
aggttgaccc aaagctcgca tccaccaaag gattcaaggg cgtaggattt aacgtttccg  12000
gcgattatgc tggtgatcag tacagcctcc aattgctggc ttcacgatcg ccccagcctt  12060
cacttcttct gttcgtgggt tacgagattg tgacagcggt ttcggcgaat gcgacgcgcc  12120
ggctgagcga tcgcattcag atatcgctgc aaggcagccg aacctggcgc gagctcgcgt  12180
cttcgcggct gctcaccaac gtgccgattt ccggcaacga caacacctcg acgttgttcg  12240
cctccgctac cttccggccg aatcgccggc tgagctttgt gctgggtgcc ggccttcagc  12300
ggcgcaccag caacacgcag ctatacagtt acagctccaa acgcatcaat ctctcgacgt  12360
cgctttcgct ctgacaaggg ccgtaatcat gcatatcaag aatcgcttcg tgaatatctc  12420
gacgttggcc atcgccgccg cgctggccac gccggcggcg gcgcagatcc ccacgcggtc  12480
cgtgcccgcg ccggcccgcc cgcggcctgc aacgccgccg gcgcaacagc agaaccaggc  12540
gccgtcgacg cccgcagcgg caaccccggc gcagaccgcc gcaaccgttg cccctgcagc  12600
aaccgcaccc gcaggttaca aaatcggcgt ggacgacgtg atcgaggccg acgtgctcgg  12660
ccagaccgac ttcaagacgc gcgcccgtgt gcaggcggac ggcacggtga ccctgcccta  12720
tctgggcgcc gtgcaggtca agggcgagac cgcgacctcg ctcgccgaaa agctggccgg  12780
gctgctgcgc gccggcggct attatgccaa gccgatcgtc agcgtcgaaa tcgtcggttt  12840
cgtcagcaac tatgtgacgg tgctgggcca ggtgaacagt tccggcctgc agccggtcga  12900
ccgcggctat cacgtttccg agatcatcgc ccgtgccggc ggcctgcgcc ccgaagcggc  12960
cgatttcgtc gttctcaccc gcgccgatgg ctccagcgcc aagctggact acaagaagct  13020
cgcccaaggt ggccccaatg acgatccgat ggtgacgccc ggggacaagg tctttgtccc  13080
```

```
ggaagtcgag catttctaca tttatggtca aattaacgcg cctggcgtat acgcgattcg  13140
atcggacatg acgctccgtc gcgcgctggc ccagggcggt gggcttgccc ccgcaggctc  13200
cgtcaagcgt gtgaaggtca cgcgggatgg caatgaactc aagttgaagc tggacgatcc  13260
gattctccca ggcgacacga tcgtcatcgg cgaacgattg ttctgatctt ggcaacgatg  13320
gcagcggacg aggcccacca gtgaatatca ttcagttctt ccgcattctg tgggtgcgcc  13380
gatggatcat cctcccggcg tttctcgttt gcgttaccac tgccaccatt gtggtccagt  13440
ttctgcccga acgctacaag gccactacgc gggtggtgct cgacacgttt aagcccgatc  13500
ccgtcaccgg acaggtgatg agctcgcagt tcatgcgcgc ctatgtcgag actcagaccc  13560
agctgatcga ggactatgcg accgccggtc gcgtggtcga cgaactgggc tgggtgaatg  13620
atccggcgaa catctccgcg ttcaacaact cgtccgcggc tgccaccggc gacatccgcc  13680
gctggctcgc caagcagatc atcgacaata ccaaggccga tgtgatggag gggagcaaca  13740
tcctcgaaat cacctattcg gacagctcgc ccgagcgcgc cgaacgcatc gccaacctga  13800
tccgcacctc gttcctcgcc cagtcgctcg ccgccaagcg ccaggccgcg accaagtcgg  13860
ccgactggta cgcccagcag gccgaagctg cccgcgattc gctcgctgcg gcggtccagg  13920
cccgcaccga tttcgtgaag aagaccggca tcgtgctgac cgaaaccggc gccgacctgg  13980
aaacccagaa gctccagcag atcgaggggc agacgacgac cgccaccgcc ccggttgcca  14040
tggcccccag cggcatgggc ccggcgcaga tgcagctcgc ccagatcgac cagcagatcc  14100
agcaggcagc gaccagccta ggtccgaacc acccaacttt ccaggccttg cagcggcagc  14160
gcgaagtgtt cgccaaggca gcggcggcgg aacgcgcgca ggcgaacggc gtatccggtc  14220
cggcacgcgg ggccatcgaa agcgcagcca acgcccagcg cgcgcgggtt ctcggcaatc  14280
gtcaggatgt cgacaagctt acgcagctgc agcgtgacgt ctcgctgaag caggatcagt  14340
acatgaaggc ggcacagcgc gtcgccgatc tgcggctgga agcaagcagc aacgatgtcg  14400
gcatgtcgac gctcagcgaa gcatcggcgc cggaaacgcc ctattacccc aaggtgccgc  14460
tcatcatcgg tggtgcagcc ggcttcggcc tcgggctcgg tctgctggtc gcgctgctcg  14520
tcgagctgct cggccgccgc gtccgcagcc ccgaggatct ggaagttgcg atcgatgcac  14580
cggtgctggg cgtgatccag agccgcgcct cgcttgccgc ccgccttcgc cgcgcccaag  14640
aaaccctcgg cgaaggtgcc gacacgcacg gagcttcagt aaactgatgg acgcgatgac  14700
cagcgaaccg ctgcccgaag gcgatcgtcc gagcgccgtg ccgaccacgc cggatacgat  14760
cggcatgctc gaataccagc tcgtcctctc cgatccgacc gggatcgagg cggaagcgat  14820
ccgcgcgcta cgcacgcgca tcatgaccca gcacctccgc gagggccggc gcgcgctcgc  14880
gatctgcgcc gcctcggcgg gatccggctg cagcttcacc gccgtcaatc tggcgacggc  14940
gctggcgcag atcggcgtta agactgcgct ggtcgatgcc aatctgcgcg atcccagcat  15000
cggcgcagcc ttcggcctcg ccgccgacaa gcccggcctg gccgattatc tcgcctcggg  15060
cgatgtcgac ctcgcctcga tcatccatgc gacccgcctc gaccagctct cgatcatccc  15120
ggccgggcat gtcgagcaca gcccgcagga actgctcgcg tccgaacagt tccatgatct  15180
ggcgacgcag ctgctgcgcg agttcgacat cacgatcttc gacaccacgg cgtccaacac  15240
ctgcgccgac gcgcagcgtg tcgcgcatat cgccggctat gcgatcatcg tggcgcgcaa  15300
ggatgcgagc tacatccgcg acgtgaacac gctcagccgc acgctgcgtg cagaccgcac  15360
caacgtcatc ggctgcgtac tgaacggcta ttgatttgga ccatatggca gcgaccgcga  15420
tgacgcggca gcaggagagg aagggcggtg gctattggct ggccgttgcc ggtcttgccg  15480
```

```
cgctaaccat cccgaccttc atcaccctgg gtcgcgaggt ttggagtgcg gaaggcggcg  15540
tgcagggtcc gatcgtgctc gccacgggcg cctggatgct ggcccgccag tgctcgacga  15600
tcgaggcgct acgccgcccc ggcagcgtgc tgctcggcgc gctgttcctg ctggcgacgc  15660
ttgccttcta caccgttgga cgggtgttcg acttcatcag tgtcgaaacc ttcggactgg  15720
tcgcgaccta tctggtcgtc gcctatctct atttcggtgc cagggtgctc cgtgccgcct  15780
ggttcccggt gctgtggctg ttcttcctgg tgccgccgcc cggctgggcc gtcgaccgca  15840
tcaccgcacc gctcaaggag ttcgtctcct atgcggcaac gggcctgctt tcctgggtgg  15900
attatccgat cctgcgccag ggcgtgacac tgttcgtcgg cccctatcag ctgctcgtcg  15960
aagatgcctg ttcgggtctg cgctcgctgt ccagcctggt cgtcgtgacg ctgctctaca  16020
tctacatcaa gaacaagccg tcctggcgct acgcggcgtt catcgcagcg ctggtgatcc  16080
cggtggcagt ggtgaccaac gtcctgcgga tcatcatcct ggtactgatc acctatcatc  16140
tgggcgacga ggcggcgcag agcttcctcc acgtctccac cggcatggtg atgttcgtgg  16200
tcgccctgct ttgcatcttc gcgatcgact gggtggtcga gcaacttctt ctcctgcgtc  16260
ggaggcatca tgttcaaccg gcgtgacctg ctgatcggcg caggctgctt cgccgccgct  16320
ggcgcctcgc tcggcctgaa gccgcaccgg cggatggacc tgctgggcgg caccaagctc  16380
gacacgctga tgcccaaggc attcggcgca tggaaggcag aggataccgg ttcgctgatc  16440
gcgccggcgc gcgaaggcag cctggaggac aagctctaca accaggtggt cacccgcgcc  16500
ttctcccgcg cggacggtgc ccaagtgatg ctgctgatcg cctatggcaa cgcccagacc  16560
gatctactgc agctgcaccg gccggaaata tgctacccgt tcttcggctt caccgtggtg  16620
gaaagccatg agcagaccat cccggtgacg ccgcaggtga cgatccccgg tcgcgcgctg  16680
accgccacca acttcaaccg caccgagcag atcctctact ggacccgcgt cggcgaatat  16740
ctgccgcaga acggcaatca gcagatgctc gcgcggctga agagccaggt ccagggctgg  16800
atcgtcgacg gtgtgctggt gcgcatctcg acggtgacgc ccgaggcgga agatggcctg  16860
agcgccaatc tcgatttcgc gcgcgagctg gtgaagacgc tcgacccgcg cgtgctgcgc  16920
ccgctgctcg ggaacgggct cacacggcag ctcggtcacc aggtctgaac cggtgcgccg  16980
cacgcggcgc ccccggcaac aaaaaaggag cggcgcgggc cgccgccgct ccctctcctt  17040
ctcatgcggc gccctgccct caccgctcgt gcagcgcgtc actccccgtc tcgagcacgg  17100
gccccaccag atagctgaac agggttcgct tgccggtgac gatgtccgcg ctcgcgagca  17160
tccccggccg cagcggcacc tgtgcgccat gggccagcac atacccgcgc gccagcgcga  17220
tccgcgcctt gtagaccggc ggctggttct ccttcatctg caccgcctcg ggctgatgc  17280
ccgccaccgt gccgggaatc atgccgtagc gggtataggg aaaggcctgc agcttcacct  17340
ttaccggcat gccgatgtgg acgaagccga tgtcgctgtt gtcgaccatc acctcggcct  17400
cgagccgggc attgtcggga accaggctga ggagcggctt ggccccttcc accacgccgc  17460
cttcggtgtg gacctgcagc tgcgagacgg taccgctcac cggcgcgcgc agttcgcgga  17520
acgagctgcg cagattcgcc ttggcgacgt cctcgccgcg ggcacgcacc tcgtcctgcg  17580
ccttgaccag atcctgcagc acctgcgccc gcgcctcctc gcgcgtcttg gccgacaggc  17640
tggagacgct cagcgactgc tggccgagtt tggcgagcgt agcgcgcgcc gccgtcaggt  17700
cctgccgctc ggcgatcagc tggcgacgca tctccacgac gcgcagcttc gagacatagc  17760
ccttggcggc catcgtctcg ttcgcggcga tctgctgttc gagcagcggc agcgactgtt  17820
```

```
cgagcttccg cacctgtgcc tgcgcctcgg ccgcggccga gacggcggca ccgcgatcgg  17880
agcggccgcc ggccagcgcc gcctcgatct ggcccagccg ggcgcgggcg aggccgcgat  17940
gcgtcgccac ttcgcccggg ctggcggcgg caggcgcgac gaagcggaag cccctgccgt  18000
ccagcgcgtc gatgatcgcc tggttgcgtg cggcgtcgag ctgggcgctg agcagcgcca  18060
ccttcgcctg tgccgcctcc gccgacgaca cggtcgggtc gagcgtgatc agcacctggc  18120
ccttggcgac cttctgcccc tcgcccacca ggatgcggcg gacgatcccc gattcgggcg  18180
actggacgat cttggtctcg ccgatcggcg cgatccgccc ctgcgtcggc gcgacgactt  18240
cgaccttgcc gatcgccagc caggcggcgg tgatcgccag cccggccagc atcaccttgg  18300
cggtaagccg cgcggtgggc gaaaccggcc gctcgatgat ctccagcgcg gcaggcagga  18360
aggcggtgtc ataagcgtcg acgcgggcag gcagcacggt atcgcgcatg cgggcgagcg  18420
ggccgccgcg gcgcatcgga acaacggcgt tcatgcggca atctccccat agccgccctg  18480
gcggcggtgc aggtcggcat agcggccgcc caggcgcaac aattcgtcgt gtcggccgct  18540
ctcgacgatg cggccctgtt cgagcgtgat gatccggtcg cagctgcgca ccgcgctcag  18600
gcgatgcgcg atcaccacga gcgtgcggcc ggccgagatg gcgcgcaggt tgttctggat  18660
cagctcctcg ctctcggcat cgagcgccga ggtcgcttcg tcgaacacca ggatgcgcgg  18720
attgccgacg agcgcgcggg cgatggcgag ccgctggcgc tggccgccgg agagattgac  18780
gccgcgctcg acgatctcgg tgtcatagcc gcgcggctgg cgcaggatga aatcatgcgc  18840
gccggccagc gtcgccgccg cgacgacatt ctcgaacggc atggcggggt tggagagcgc  18900
gatgttctcg cggatcgagc ggctgaacag cagattctcc tgcagcacga cgccgatctg  18960
gcgacgcagc caggcgggat cgagctgcgc cacgtcgacc tcgtcgacca gcacgcggcc  19020
gagattcggc aggttgagcc gctggagcag cttggccagc gtcgacttgc ccgagcccga  19080
cgaaccgacg atgccgagcg aggtgcccgc cggaatgtcg agcgtgatgt cgctcagcac  19140
cggcggctgg tcctcggcat agcggaagct gacattctcg aagcgaatcg caccgcgcag  19200
caccggcagc gtcgccgccg aggccgggcg cggttccacc ggatggttga gcacgtcgcc  19260
cagccgctcg accgagatgc gcacctgctg gaaatcctgc cacagctgcg ccatgcggat  19320
caccggcccg gacacgcgct gggcgaacat gttgaacgcc accagcgcgc ctacgctcat  19380
cgcgccgccg atcaccgcct tggcgccgaa gaacaggatc gccgcgaagc tcagcttcga  19440
gatcagctcg atcgcctggc tgccggtgtt ggcggtattg atcagccgct gcgacgcggc  19500
ggtatgggcg gcgagctggc gctcccagcg attctgccag tgcggctcga ccgcggtcgc  19560
cttgatcgtg tggatgcccg agacgctctc gacgagcagc gcgttgctgg cggagctctt  19620
ctcgaacttg tcctccaccc gcgcgcggag cggcccggcg acgctgaacg atacgatcgc  19680
ataggcgatc agcgacacga gcacgatgcc cgagagcatc ggcgagtaga acagcatcgc  19740
ggcgaggaac acgaaggtga acagcgggtc caccatcacc gtcagcgagg cgctggtaag  19800
gaattcgcgg atcgtctcga gctggcggac gcgggtgacg gtgtcgccca cgcggcgctt  19860
ctcgaaatag gcgagcggca gcgccagcag gtggtggaac agccgggcac ccagctcgac  19920
gtcgatcttc tgcgtcgtct cggtgaacag gcgggtgcgg atccagccga gcgccacttc  19980
ccacaccgaa accgccagga aggcgaaggc gagcacgctc agcgtgctca tgctgttgtg  20040
gatcagcacc ttgtcgatca cgctctggaa caacagcggc gcggcgaggc cgagcaggtt  20100
gagcgcgagg gtgatgccga gcacctcgag gaacagcgtg cgatagcgcc ggaactgcgc  20160
ggtgaaccag gagaggccga accgcagcgg ccgtcccgcc accgcgcggg tggtgagcag  20220
```

```
caccagcgcg ccggaccaga tcgcgtccag cgcgtcccgg tcgacctgtt ccggggcatg  20280
gcccgggcgc tggatgatca cgccatgttc ggtcaggccg ccgatcacga accagccttc  20340
gggcccgtcg gcgatcgcgg gcagcggctg gcgggcgagt ccgccgcgcg gcacctcgac  20400
ggccttggcg cgcacgccct gctggcgctt ggccaggagg atcaggtcgt cggcgcttgc  20460
cgcctcggca tggcccagcg cgtggcgcag ctgttcgggc gtgatggcga tgttgtgcgc  20520
gccgagcagc agcgacaacg ccaccagtcc ggattcgcgc agctccgcct cgcgctccgc  20580
cgccccatgg gccgcgagcg cgctctgcag ggtggcctgc atttcgtcgc gtgtcatttc  20640
cggaactctg cctccatggc gatactgaga gcgccatgat gaagaaggct ggtaaagact  20700
cacttaatcc tagcttttct ggtatttacc cgtagctgcc gacccgattt gggacaggcc  20760
tggcttagca ggtccttaaa ctcgaccgac tataccgcga cgccgaggag ggggaggatt  20820
ggcgccgcat cgcgcggcga aacgcgggtg cgtcgcaaca tttcgccgga gtcgatccgt  20880
cgcgaatgct gcacccgcga acgcaatgac ggccgccacg caatccggct tgatcccggg  20940
cggcggatcg cgataagccg cgccacggtc gccaaaactc gtcgaaataa ccgacaaaac  21000
cacggcatat ggctggatat tgcagcgttt gccctgcgtt tccgtcgttc aaccgccctt  21060
cgaatcaggc aggcccagcg tgaccatgat tgatcttcct cttggaacgg cacactttgg  21120
tcgacacgga gacttccggt cgggcaattg tcccgttata gtgcaatgca acaggccgaa  21180
tcggccgctg tcggcgtgca cattccgttg agggagcccg atgaggcaat gaacgctttc  21240
gaagcacagc gcgcctttga ggagcaactt cgggcgcatt cccgggttac gccatctgcc  21300
gctcccgtgt ggcgtcgctc gacgctgcgg atggtcctct ataccgagtt gctgctgctg  21360
gacagtctct cgatcctggc cggattccac gtcgcggcgg gcacgcgcga cggcaactgg  21420
ctgtcgctgg cgggcatcaa cgtcggcgtc ttcctgctgc cgatcgctct cggcaccgcg  21480
ctcgcaagcg gcacctactc gctgaactgc ctgcgctacc cggtcagcgg cgtgaagagc  21540
atcttctcgg cattcttctt ctcgatcttc gtcgtcctgc tcggcagcta cctgctgacg  21600
gccgagctgc cgctgtcccg cgtgcagctg gcggagggcg cgatcctctc gctggtcctc  21660
ctgatggtgg gccgcctgat gttccgccgc cacgtccgcg cggttaccgg cggcaggctg  21720
ctcgacgaac tggtcatcat cgacggcgtc tcgctcgacg tcgcgggcaa tgcggtcgcg  21780
ctcgacgcgc ggatcatcaa tctctcgccg aacccgcgcg atccgcaaat gctgcatcgc  21840
ctgggcacca ccgtgatcgg gttcgaccgg gtgatcgtcg cctgcaccaa ggagcatcgc  21900
gcggtctggg cgctgctgct caagggcatg aacatcaagg gcgagatcct cgtcccccag  21960
ttcaatgcgc tgggcgcgat cggcgtggac gcctttgacg ggaaggatac gctggtcgtc  22020
tcgcagggcc cgctcaacat gcccaaccgc gcgaagaagc gcgcgctcga tctcgcgatc  22080
accgtaccgg ccgtgctcgc gctggcgccg ctgatgatcc tggtggcgat cctgatcaag  22140
ctggagagcc cgggcccggt gttgttcgcg caggatcgcg tcggccgcgg caaccggctg  22200
ttcaagatca tgaagttccg ctcgatgcgc gtaacgctgt gcgacgcgaa cggcaacgtc  22260
tcggccagcc gcgacgacga tcgcatcacc aaggtcggcc gcttcatccg caagaccagc  22320
atcgacgaac tgccgcagct gctgaacgtg ctgcgcggcg acatgagcgt cgtcggcccg  22380
cggccgcatg cgctgggctc gcgcgccgcc gatcacctgt tctgggaaat cgacgagcgc  22440
tactggcacc gccacacgct caagccgggc atgaccggtc tggcccaggt gcgcggtttc  22500
cgcggggcga ccgatcgccg cgtcgatctg accaaccggc tccaggcaga catggaatat  22560
```

```
atcgacggat gggatatctg gcgcgatatc acgatcctgt tcaagacgct gcgggtgatc  22620
gtgcattcga acgcattctg atccgcgcac gacgctgggc cgcagcctcg atccgcaaat  22680
ggattgacag cggcccggct tccgttttct cgtttgattt tcgttgcggc cggtccgcgc  22740
catgggggat tactgaatga agggcatcat ccttgcgggg ggcagcggga cgcgcctgta  22800
ccccgcaacg ctatcgatct cgaagcagct gcttcccgtc tatgacaagc cgatgatctt  22860
ctatccgctg tcggtgctga tgctcaccgg catccgggac atcctgatta tctccacccc  22920
gcgcgacctg ccgatgttcc aggcgctgct gggcgacggc tcggccttcg gcatcaacct  22980
cagctatgcc gagcagccct cccccaacgg gctggccgaa gcgttcatca tcggcgcgga  23040
tttcgtcggc aacgatccca gcgcgctgat cctgggcgac aacatctatc acggcgaaaa  23100
gatgggcgag cgctgccagg cagccgcagc gcaggcagcg cagggcggtg caaacgtctt  23160
cgcctatcat gtcgacgacc ccgagcgcta cggcgtggtc gcgttcgacc cggagacggg  23220
cgtcgccacc agcgtcgagg aaaagccggc cgagcccaag tccaactggg cgatcaccgg  23280
cctgtatttc tacgacaagg acgtggtcga catcgccaag tcgatccagc cctcggcgcg  23340
cggcgaactc gagatcaccg acgtcaaccg cgtttacatg gagcgcggcg acctgcacat  23400
cacgcgcctc ggccgcggct atgcctggct cgacaccggc acgcatgaca gcctgcacga  23460
agccggctcg ttcgttcgca cgctcgagca tcggacgggc gtgaagatcg cctgcccgga  23520
ggaaatcgcc ttcgaaagcg gctggctcgg cgccgaagac ctgctcaagc gcgccgccgg  23580
cctcggcaag accggctatg ccgcctatct ccgcaaggtt gcgaccgcag catgacccag  23640
gtccatcatc acgaactgtc cggcgtcatc gagttcacgc cgcccaaata tggcgaccac  23700
cgcggcttct tctccgaagt gttcaagcag tcggtgctcg atgccgaagg cgtcgaggca  23760
cgctgggtgc aggacaatca gagcttctcg gcggccccgg gcacgatccg cggcctgcat  23820
ctccaggcgc cgcccttcgc ccaggccaag ctggtccgcg tgttgcgcgg cgcgatcttc  23880
gacgtcgcgg tcgacatccg tcgcggctcg cccacctatg gcaaatgggt cggcgtcgag  23940
ctctcggccg agaagtggaa ccagctgctg gtccccgccg gctatgcgca cggcttcatg  24000
acgctcgttc cggattgcga gatcctctac aaggtcagcg ccaaatattc gaaggattcg  24060
gagatggcga tccgttggga cgatcccgat ctcgccatcg cctggccgga catcggcgtc  24120
gagccggtcc tctccgaaaa ggacgcggtc gccacgccct tcgccgaatt caacaccccc  24180
ttcttctatc agggctgagc catgcagcag accttcctcg tcaccggcgg cgccggcttc  24240
atcggctcgg cggtggtgcg ccacctcgtc cgccagggcg cgcgcgtcat caatctcgac  24300
aagctcacct atgccggcaa cccggcctcg ctgactgcga tcgagaacgc gcccaactat  24360
cgcttcgtcc atgccgacat cgccgacacc gcgacgatcc taccgctgct gcgcgaggag  24420
caggtcgatg tggtgatgca cctcgccgcc gagagccatg tcgatcgctc gatcgacggc  24480
cctggcgagt tcatcgagac caatgtcgtc ggcaccttca agctgctcca gtcggcgctg  24540
caatattggc gcgagctgga gggcgagaaa cgcgacgcgt tccgcttcca ccacatctcc  24600
accgacgaag tgttcggcga cctgccgttc gacagcggca tcttcaccga agagacgccc  24660
tatgatccct cctcgcccta ttcggcgtcg aaggcggcga gcgaccatct ggtgcgcgcc  24720
tggggccaca cctatggcct gccggtggtg ctgtcgaact gctcgaacaa ttacgggccg  24780
ttccacttcc ccgagaagct gatcccgttg accatcctca acgcgctcga gggcaagccg  24840
ctgccggtct acggcaaggg cgagaatatc cgcgactggc tgtatgtcga cgatcacgcc  24900
aaggcgctgg cgaccatcgc caccaccggc aaggtcggcc agagctacaa tgtcggcggc  24960
```

```
cgcaacgagc ggaccaacct gcaggtggtc gagacgatct gcgacctgct cgaccagcgc  25020

attccgctgg ccgacggtcg caagcgccgc gaactgatca ccttcgtcac cgatcgcccc  25080

ggccatgacc gccgctacgc gatcgacgcg accaagctcg agaccgagct gggctggaag  25140

gctgaggaga atttcgacac cggcatcgcc gcgacgatcg actggtatct ggcgaacgag  25200

tggtggtggg gcccgatccg ctccggcaaa tatgccggcg agcggctggg gcagaccgcc  25260

tgatgcgtat cctcgtcacc gggcatgacg gccaggtcgc ccagtcgctg gccgagcagg  25320

cggtgggcca cgagctggtc ttcaccacct accccgaatt cgatctctcc aagccggaga  25380

cgatcgaggc cggtgtggcg cgggtgcacc cggacctgat cgtctccgcc gccgcctaca  25440

cggcggtcga caaggcggaa agcgaacccg agctggcgat ggcgatcaac ggcgacggtc  25500

ccggcgtgct ggcgcgcgcg ggcgcgaaga tcggcgcgcc gatcatccac ctgtcgaccg  25560

attatgtgtt cgacggcagt ctcgaccgcc cttggcgcga ggacgatccc accggcccgc  25620

tcggcgtcta tggcgcgacc aagctggccg gcgagcaggc ggtgcaggcc tcgggtgcca  25680

ccaacgccgt gatccggctg gcctgggtct acagcccgtt cggcaacaat ttcgtcaaga  25740

cgatgctccg cctcgccgag acgcgcgacg cgctgaacgt cgtggaggac cagtggggct  25800

gccccagttc ggcgctggac atcgcgaccg cgatcctgac ggtggtcggg cactggcagc  25860

aggacggcgc gacgagcggc ctctaccatt tcgccggcac cggcgagacc aactgggccg  25920

acttcgcatc gacgatcttc gccgagagcg ccaagcgcgg tggcccctcg gccaccgtca  25980

ccggcattcc cagctcgggc tatccgactc cggccacgcg cccggccaat tcgcggctgg  26040

actgcacccg cttcgcggag accttcggct accgggcgcc tgcctggcag gattcgctga  26100

acgtcgtact ggatcgcctg ctcggctgat ccgaaacggg gggcctcagc gccccccgcc  26160

atgctcccgt tcgcgcgccg gcaatgcctc tagcaccgcg cgctttccct taggactcag  26220

ctcgctccag ccggcgattt ccttgggcga ccgccagcac cccaggcaca gccggatc    26278
```

```
<210> SEQ ID NO 2
<211> LENGTH: 1053
<212> TYPE: DNA
<213> ORGANISM: Sphingomonas sp. ATCC53159
<220> FEATURE:
<221> NAME/KEY: CDS
<222> LOCATION: (1)..(1053)

<400> SEQUENCE: 2

atc aac ggc gcc ttg ctc gga cgg cac aaa ttc gtc ctg gtc aat gtg       48
Ile Asn Gly Ala Leu Leu Gly Arg His Lys Phe Val Leu Val Asn Val
1               5                   10                  15

tcc acg gtc gcc tct tcg ata ctg ttc cag ctg ttc ccg ctt gtc gtc       96
Ser Thr Val Ala Ser Ser Ile Leu Phe Gln Leu Phe Pro Leu Val Val
            20                  25                  30

gcc tgg atg atc ggc ccg gac ctg cga acg ctg ctg atc gcc gcg ctc      144
Ala Trp Met Ile Gly Pro Asp Leu Arg Thr Leu Leu Ile Ala Ala Leu
        35                  40                  45

gtt ggc cgg gcg gtt ccg atg atc ggc atg ctg ccc gcg ctg tat cga      192
Val Gly Arg Ala Val Pro Met Ile Gly Met Leu Pro Ala Leu Tyr Arg
    50                  55                  60

aac ctt ttg cgc ggc aac acg ccg cgt ttt cac gcc agc gag gcg cgc      240
Asn Leu Leu Arg Gly Asn Thr Pro Arg Phe His Ala Ser Glu Ala Arg
65                  70                  75                  80

ttc ctg ata ggc tat ggc ggg tgg gcc tcg ctc acg acc gtg gta gcg      288
Phe Leu Ile Gly Tyr Gly Gly Trp Ala Ser Leu Thr Thr Val Val Ala
                85                  90                  95
```

```
acc gtg ctc atg atg gcg gac cgc ttc ctg att ggc gca ctt ctt ggg      336
Thr Val Leu Met Met Ala Asp Arg Phe Leu Ile Gly Ala Leu Leu Gly
            100                 105                 110

ccc gtc gcc gtg acc atc tac acg gcc ccc ctg caa ctc gca cag cgc      384
Pro Val Ala Val Thr Ile Tyr Thr Ala Pro Leu Gln Leu Ala Gln Arg
        115                 120                 125

gta tcg ctg ctg ccc tcc gca ctg tcc gcc gcg ctg ttc ccg cgc ctg      432
Val Ser Leu Leu Pro Ser Ala Leu Ser Ala Ala Leu Phe Pro Arg Leu
    130                 135                 140

ccc agc gcg acg ccg gcg gag cgc atg gcg ctt cag atc cgc tcg ctg      480
Pro Ser Ala Thr Pro Ala Glu Arg Met Ala Leu Gln Ile Arg Ser Leu
145                 150                 155                 160

tcg ctg atc atg ggc ggc ctt acc ggg atg atc ggc ggc gga cta ttg      528
Ser Leu Ile Met Gly Gly Leu Thr Gly Met Ile Gly Gly Gly Leu Leu
                165                 170                 175

ctg gcc gcg ccg ttt ctc gat ctc tgg atc ggc aag tcg ctc ggc cat      576
Leu Ala Ala Pro Phe Leu Asp Leu Trp Ile Gly Lys Ser Leu Gly His
            180                 185                 190

gcg gga acg ccg gtc gcg ctc ttc ctg ttc ttc ggc gca tgg tgg aat      624
Ala Gly Thr Pro Val Ala Leu Phe Leu Phe Phe Gly Ala Trp Trp Asn
        195                 200                 205

gcg ctg gcg atc att tcg ttc agc ggc ctg cag gcg agc gga cgg ccg      672
Ala Leu Ala Ile Ile Ser Phe Ser Gly Leu Gln Ala Ser Gly Arg Pro
    210                 215                 220

aaa gcg agc gcg atc gtc cag ggg gca gag ctg cta ccc gtg ttg atc      720
Lys Ala Ser Ala Ile Val Gln Gly Ala Glu Leu Leu Pro Val Leu Ile
225                 230                 235                 240

gcg ctg tat gca ggg atc cga tgg ggc ggc gtg acc ggc gcc gca gcg      768
Ala Leu Tyr Ala Gly Ile Arg Trp Gly Gly Val Thr Gly Ala Ala Ala
                245                 250                 255

gtc ttt ctg gga cgc tcc gcc ctg gat ttc gtc ctg ttg acc tgg cag      816
Val Phe Leu Gly Arg Ser Ala Leu Asp Phe Val Leu Leu Thr Trp Gln
            260                 265                 270

gca ggc ctg ctc cgc cag acg gtg aag caa gta tcc gta tgc ggc gcc      864
Ala Gly Leu Leu Arg Gln Thr Val Lys Gln Val Ser Val Cys Gly Ala
        275                 280                 285

gtt ctc acc gtc gcg atg ctc gtg ggc gcg acc tat cgc tat tcg gtg      912
Val Leu Thr Val Ala Met Leu Val Gly Ala Thr Tyr Arg Tyr Ser Val
    290                 295                 300

ccg ctc tgg tgc gta ctc agc gcc tgc tgc ctg gtc gcg ctg gca gcc      960
Pro Leu Trp Cys Val Leu Ser Ala Cys Cys Leu Val Ala Leu Ala Ala
305                 310                 315                 320

tgc tcc tgg tgg aca ttg gcg cgc cag gac aag gca ctg ctg att gga     1008
Cys Ser Trp Trp Thr Leu Ala Arg Gln Asp Lys Ala Leu Leu Ile Gly
                325                 330                 335

cga ttg agc cga att cta cca aag cag cgg caa ctc gac cta tag         1053
Arg Leu Ser Arg Ile Leu Pro Lys Gln Arg Gln Leu Asp Leu
            340                 345                 350


<210> SEQ ID NO 3
<211> LENGTH: 350
<212> TYPE: PRT
<213> ORGANISM: Sphingomonas sp. ATCC53159

<400> SEQUENCE: 3

Ile Asn Gly Ala Leu Leu Gly Arg His Lys Phe Val Leu Val Asn Val
1               5                   10                  15

Ser Thr Val Ala Ser Ser Ile Leu Phe Gln Leu Phe Pro Leu Val Val
            20                  25                  30
```

```
Ala Trp Met Ile Gly Pro Asp Leu Arg Thr Leu Leu Ile Ala Ala Leu
        35                  40                  45

Val Gly Arg Ala Val Pro Met Ile Gly Met Leu Pro Ala Leu Tyr Arg
    50                  55                  60

Asn Leu Leu Arg Gly Asn Thr Pro Arg Phe His Ala Ser Glu Ala Arg
65                  70                  75                  80

Phe Leu Ile Gly Tyr Gly Gly Trp Ala Ser Leu Thr Thr Val Val Ala
                85                  90                  95

Thr Val Leu Met Met Ala Asp Arg Phe Leu Ile Gly Ala Leu Leu Gly
            100                 105                 110

Pro Val Ala Val Thr Ile Tyr Thr Ala Pro Leu Gln Leu Ala Gln Arg
        115                 120                 125

Val Ser Leu Leu Pro Ser Ala Leu Ser Ala Ala Leu Phe Pro Arg Leu
    130                 135                 140

Pro Ser Ala Thr Pro Ala Glu Arg Met Ala Leu Gln Ile Arg Ser Leu
145                 150                 155                 160

Ser Leu Ile Met Gly Gly Leu Thr Gly Met Ile Gly Gly Gly Leu Leu
                165                 170                 175

Leu Ala Ala Pro Phe Leu Asp Leu Trp Ile Gly Lys Ser Leu Gly His
            180                 185                 190

Ala Gly Thr Pro Val Ala Leu Phe Leu Phe Phe Gly Ala Trp Trp Asn
        195                 200                 205

Ala Leu Ala Ile Ile Ser Phe Ser Gly Leu Gln Ala Ser Gly Arg Pro
    210                 215                 220

Lys Ala Ser Ala Ile Val Gln Gly Ala Glu Leu Leu Pro Val Leu Ile
225                 230                 235                 240

Ala Leu Tyr Ala Gly Ile Arg Trp Gly Gly Val Thr Gly Ala Ala Ala
                245                 250                 255

Val Phe Leu Gly Arg Ser Ala Leu Asp Phe Val Leu Leu Thr Trp Gln
            260                 265                 270

Ala Gly Leu Leu Arg Gln Thr Val Lys Gln Val Ser Val Cys Gly Ala
        275                 280                 285

Val Leu Thr Val Ala Met Leu Val Gly Ala Thr Tyr Arg Tyr Ser Val
    290                 295                 300

Pro Leu Trp Cys Val Leu Ser Ala Cys Cys Leu Val Ala Leu Ala Ala
305                 310                 315                 320

Cys Ser Trp Trp Thr Leu Ala Arg Gln Asp Lys Ala Leu Leu Ile Gly
                325                 330                 335

Arg Leu Ser Arg Ile Leu Pro Lys Gln Arg Gln Leu Asp Leu
            340                 345                 350
```

<210> SEQ ID NO 4
<211> LENGTH: 1626
<212> TYPE: DNA
<213> ORGANISM: Sphingomonas sp. ATCC53159
<220> FEATURE:
<221> NAME/KEY: CDS
<222> LOCATION: (1)..(1626)

<400> SEQUENCE: 4

```
atg acg act acc tcg gcg ttt cgt cgc ccg gcc ttc cac gga gcg atg       48
Met Thr Thr Thr Ser Ala Phe Arg Arg Pro Ala Phe His Gly Ala Met
1               5                   10                  15

cag cgg ctt cgc agg ttg cga ctg gtt cgg ttt ctg aca aag cca gcg       96
Gln Arg Leu Arg Arg Leu Arg Leu Val Arg Phe Leu Thr Lys Pro Ala
            20                  25                  30
```

-continued

```
atc ccg gta ctg ccc gtc tac aaa gcc gag cga tca ggc gtg acg atc      144
Ile Pro Val Leu Pro Val Tyr Lys Ala Glu Arg Ser Gly Val Thr Ile
        35                  40                  45

gcg gcg cgg cgt acc gtt ctg ctg gtc agc gtg atg ttt ctt gcc gca      192
Ala Ala Arg Arg Thr Val Leu Leu Val Ser Val Met Phe Leu Ala Ala
    50                  55                  60

gtc tac ggc ctg ctc gcc gca gtt ctg ccg ctc cag atg ctg gcg atc      240
Val Tyr Gly Leu Leu Ala Ala Val Leu Pro Leu Gln Met Leu Ala Ile
65                  70                  75                  80

ccg gcc gtg ccc ctc gtt ctg atg gcg ctc gta gtg atc tgg gcg cta      288
Pro Ala Val Pro Leu Val Leu Met Ala Leu Val Val Ile Trp Ala Leu
                85                  90                  95

ccc gag gcg cgg cag gcg cct act cgc ctg ctg gca aaa cta tac ctc      336
Pro Glu Ala Arg Gln Ala Pro Thr Arg Leu Leu Ala Lys Leu Tyr Leu
            100                 105                 110

gcc tat atg gtg gcg gcg ctc gtg tgg ccg aac tat ctt gcg ctc agc      384
Ala Tyr Met Val Ala Ala Leu Val Trp Pro Asn Tyr Leu Ala Leu Ser
        115                 120                 125

gtt ggt ggt ttg cct tgg atc tcg atc agg cgg atg atc ggt tcg atc      432
Val Gly Gly Leu Pro Trp Ile Ser Ile Arg Arg Met Ile Gly Ser Ile
    130                 135                 140

gca ttg ctc acg ctc atg atc tcg ctt tcg gtc tcg aaa aag ttt cga      480
Ala Leu Leu Thr Leu Met Ile Ser Leu Ser Val Ser Lys Lys Phe Arg
145                 150                 155                 160

tcc gag atg gcg gcg att atg cgg gcg gcg ccg atc cca tcg cga cta      528
Ser Glu Met Ala Ala Ile Met Arg Ala Ala Pro Ile Pro Ser Arg Leu
                165                 170                 175

ttg ctt gcc ttc att atg gtc cag atc gtc gcc tcc att gcg acc cca      576
Leu Leu Ala Phe Ile Met Val Gln Ile Val Ala Ser Ile Ala Thr Pro
            180                 185                 190

gcg gcc tcg caa aca att ccg cgg ttg att ggc atc gtt ctg acg gtg      624
Ala Ala Ser Gln Thr Ile Pro Arg Leu Ile Gly Ile Val Leu Thr Val
        195                 200                 205

acg ccg atg gca ttc atc tcg cta tgg ctg atc ggg acc gac acg cgc      672
Thr Pro Met Ala Phe Ile Ser Leu Trp Leu Ile Gly Thr Asp Thr Arg
    210                 215                 220

acc ccg gag tgg tgg gtt acg cgc ttg ttt tgg tgc gtg ggc gtg ctg      720
Thr Pro Glu Trp Trp Val Thr Arg Leu Phe Trp Cys Val Gly Val Leu
225                 230                 235                 240

atg gcg att ggc gtg ctg gag ttc cgg gtg aag cac gtc ctc tgg gcc      768
Met Ala Ile Gly Val Leu Glu Phe Arg Val Lys His Val Leu Trp Ala
                245                 250                 255

tac tcg att ccg agc ttc ctg cgc gtt gat gag cag ttt ctt acc gta      816
Tyr Ser Ile Pro Ser Phe Leu Arg Val Asp Glu Gln Phe Leu Thr Val
            260                 265                 270

gtg ctt acg ccc ggt ttc cgg ggt act tac cgc gtt ttg acg act ttc      864
Val Leu Thr Pro Gly Phe Arg Gly Thr Tyr Arg Val Leu Thr Thr Phe
        275                 280                 285

agc agt ccg ctt gtc tgg gga gag ttg acg gct ttg acg att cct ttc      912
Ser Ser Pro Leu Val Trp Gly Glu Leu Thr Ala Leu Thr Ile Pro Phe
    290                 295                 300

gtg ctg cac cgt ata gcg aat tcc cgt ggc gta ggg aga ttg gca ttt      960
Val Leu His Arg Ile Ala Asn Ser Arg Gly Val Gly Arg Leu Ala Phe
305                 310                 315                 320

tgg att ttc ttc gat ttt ctt gta gtt gcg tcc gga ttt ctt agc ggt     1008
Trp Ile Phe Phe Asp Phe Leu Val Val Ala Ser Gly Phe Leu Ser Gly
                325                 330                 335

tct cga ctg gca atg gtg ggg gga ttg gtg gcg cat acc gtg tat ttg     1056
Ser Arg Leu Ala Met Val Gly Gly Leu Val Ala His Thr Val Tyr Leu
            340                 345                 350
```

```
ctt att tgg gca att cgg cgg tgg cgg acc aca aag ggc ggg ctt gtc     1104
Leu Ile Trp Ala Ile Arg Arg Trp Arg Thr Thr Lys Gly Gly Leu Val
        355                 360                 365

ggc att tcg ctg acg ttg acg tat ccc gcc ttg atg gtg gcg ctg tcg     1152
Gly Ile Ser Leu Thr Leu Thr Tyr Pro Ala Leu Met Val Ala Leu Ser
    370                 375                 380

ctg gcg gtc atg ttc gtg cct gcc gtc cac aac cgt gtt ctc ggt gga     1200
Leu Ala Val Met Phe Val Pro Ala Val His Asn Arg Val Leu Gly Gly
385                 390                 395                 400

ggc gct tct caa ctt agc aat caa ggc agg cag gag cag ttt cgc ttg     1248
Gly Ala Ser Gln Leu Ser Asn Gln Gly Arg Gln Glu Gln Phe Arg Leu
                405                 410                 415

ggc gtg cct gcc atc gct cgc cgc cct ttc ttc ggc tat ggc ccg gga     1296
Gly Val Pro Ala Ile Ala Arg Arg Pro Phe Phe Gly Tyr Gly Pro Gly
            420                 425                 430

gag ggt gct ggc gct gtc ggg tgg cgt aat cag caa ggc ttc cta tcg     1344
Glu Gly Ala Gly Ala Val Gly Trp Arg Asn Gln Gln Gly Phe Leu Ser
        435                 440                 445

atc gac agt ggt ttc ctg tcc gta gcg gct gat tac ggc ttg ctg ggt     1392
Ile Asp Ser Gly Phe Leu Ser Val Ala Ala Asp Tyr Gly Leu Leu Gly
    450                 455                 460

ttt gtt tcg cta tac ggc acg atg att acg tta atg att ttg ctc gcg     1440
Phe Val Ser Leu Tyr Gly Thr Met Ile Thr Leu Met Ile Leu Leu Ala
465                 470                 475                 480

ttt cgt ggt ctt aag atg agc gga gat ggc tac ccg ctt gag ctc gcc     1488
Phe Arg Gly Leu Lys Met Ser Gly Asp Gly Tyr Pro Leu Glu Leu Ala
                485                 490                 495

gta gca act ttc ctg gct gtt ctt tta aat acg cgg tca gtc ctg tcg     1536
Val Ala Thr Phe Leu Ala Val Leu Leu Asn Thr Arg Ser Val Leu Ser
            500                 505                 510

caa ggt gac aat gac ccg ttc atc ttt atg acg ctg ggg cta ggc ata     1584
Gln Gly Asp Asn Asp Pro Phe Ile Phe Met Thr Leu Gly Leu Gly Ile
        515                 520                 525

gcg ctt cta tat cgc tct cgg cct gtg tct ttg tcg gtg tag             1626
Ala Leu Leu Tyr Arg Ser Arg Pro Val Ser Leu Ser Val
    530                 535                 540


<210> SEQ ID NO 5
<211> LENGTH: 541
<212> TYPE: PRT
<213> ORGANISM: Sphingomonas sp. ATCC53159

<400> SEQUENCE: 5

Met Thr Thr Thr Ser Ala Phe Arg Arg Pro Ala Phe His Gly Ala Met
1               5                   10                  15

Gln Arg Leu Arg Arg Leu Arg Leu Val Arg Phe Leu Thr Lys Pro Ala
            20                  25                  30

Ile Pro Val Leu Pro Val Tyr Lys Ala Glu Arg Ser Gly Val Thr Ile
        35                  40                  45

Ala Ala Arg Arg Thr Val Leu Leu Val Ser Val Met Phe Leu Ala Ala
    50                  55                  60

Val Tyr Gly Leu Leu Ala Ala Val Leu Pro Leu Gln Met Leu Ala Ile
65                  70                  75                  80

Pro Ala Val Pro Leu Val Leu Met Ala Leu Val Val Ile Trp Ala Leu
                85                  90                  95

Pro Glu Ala Arg Gln Ala Pro Thr Arg Leu Leu Ala Lys Leu Tyr Leu
            100                 105                 110

Ala Tyr Met Val Ala Ala Leu Val Trp Pro Asn Tyr Leu Ala Leu Ser
```

```
        115                 120                 125

Val Gly Gly Leu Pro Trp Ile Ser Ile Arg Arg Met Ile Gly Ser Ile
    130                 135                 140

Ala Leu Leu Thr Leu Met Ile Ser Leu Ser Val Ser Lys Lys Phe Arg
145                 150                 155                 160

Ser Glu Met Ala Ala Ile Met Arg Ala Ala Pro Ile Pro Ser Arg Leu
                165                 170                 175

Leu Leu Ala Phe Ile Met Val Gln Ile Val Ala Ser Ile Ala Thr Pro
            180                 185                 190

Ala Ala Ser Gln Thr Ile Pro Arg Leu Ile Gly Ile Val Leu Thr Val
        195                 200                 205

Thr Pro Met Ala Phe Ile Ser Leu Trp Leu Ile Gly Thr Asp Thr Arg
    210                 215                 220

Thr Pro Glu Trp Trp Val Thr Arg Leu Phe Trp Cys Val Gly Val Leu
225                 230                 235                 240

Met Ala Ile Gly Val Leu Glu Phe Arg Val Lys His Val Leu Trp Ala
                245                 250                 255

Tyr Ser Ile Pro Ser Phe Leu Arg Val Asp Glu Gln Phe Leu Thr Val
            260                 265                 270

Val Leu Thr Pro Gly Phe Arg Gly Thr Tyr Arg Val Leu Thr Thr Phe
        275                 280                 285

Ser Ser Pro Leu Val Trp Gly Glu Leu Thr Ala Leu Thr Ile Pro Phe
    290                 295                 300

Val Leu His Arg Ile Ala Asn Ser Arg Gly Val Gly Arg Leu Ala Phe
305                 310                 315                 320

Trp Ile Phe Phe Asp Phe Leu Val Val Ala Ser Gly Phe Leu Ser Gly
                325                 330                 335

Ser Arg Leu Ala Met Val Gly Gly Leu Val Ala His Thr Val Tyr Leu
            340                 345                 350

Leu Ile Trp Ala Ile Arg Arg Trp Arg Thr Thr Lys Gly Gly Leu Val
        355                 360                 365

Gly Ile Ser Leu Thr Leu Thr Tyr Pro Ala Leu Met Val Ala Leu Ser
    370                 375                 380

Leu Ala Val Met Phe Val Pro Ala Val His Asn Arg Val Leu Gly Gly
385                 390                 395                 400

Gly Ala Ser Gln Leu Ser Asn Gln Gly Arg Gln Glu Gln Phe Arg Leu
                405                 410                 415

Gly Val Pro Ala Ile Ala Arg Arg Pro Phe Phe Gly Tyr Gly Pro Gly
            420                 425                 430

Glu Gly Ala Gly Ala Val Gly Trp Arg Asn Gln Gln Gly Phe Leu Ser
        435                 440                 445

Ile Asp Ser Gly Phe Leu Ser Val Ala Ala Asp Tyr Gly Leu Leu Gly
    450                 455                 460

Phe Val Ser Leu Tyr Gly Thr Met Ile Thr Leu Met Ile Leu Leu Ala
465                 470                 475                 480

Phe Arg Gly Leu Lys Met Ser Gly Asp Gly Tyr Pro Leu Glu Leu Ala
                485                 490                 495

Val Ala Thr Phe Leu Ala Val Leu Leu Asn Thr Arg Ser Val Leu Ser
            500                 505                 510

Gln Gly Asp Asn Asp Pro Phe Ile Phe Met Thr Leu Gly Leu Gly Ile
        515                 520                 525

Ala Leu Leu Tyr Arg Ser Arg Pro Val Ser Leu Ser Val
    530                 535                 540
```

```
<210> SEQ ID NO 6
<211> LENGTH: 1998
<212> TYPE: DNA
<213> ORGANISM: Sphingomonas sp. ATCC53159
<220> FEATURE:
<221> NAME/KEY: CDS
<222> LOCATION: (1)..(1998)

<400> SEQUENCE: 6

atg ccg gat atc att gtc aag aat cag acg gag ttg aat gct gca atc       48
Met Pro Asp Ile Ile Val Lys Asn Gln Thr Glu Leu Asn Ala Ala Ile
1               5                   10                  15

gcg gcg gcg aag ggt ggc gaa acc atc aag ctt gcc gcc ggg gtc tac       96
Ala Ala Ala Lys Gly Gly Glu Thr Ile Lys Leu Ala Ala Gly Val Tyr
            20                  25                  30

aca gat ctc act gta atg acc aag acg ttt acc agc atg gtg aca att      144
Thr Asp Leu Thr Val Met Thr Lys Thr Phe Thr Ser Met Val Thr Ile
        35                  40                  45

gag tcg ctc gac tcg tcg aac ccg gtc aat atc caa aag ctg gtg atc      192
Glu Ser Leu Asp Ser Ser Asn Pro Val Asn Ile Gln Lys Leu Val Ile
    50                  55                  60

ggg aac agt agc aac gtt acc gtc aaa aac atg gtc gct gcg acc gat      240
Gly Asn Ser Ser Asn Val Thr Val Lys Asn Met Val Ala Ala Thr Asp
65                  70                  75                  80

tac aag ccc gcc gat gac tgg aat cga ctg aat acg atc cag ggt tcg      288
Tyr Lys Pro Ala Asp Asp Trp Asn Arg Leu Asn Thr Ile Gln Gly Ser
                85                  90                  95

gcc aac atc gtt ttg gac ggc gtg cgg ttc agc ggc ggc act ggt gac      336
Ala Asn Ile Val Leu Asp Gly Val Arg Phe Ser Gly Gly Thr Gly Asp
            100                 105                 110

cct tcg ctc tcg aag ggg gcg ggc ttg ttc gtg cgc aac agc acg tcg      384
Pro Ser Leu Ser Lys Gly Ala Gly Leu Phe Val Arg Asn Ser Thr Ser
        115                 120                 125

gtg acg atg cag aat tcg tct atc gac cac ttc ggt ctg ggc ctt gag      432
Val Thr Met Gln Asn Ser Ser Ile Asp His Phe Gly Leu Gly Leu Glu
    130                 135                 140

gcc tac aac gtc gat ggc atg gtg gtc cag aac agc agc ttc cac gac      480
Ala Tyr Asn Val Asp Gly Met Val Val Gln Asn Ser Ser Phe His Asp
145                 150                 155                 160

aac cgg cgc gat cat acg aac ttc act gag atg aac aat ctt gtc atc      528
Asn Arg Arg Asp His Thr Asn Phe Thr Glu Met Asn Asn Leu Val Ile
                165                 170                 175

gac gga aat tcg ttc acg aac ctg ttt ccc gtg ggc acc gaa cat ccc      576
Asp Gly Asn Ser Phe Thr Asn Leu Phe Pro Val Gly Thr Glu His Pro
            180                 185                 190

gac gcc att cag ttc ttc acg gcg ggc aag gtc aag ggc aat acc aac      624
Asp Ala Ile Gln Phe Phe Thr Ala Gly Lys Val Lys Gly Asn Thr Asn
        195                 200                 205

atc acc atc tcc aat aac gtc atc atg cag ggc gcg ggc tct ggc gcg      672
Ile Thr Ile Ser Asn Asn Val Ile Met Gln Gly Ala Gly Ser Gly Ala
    210                 215                 220

caa ggg att ttc atg aat gac gag gcc ggt aat ctt ccc tat gtc aat      720
Gln Gly Ile Phe Met Asn Asp Glu Ala Gly Asn Leu Pro Tyr Val Asn
225                 230                 235                 240

gta aac atc aaa aac aat ctt atc tat ctg aat ggt tat tac cac ggt      768
Val Asn Ile Lys Asn Asn Leu Ile Tyr Leu Asn Gly Tyr Tyr His Gly
                245                 250                 255

atc aac gtt gtt aac ggc gtt aat gtc aat atc gaa tcc aat agc gtg      816
Ile Asn Val Val Asn Gly Val Asn Val Asn Ile Glu Ser Asn Ser Val
            260                 265                 270
```

```
ata tcg caa gtg gat ggc aca tca ttt tgg att cgc ctc gac aaa acc      864
Ile Ser Gln Val Asp Gly Thr Ser Phe Trp Ile Arg Leu Asp Lys Thr
        275                 280                 285

aat ggc gcg acg atc aag aac aat gtt gcg gac ctg atc acc gtc aca      912
Asn Gly Ala Thr Ile Lys Asn Asn Val Ala Asp Leu Ile Thr Val Thr
    290                 295                 300

agc tcc tcg agc aat atc gtg cag aca ggc aat cgt acg ctg acg agt      960
Ser Ser Ser Ser Asn Ile Val Gln Thr Gly Asn Arg Thr Leu Thr Ser
305                 310                 315                 320

gac tcg gca acg atc cgc aag atc tat ggc ctc aac gat ggg gct acg     1008
Asp Ser Ala Thr Ile Arg Lys Ile Tyr Gly Leu Asn Asp Gly Ala Thr
                325                 330                 335

gcg cgg ctc agc gat ttg atc gtt ccc ggc gtc ggg tac cag ccg ccc     1056
Ala Arg Leu Ser Asp Leu Ile Val Pro Gly Val Gly Tyr Gln Pro Pro
            340                 345                 350

gtg tcg agc gct gct gcc gct cag gtg act acc gaa ctg tcg act gcg     1104
Val Ser Ser Ala Ala Ala Ala Gln Val Thr Thr Glu Leu Ser Thr Ala
        355                 360                 365

aag gcg gca aat ccg tcg ctg ctg ctc gat ctg tcg ttc agc aac agc     1152
Lys Ala Ala Asn Pro Ser Leu Leu Leu Asp Leu Ser Phe Ser Asn Ser
    370                 375                 380

ggc gtc gtg gac ctt tcg cac tgg aat acc ggc cag acg aca aag gcg     1200
Gly Val Val Asp Leu Ser His Trp Asn Thr Gly Gln Thr Thr Lys Ala
385                 390                 395                 400

gtg gac gtg tcg gcg gtc gtg ggc agc gcc ttc cac gtc tcg acg ggc     1248
Val Asp Val Ser Ala Val Val Gly Ser Ala Phe His Val Ser Thr Gly
                405                 410                 415

acg ggg gtg gaa cta aac cgg agc tat tcg cgg cag att tac gca ttg     1296
Thr Gly Val Glu Leu Asn Arg Ser Tyr Ser Arg Gln Ile Tyr Ala Leu
            420                 425                 430

tcg gcg ttc acg ctc agc ttc gac ctc aag cgg gac tcg gct acg gcc     1344
Ser Ala Phe Thr Leu Ser Phe Asp Leu Lys Arg Asp Ser Ala Thr Ala
        435                 440                 445

acg gcc ggg caa att ctt ggc atc ttc cag agc tgg tcg gtt tcg ctg     1392
Thr Ala Gly Gln Ile Leu Gly Ile Phe Gln Ser Trp Ser Val Ser Leu
    450                 455                 460

cag gcc aat ggg gaa ctg agc ttc acc atg cgc aac gcc gcg ggc gtc     1440
Gln Ala Asn Gly Glu Leu Ser Phe Thr Met Arg Asn Ala Ala Gly Val
465                 470                 475                 480

agc cag aca atg gtg acg agc ggc gcc aag ctg ctt gat gct gcc aca     1488
Ser Gln Thr Met Val Thr Ser Gly Ala Lys Leu Leu Asp Ala Ala Thr
                485                 490                 495

cac aag atc gcc ctg acc tac gac agc acg cgg aaa acc gcg att ctg     1536
His Lys Ile Ala Leu Thr Tyr Asp Ser Thr Arg Lys Thr Ala Ile Leu
            500                 505                 510

tac gta gac ggc atg caa cgc ggc aca gcg acg atg acc ggc acg acc     1584
Tyr Val Asp Gly Met Gln Arg Gly Thr Ala Thr Met Thr Gly Thr Thr
        515                 520                 525

cgg ccc gcc gaa tcc tgg ggg ctg tat gtc ggc agc ccg ttc tcg acc     1632
Arg Pro Ala Glu Ser Trp Gly Leu Tyr Val Gly Ser Pro Phe Ser Thr
    530                 535                 540

gca ttc agc gga acg gtc ggc gac atc gag atc cgc gat ggc gcg atc     1680
Ala Phe Ser Gly Thr Val Gly Asp Ile Glu Ile Arg Asp Gly Ala Ile
545                 550                 555                 560

agc gcc gcc cag gtg cag gcg ctg gtg acc gcg tcg agc gcc agc gcg     1728
Ser Ala Ala Gln Val Gln Ala Leu Val Thr Ala Ser Ser Ala Ser Ala
                565                 570                 575

gcg gcg acg gtc aag gac agc ctc gtc acc ggc gcg gcc gcg cag gcc     1776
Ala Ala Thr Val Lys Asp Ser Leu Val Thr Gly Ala Ala Ala Gln Ala
```

```
            580                 585                 590

gct gcg ctg ctg gcg ggt gcc ggc gcc gct agc acg gca acg ccg ctt     1824
Ala Ala Leu Leu Ala Gly Ala Gly Ala Ala Ser Thr Ala Thr Pro Leu
        595                 600                 605

gcg acg gtg gcc acg gtg ggc agt acg ctg tct ata ggt act gcc gcg     1872
Ala Thr Val Ala Thr Val Gly Ser Thr Leu Ser Ile Gly Thr Ala Ala
    610                 615                 620

tcc tcg cag atc gcg ctc gtc agc aag atc ggt gtc gac atg atg acc     1920
Ser Ser Gln Ile Ala Leu Val Ser Lys Ile Gly Val Asp Met Met Thr
625                 630                 635                 640

gcg ggg gcg atg ggc gca atc cgc agc gcg gcg aca ctg agc gct acg     1968
Ala Gly Ala Met Gly Ala Ile Arg Ser Ala Ala Thr Leu Ser Ala Thr
                645                 650                 655

gcg gat cag tac aac ctg tac cgc gcc tga                             1998
Ala Asp Gln Tyr Asn Leu Tyr Arg Ala
            660                 665


<210> SEQ ID NO 7
<211> LENGTH: 665
<212> TYPE: PRT
<213> ORGANISM: Sphingomonas sp. ATCC53159

<400> SEQUENCE: 7

Met Pro Asp Ile Ile Val Lys Asn Gln Thr Glu Leu Asn Ala Ala Ile
1               5                   10                  15

Ala Ala Ala Lys Gly Gly Glu Thr Ile Lys Leu Ala Ala Gly Val Tyr
            20                  25                  30

Thr Asp Leu Thr Val Met Thr Lys Thr Phe Thr Ser Met Val Thr Ile
        35                  40                  45

Glu Ser Leu Asp Ser Ser Asn Pro Val Asn Ile Gln Lys Leu Val Ile
    50                  55                  60

Gly Asn Ser Ser Asn Val Thr Val Lys Asn Met Val Ala Ala Thr Asp
65                  70                  75                  80

Tyr Lys Pro Ala Asp Asp Trp Asn Arg Leu Asn Thr Ile Gln Gly Ser
                85                  90                  95

Ala Asn Ile Val Leu Asp Gly Val Arg Phe Ser Gly Gly Thr Gly Asp
            100                 105                 110

Pro Ser Leu Ser Lys Gly Ala Gly Leu Phe Val Arg Asn Ser Thr Ser
        115                 120                 125

Val Thr Met Gln Asn Ser Ser Ile Asp His Phe Gly Leu Gly Leu Glu
    130                 135                 140

Ala Tyr Asn Val Asp Gly Met Val Val Gln Asn Ser Ser Phe His Asp
145                 150                 155                 160

Asn Arg Arg Asp His Thr Asn Phe Thr Glu Met Asn Asn Leu Val Ile
                165                 170                 175

Asp Gly Asn Ser Phe Thr Asn Leu Phe Pro Val Gly Thr Glu His Pro
            180                 185                 190

Asp Ala Ile Gln Phe Phe Thr Ala Gly Lys Val Lys Gly Asn Thr Asn
        195                 200                 205

Ile Thr Ile Ser Asn Asn Val Ile Met Gln Gly Ala Gly Ser Gly Ala
    210                 215                 220

Gln Gly Ile Phe Met Asn Asp Glu Ala Gly Asn Leu Pro Tyr Val Asn
225                 230                 235                 240

Val Asn Ile Lys Asn Asn Leu Ile Tyr Leu Asn Gly Tyr Tyr His Gly
                245                 250                 255

Ile Asn Val Val Asn Gly Val Asn Val Asn Ile Glu Ser Asn Ser Val
```

```
            260                 265                 270

Ile Ser Gln Val Asp Gly Thr Ser Phe Trp Ile Arg Leu Asp Lys Thr
        275                 280                 285

Asn Gly Ala Thr Ile Lys Asn Asn Val Ala Asp Leu Ile Thr Val Thr
    290                 295                 300

Ser Ser Ser Ser Asn Ile Val Gln Thr Gly Asn Arg Thr Leu Thr Ser
305                 310                 315                 320

Asp Ser Ala Thr Ile Arg Lys Ile Tyr Gly Leu Asn Asp Gly Ala Thr
                325                 330                 335

Ala Arg Leu Ser Asp Leu Ile Val Pro Gly Val Gly Tyr Gln Pro Pro
            340                 345                 350

Val Ser Ser Ala Ala Ala Ala Gln Val Thr Thr Glu Leu Ser Thr Ala
        355                 360                 365

Lys Ala Ala Asn Pro Ser Leu Leu Leu Asp Leu Ser Phe Ser Asn Ser
    370                 375                 380

Gly Val Val Asp Leu Ser His Trp Asn Thr Gly Gln Thr Thr Lys Ala
385                 390                 395                 400

Val Asp Val Ser Ala Val Val Gly Ser Ala Phe His Val Ser Thr Gly
                405                 410                 415

Thr Gly Val Glu Leu Asn Arg Ser Tyr Ser Arg Gln Ile Tyr Ala Leu
            420                 425                 430

Ser Ala Phe Thr Leu Ser Phe Asp Leu Lys Arg Asp Ser Ala Thr Ala
        435                 440                 445

Thr Ala Gly Gln Ile Leu Gly Ile Phe Gln Ser Trp Ser Val Ser Leu
    450                 455                 460

Gln Ala Asn Gly Glu Leu Ser Phe Thr Met Arg Asn Ala Ala Gly Val
465                 470                 475                 480

Ser Gln Thr Met Val Thr Ser Gly Ala Lys Leu Leu Asp Ala Ala Thr
                485                 490                 495

His Lys Ile Ala Leu Thr Tyr Asp Ser Thr Arg Lys Thr Ala Ile Leu
            500                 505                 510

Tyr Val Asp Gly Met Gln Arg Gly Thr Ala Thr Met Thr Gly Thr Thr
        515                 520                 525

Arg Pro Ala Glu Ser Trp Gly Leu Tyr Val Gly Ser Pro Phe Ser Thr
    530                 535                 540

Ala Phe Ser Gly Thr Val Gly Asp Ile Glu Ile Arg Asp Gly Ala Ile
545                 550                 555                 560

Ser Ala Ala Gln Val Gln Ala Leu Val Thr Ala Ser Ser Ala Ser Ala
                565                 570                 575

Ala Ala Thr Val Lys Asp Ser Leu Val Thr Gly Ala Ala Ala Gln Ala
            580                 585                 590

Ala Ala Leu Leu Ala Gly Ala Gly Ala Ala Ser Thr Ala Thr Pro Leu
        595                 600                 605

Ala Thr Val Ala Thr Val Gly Ser Thr Leu Ser Ile Gly Thr Ala Ala
    610                 615                 620

Ser Ser Gln Ile Ala Leu Val Ser Lys Ile Gly Val Asp Met Met Thr
625                 630                 635                 640

Ala Gly Ala Met Gly Ala Ile Arg Ser Ala Ala Thr Leu Ser Ala Thr
                645                 650                 655

Ala Asp Gln Tyr Asn Leu Tyr Arg Ala
            660                 665
```

<210> SEQ ID NO 8

```
<211> LENGTH: 939
<212> TYPE: DNA
<213> ORGANISM: Sphingomonas sp. ATCC53159
<220> FEATURE:
<221> NAME/KEY: CDS
<222> LOCATION: (1)..(939)

<400> SEQUENCE: 8

atg cag atg ctc cca acg ccc gat gtc agc ata ctc gtg gtc gct ttc       48
Met Gln Met Leu Pro Thr Pro Asp Val Ser Ile Leu Val Val Ala Phe
1               5                   10                  15

aac tcg acc gag tat atc gaa gac tgc ctg cgc ggc atc gcc gaa gga       96
Asn Ser Thr Glu Tyr Ile Glu Asp Cys Leu Arg Gly Ile Ala Glu Gly
            20                  25                  30

gcg ggc aag acc ccc cac gaa gtt ctg ctg atc gac aat ggc gac ggg      144
Ala Gly Lys Thr Pro His Glu Val Leu Leu Ile Asp Asn Gly Asp Gly
        35                  40                  45

cga acc gaa gcg ctg gtc cgg cag cgg ttc cac cac gtc cgc atc gtt      192
Arg Thr Glu Ala Leu Val Arg Gln Arg Phe His His Val Arg Ile Val
    50                  55                  60

ccc agt gag ggc aat att ggt ttc ggg gcc ggc aat aat cgc ctg gca      240
Pro Ser Glu Gly Asn Ile Gly Phe Gly Ala Gly Asn Asn Arg Leu Ala
65                  70                  75                  80

gcg cag gct gcc ggc ccg ctc ctg ctg ctc gtc aac ccc gat gcc att      288
Ala Gln Ala Ala Gly Pro Leu Leu Leu Leu Val Asn Pro Asp Ala Ile
                85                  90                  95

ccc cag ccc ggc gca atc gat cag ttg gtc acc ttt gcc aaa cag cat      336
Pro Gln Pro Gly Ala Ile Asp Gln Leu Val Thr Phe Ala Lys Gln His
            100                 105                 110

ccc gag gcg gcg gca tgg ggc ggc cgt tcc tac tcg ccc agc ggc gat      384
Pro Glu Ala Ala Ala Trp Gly Gly Arg Ser Tyr Ser Pro Ser Gly Asp
        115                 120                 125

cta gaa ccc gca aat ttc atg tcc ctg ccg acg ccc gcc gac ttt ctg      432
Leu Glu Pro Ala Asn Phe Met Ser Leu Pro Thr Pro Ala Asp Phe Leu
    130                 135                 140

acg gcg att ttc aac gcg cgt gcg cta cgc agc ggc ggg ctg caa gaa      480
Thr Ala Ile Phe Asn Ala Arg Ala Leu Arg Ser Gly Gly Leu Gln Glu
145                 150                 155                 160

ggc gcg acc acc ccc gga gcg gtc gag gtg ttg aat ggc ggc ttc atg      528
Gly Ala Thr Thr Pro Gly Ala Val Glu Val Leu Asn Gly Gly Phe Met
                165                 170                 175

atg gta cgc acc gat gtc tgg cag gcg atc ggc ggt ttt gac gag agc      576
Met Val Arg Thr Asp Val Trp Gln Ala Ile Gly Gly Phe Asp Glu Ser
            180                 185                 190

ttt ttt ctt tat tcg gaa gag atc gat ctc ttc cag cga atc cgc acg      624
Phe Phe Leu Tyr Ser Glu Glu Ile Asp Leu Phe Gln Arg Ile Arg Thr
        195                 200                 205

ttg ggg cac aag gtg ctc gtc gac ccc tcg gtc aaa gtg gta cac aat      672
Leu Gly His Lys Val Leu Val Asp Pro Ser Val Lys Val Val His Asn
    210                 215                 220

acg ggg agt ggt cag tcg atg tcc cag aac cgc ctg atg tat ctc acg      720
Thr Gly Ser Gly Gln Ser Met Ser Gln Asn Arg Leu Met Tyr Leu Thr
225                 230                 235                 240

acc ggg cgc atg cac tat gcg cga aag cat ttt ggc gca ctc ggc acc      768
Thr Gly Arg Met His Tyr Ala Arg Lys His Phe Gly Ala Leu Gly Thr
                245                 250                 255

ctt gcc acc ggg tgc gcg ctt tgg ctg atc gcc gcc aaa tac acg ttg      816
Leu Ala Thr Gly Cys Ala Leu Trp Leu Ile Ala Ala Lys Tyr Thr Leu
            260                 265                 270

gtc ggg gcg gca ctc tgg cgc ctg tcg ccg cgg acg ggc acg cga tac      864
Val Gly Ala Ala Leu Trp Arg Leu Ser Pro Arg Thr Gly Thr Arg Tyr
```

```
        275                 280                 285

aaa gag ctg agc aac ggg tgg cgt gcc gta ttt agc aat cct ggc cga      912
Lys Glu Leu Ser Asn Gly Trp Arg Ala Val Phe Ser Asn Pro Gly Arg
    290                 295                 300

tgg tgg agc ggc tat ccg cgt cgc taa                                  939
Trp Trp Ser Gly Tyr Pro Arg Arg
305                 310


<210> SEQ ID NO 9
<211> LENGTH: 312
<212> TYPE: PRT
<213> ORGANISM: Sphingomonas sp. ATCC53159

<400> SEQUENCE: 9

Met Gln Met Leu Pro Thr Pro Asp Val Ser Ile Leu Val Val Ala Phe
1               5                   10                  15

Asn Ser Thr Glu Tyr Ile Glu Asp Cys Leu Arg Gly Ile Ala Glu Gly
            20                  25                  30

Ala Gly Lys Thr Pro His Glu Val Leu Leu Ile Asp Asn Gly Asp Gly
        35                  40                  45

Arg Thr Glu Ala Leu Val Arg Gln Arg Phe His His Val Arg Ile Val
    50                  55                  60

Pro Ser Glu Gly Asn Ile Gly Phe Gly Ala Gly Asn Asn Arg Leu Ala
65                  70                  75                  80

Ala Gln Ala Ala Gly Pro Leu Leu Leu Leu Val Asn Pro Asp Ala Ile
                85                  90                  95

Pro Gln Pro Gly Ala Ile Asp Gln Leu Val Thr Phe Ala Lys Gln His
            100                 105                 110

Pro Glu Ala Ala Ala Trp Gly Gly Arg Ser Tyr Ser Pro Ser Gly Asp
        115                 120                 125

Leu Glu Pro Ala Asn Phe Met Ser Leu Pro Thr Pro Ala Asp Phe Leu
    130                 135                 140

Thr Ala Ile Phe Asn Ala Arg Ala Leu Arg Ser Gly Gly Leu Gln Glu
145                 150                 155                 160

Gly Ala Thr Thr Pro Gly Ala Val Glu Val Leu Asn Gly Gly Phe Met
                165                 170                 175

Met Val Arg Thr Asp Val Trp Gln Ala Ile Gly Gly Phe Asp Glu Ser
            180                 185                 190

Phe Phe Leu Tyr Ser Glu Glu Ile Asp Leu Phe Gln Arg Ile Arg Thr
        195                 200                 205

Leu Gly His Lys Val Leu Val Asp Pro Ser Val Lys Val Val His Asn
    210                 215                 220

Thr Gly Ser Gly Gln Ser Met Ser Gln Asn Arg Leu Met Tyr Leu Thr
225                 230                 235                 240

Thr Gly Arg Met His Tyr Ala Arg Lys His Phe Gly Ala Leu Gly Thr
                245                 250                 255

Leu Ala Thr Gly Cys Ala Leu Trp Leu Ile Ala Ala Lys Tyr Thr Leu
            260                 265                 270

Val Gly Ala Ala Leu Trp Arg Leu Ser Pro Arg Thr Gly Thr Arg Tyr
        275                 280                 285

Lys Glu Leu Ser Asn Gly Trp Arg Ala Val Phe Ser Asn Pro Gly Arg
    290                 295                 300

Trp Trp Ser Gly Tyr Pro Arg Arg
305                 310
```

```
<210> SEQ ID NO 10
<211> LENGTH: 972
<212> TYPE: DNA
<213> ORGANISM: Sphingomonas sp. ATCC53159
<220> FEATURE:
<221> NAME/KEY: CDS
<222> LOCATION: (1)..(972)

<400> SEQUENCE: 10

atg ctg cac tgc caa cgc tat tgc gga tgc ccg ccc gtc cga ata ggt       48
Met Leu His Cys Gln Arg Tyr Cys Gly Cys Pro Pro Val Arg Ile Gly
1               5                   10                  15

tca agt aga agt ttg tgc cgt gcg caa ttc cgt gcc ggc ggg gag gtc       96
Ser Ser Arg Ser Leu Cys Arg Ala Gln Phe Arg Ala Gly Gly Glu Val
            20                  25                  30

ttc atg aag aaa ttg tac ctg gtt acg gcg gtg gct gcg gcc gcg ctg      144
Phe Met Lys Lys Leu Tyr Leu Val Thr Ala Val Ala Ala Ala Ala Leu
        35                  40                  45

gcc gtc tcc gga tgt ggc ggc aag ggc ggc aag ctc gac aag ggg cag      192
Ala Val Ser Gly Cys Gly Gly Lys Gly Gly Lys Leu Asp Lys Gly Gln
    50                  55                  60

gtg gtc gcc agc gtc gat ggc gaa gaa atc acc gtc ttc gag ctg aat      240
Val Val Ala Ser Val Asp Gly Glu Glu Ile Thr Val Phe Glu Leu Asn
65                  70                  75                  80

gcc gaa ctg cag gcc tcc cag gta ccc ccg ggg acc gat cgc aag ctg      288
Ala Glu Leu Gln Ala Ser Gln Val Pro Pro Gly Thr Asp Arg Lys Leu
                85                  90                  95

gcc gag cag ctg gcg ctg cag cgc atc atc gag cgc aag atc ctc gcc      336
Ala Glu Gln Leu Ala Leu Gln Arg Ile Ile Glu Arg Lys Ile Leu Ala
            100                 105                 110

aag gtc gcc cgc gag cag aag ctg gac aag acg cct gcc ttc ctg atc      384
Lys Val Ala Arg Glu Gln Lys Leu Asp Lys Thr Pro Ala Phe Leu Ile
        115                 120                 125

cag gag cgc cgg gcc gac gag ctg atc ctc acc gcc atg ctg cgc gac      432
Gln Glu Arg Arg Ala Asp Glu Leu Ile Leu Thr Ala Met Leu Arg Asp
    130                 135                 140

aag atc gcc ggc ggc atc gcc cag ccg acc gat gcc gag atc gag aaa      480
Lys Ile Ala Gly Gly Ile Ala Gln Pro Thr Asp Ala Glu Ile Glu Lys
145                 150                 155                 160

tat cag gcc gcg cat ccg gag cgg ttc gcg cag cgc aag atc tac gcg      528
Tyr Gln Ala Ala His Pro Glu Arg Phe Ala Gln Arg Lys Ile Tyr Ala
                165                 170                 175

atc gat cag gtc gtc ttc gct ccg ccg agc tcg gcc gca aag ctc aag      576
Ile Asp Gln Val Val Phe Ala Pro Pro Ser Ser Ala Ala Lys Leu Lys
            180                 185                 190

caa ttc gcg ccg ctg aag acg ctg gac cag cta acc gcc aag ctc tcg      624
Gln Phe Ala Pro Leu Lys Thr Leu Asp Gln Leu Thr Ala Lys Leu Ser
        195                 200                 205

gcg gac aat gtc cag ttc cgt cgc gcg ccg tcg cag atc gac acc gct      672
Ala Asp Asn Val Gln Phe Arg Arg Ala Pro Ser Gln Ile Asp Thr Ala
    210                 215                 220

gcg ctg ccg ccg gaa atc gct gcc aag atc gcg tcg ctg ccg gca cag      720
Ala Leu Pro Pro Glu Ile Ala Ala Lys Ile Ala Ser Leu Pro Ala Gln
225                 230                 235                 240

gag atg ttc atc ctg ccg acc cag cag gga ctg acc gcg aat atc atc      768
Glu Met Phe Ile Leu Pro Thr Gln Gln Gly Leu Thr Ala Asn Ile Ile
                245                 250                 255

acg tcg acc acg gtg ctg ccg gtg ccg gcc gac cag gcg cgc gag atc      816
Thr Ser Thr Thr Val Leu Pro Val Pro Ala Asp Gln Ala Arg Glu Ile
            260                 265                 270

gcg ctc agc ggg ctg cgt acc gag cgc ttc ggc aag gcg gct gac gca      864
```

-continued

```
Ala Leu Ser Gly Leu Arg Thr Glu Arg Phe Gly Lys Ala Ala Asp Ala
        275                 280                 285

cag ctc aac gac cgc ctg aag aag gcg cgg gaa acc gtg aaa tat cag      912
Gln Leu Asn Asp Arg Leu Lys Lys Ala Arg Glu Thr Val Lys Tyr Gln
    290                 295                 300

gcc ggc tac agc gca ccg ccg cag ctt cgc ggc agc ggc gca acg ccg      960
Ala Gly Tyr Ser Ala Pro Pro Gln Leu Arg Gly Ser Gly Ala Thr Pro
305                 310                 315                 320

gcg ggg aac tga                                                      972
Ala Gly Asn


<210> SEQ ID NO 11
<211> LENGTH: 323
<212> TYPE: PRT
<213> ORGANISM: Sphingomonas sp. ATCC53159

<400> SEQUENCE: 11

Met Leu His Cys Gln Arg Tyr Cys Gly Cys Pro Pro Val Arg Ile Gly
1               5                   10                  15

Ser Ser Arg Ser Leu Cys Arg Ala Gln Phe Arg Ala Gly Gly Glu Val
            20                  25                  30

Phe Met Lys Lys Leu Tyr Leu Val Thr Ala Val Ala Ala Ala Ala Leu
        35                  40                  45

Ala Val Ser Gly Cys Gly Gly Lys Gly Gly Lys Leu Asp Lys Gly Gln
    50                  55                  60

Val Val Ala Ser Val Asp Gly Glu Glu Ile Thr Val Phe Glu Leu Asn
65                  70                  75                  80

Ala Glu Leu Gln Ala Ser Gln Val Pro Pro Gly Thr Asp Arg Lys Leu
                85                  90                  95

Ala Glu Gln Leu Ala Leu Gln Arg Ile Ile Glu Arg Lys Ile Leu Ala
            100                 105                 110

Lys Val Ala Arg Glu Gln Lys Leu Asp Lys Thr Pro Ala Phe Leu Ile
        115                 120                 125

Gln Glu Arg Arg Ala Asp Glu Leu Ile Leu Thr Ala Met Leu Arg Asp
    130                 135                 140

Lys Ile Ala Gly Gly Ile Ala Gln Pro Thr Asp Ala Glu Ile Glu Lys
145                 150                 155                 160

Tyr Gln Ala Ala His Pro Glu Arg Phe Ala Gln Arg Lys Ile Tyr Ala
                165                 170                 175

Ile Asp Gln Val Val Phe Ala Pro Pro Ser Ser Ala Ala Lys Leu Lys
            180                 185                 190

Gln Phe Ala Pro Leu Lys Thr Leu Asp Gln Leu Thr Ala Lys Leu Ser
        195                 200                 205

Ala Asp Asn Val Gln Phe Arg Arg Ala Pro Ser Gln Ile Asp Thr Ala
    210                 215                 220

Ala Leu Pro Pro Glu Ile Ala Ala Lys Ile Ala Ser Leu Pro Ala Gln
225                 230                 235                 240

Glu Met Phe Ile Leu Pro Thr Gln Gln Gly Leu Thr Ala Asn Ile Ile
                245                 250                 255

Thr Ser Thr Thr Val Leu Pro Val Pro Ala Asp Gln Ala Arg Glu Ile
            260                 265                 270

Ala Leu Ser Gly Leu Arg Thr Glu Arg Phe Gly Lys Ala Ala Asp Ala
        275                 280                 285

Gln Leu Asn Asp Arg Leu Lys Lys Ala Arg Glu Thr Val Lys Tyr Gln
    290                 295                 300
```

```
Ala Gly Tyr Ser Ala Pro Pro Gln Leu Arg Gly Ser Gly Ala Thr Pro
305                 310                 315                 320

Ala Gly Asn


<210> SEQ ID NO 12
<211> LENGTH: 1047
<212> TYPE: DNA
<213> ORGANISM: Sphingomonas sp. ATCC53159
<220> FEATURE:
<221> NAME/KEY: CDS
<222> LOCATION: (1)..(1044)

<400> SEQUENCE: 12

atg gca gaa gcg aac gcg gta gat gga aag gcc tcc aag ccg ctg aaa       48
Met Ala Glu Ala Asn Ala Val Asp Gly Lys Ala Ser Lys Pro Leu Lys
1               5                   10                  15

atg tgc ctt gca gcg tcg ggc ggc ggc cat ctc cgg caa atc ctc gat       96
Met Cys Leu Ala Ala Ser Gly Gly Gly His Leu Arg Gln Ile Leu Asp
            20                  25                  30

ctg gaa tcg gtg tgg cgc gaa cac gat tat ttc ttc gtt act gaa gat      144
Leu Glu Ser Val Trp Arg Glu His Asp Tyr Phe Phe Val Thr Glu Asp
        35                  40                  45

acc gcg ctc ggc cgg agc ctt gcc gaa aaa cat ccc gtc gaa ctg gtg      192
Thr Ala Leu Gly Arg Ser Leu Ala Glu Lys His Pro Val Glu Leu Val
    50                  55                  60

gag cac tat gcg ctc ggc cag gcc aag ctg ggc cat ccc ttg cgc atg      240
Glu His Tyr Ala Leu Gly Gln Ala Lys Leu Gly His Pro Leu Arg Met
65                  70                  75                  80

ctg ggc ggc gca tgg cgc aac ctg cgc cag agc ctt tcg atc ctg cgc      288
Leu Gly Gly Ala Trp Arg Asn Leu Arg Gln Ser Leu Ser Ile Leu Arg
                85                  90                  95

cgg cac aag ccg gat gtg gtg att tcc acc ggc gcg ggc gca gtc tat      336
Arg His Lys Pro Asp Val Val Ile Ser Thr Gly Ala Gly Ala Val Tyr
            100                 105                 110

ttc acc gcg ctg ctc gcc aaa ctg tcg ggc gcc aag ttc gtc cat atc      384
Phe Thr Ala Leu Leu Ala Lys Leu Ser Gly Ala Lys Phe Val His Ile
        115                 120                 125

gaa agc ttc gcg cgc ttc gac cac ccg tct gcc ttc ggc aag atg gtg      432
Glu Ser Phe Ala Arg Phe Asp His Pro Ser Ala Phe Gly Lys Met Val
    130                 135                 140

aag ggc atc gcg acg gtg acg atc gtc cag tcg gcg gcg ctg aaa gaa      480
Lys Gly Ile Ala Thr Val Thr Ile Val Gln Ser Ala Ala Leu Lys Glu
145                 150                 155                 160

acc tgg cct gat gcc gag ctg ttc gat ccg ttc cgc ctg ctc gat aca      528
Thr Trp Pro Asp Ala Glu Leu Phe Asp Pro Phe Arg Leu Leu Asp Thr
                165                 170                 175

ccg cgc ccg ccc aag cag gcg cta atc ttc gcg acg gtc ggc gcc acc      576
Pro Arg Pro Pro Lys Gln Ala Leu Ile Phe Ala Thr Val Gly Ala Thr
            180                 185                 190

ctg ccc ttc ccg cgg ctg gtg cag gca gtg ctc gac ctg aag cgc gcc      624
Leu Pro Phe Pro Arg Leu Val Gln Ala Val Leu Asp Leu Lys Arg Ala
        195                 200                 205

ggc ggg ctg ccg ggc aag ctg atc ctg caa tat ggc gac cag gac ctg      672
Gly Gly Leu Pro Gly Lys Leu Ile Leu Gln Tyr Gly Asp Gln Asp Leu
    210                 215                 220

ccc gat ccc ggc atc ccc gac gtc gag atc cgc cgt acc atc ccg ttc      720
Pro Asp Pro Gly Ile Pro Asp Val Glu Ile Arg Arg Thr Ile Pro Phe
225                 230                 235                 240

gac gat ctg cag ctg ctg ctg cgc gat gcg gat atg gtg ata tgc cac      768
Asp Asp Leu Gln Leu Leu Leu Arg Asp Ala Asp Met Val Ile Cys His
                245                 250                 255
```

```
ggc ggc acc gga tcg ctg gtc acg gcg ctg cgc gcc ggc tgc cgg gtc      816
Gly Gly Thr Gly Ser Leu Val Thr Ala Leu Arg Ala Gly Cys Arg Val
            260                 265                 270

gtc gcc ttt ccg cgc cgc cac gat ctg ggc gag cat tat gac gat cac      864
Val Ala Phe Pro Arg Arg His Asp Leu Gly Glu His Tyr Asp Asp His
        275                 280                 285

cag gaa gag atc gcc cag acc ttc gcc gac cgg ggc ctg ctc cag gcg      912
Gln Glu Glu Ile Ala Gln Thr Phe Ala Asp Arg Gly Leu Leu Gln Ala
    290                 295                 300

gtg cgc gac gag cgc cag ctc ggc gcc gct gtg gaa gcg gcc aag gca      960
Val Arg Asp Glu Arg Gln Leu Gly Ala Ala Val Glu Ala Ala Lys Ala
305                 310                 315                 320

acc gag ccg cag ctg gcg acc acc gac cac acg gcc ctc gcg gcg cgg     1008
Thr Glu Pro Gln Leu Ala Thr Thr Asp His Thr Ala Leu Ala Ala Arg
            325                 330                 335

ctg cgc cag ctg ctg gcg cag tgg agt gcc aag cga tga                 1047
Leu Arg Gln Leu Leu Ala Gln Trp Ser Ala Lys Arg
            340                 345


<210> SEQ ID NO 13
<211> LENGTH: 348
<212> TYPE: PRT
<213> ORGANISM: Sphingomonas sp. ATCC53159

<400> SEQUENCE: 13

Met Ala Glu Ala Asn Ala Val Asp Gly Lys Ala Ser Lys Pro Leu Lys
1               5                   10                  15

Met Cys Leu Ala Ala Ser Gly Gly Gly His Leu Arg Gln Ile Leu Asp
            20                  25                  30

Leu Glu Ser Val Trp Arg Glu His Asp Tyr Phe Phe Val Thr Glu Asp
        35                  40                  45

Thr Ala Leu Gly Arg Ser Leu Ala Glu Lys His Pro Val Glu Leu Val
    50                  55                  60

Glu His Tyr Ala Leu Gly Gln Ala Lys Leu Gly His Pro Leu Arg Met
65                  70                  75                  80

Leu Gly Gly Ala Trp Arg Asn Leu Arg Gln Ser Leu Ser Ile Leu Arg
                85                  90                  95

Arg His Lys Pro Asp Val Val Ile Ser Thr Gly Ala Gly Ala Val Tyr
            100                 105                 110

Phe Thr Ala Leu Leu Ala Lys Leu Ser Gly Ala Lys Phe Val His Ile
        115                 120                 125

Glu Ser Phe Ala Arg Phe Asp His Pro Ser Ala Phe Gly Lys Met Val
    130                 135                 140

Lys Gly Ile Ala Thr Val Thr Ile Val Gln Ser Ala Ala Leu Lys Glu
145                 150                 155                 160

Thr Trp Pro Asp Ala Glu Leu Phe Asp Pro Phe Arg Leu Leu Asp Thr
                165                 170                 175

Pro Arg Pro Pro Lys Gln Ala Leu Ile Phe Ala Thr Val Gly Ala Thr
            180                 185                 190

Leu Pro Phe Pro Arg Leu Val Gln Ala Val Leu Asp Leu Lys Arg Ala
        195                 200                 205

Gly Gly Leu Pro Gly Lys Leu Ile Leu Gln Tyr Gly Asp Gln Asp Leu
    210                 215                 220

Pro Asp Pro Gly Ile Pro Asp Val Glu Ile Arg Arg Thr Ile Pro Phe
225                 230                 235                 240

Asp Asp Leu Gln Leu Leu Leu Arg Asp Ala Asp Met Val Ile Cys His
```

```
                245                 250                 255

Gly Gly Thr Gly Ser Leu Val Thr Ala Leu Arg Ala Gly Cys Arg Val
            260                 265                 270

Val Ala Phe Pro Arg Arg His Asp Leu Gly Glu His Tyr Asp Asp His
        275                 280                 285

Gln Glu Glu Ile Ala Gln Thr Phe Ala Asp Arg Gly Leu Leu Gln Ala
    290                 295                 300

Val Arg Asp Glu Arg Gln Leu Gly Ala Ala Val Glu Ala Ala Lys Ala
305                 310                 315                 320

Thr Glu Pro Gln Leu Ala Thr Thr Asp His Thr Ala Leu Ala Ala Arg
                325                 330                 335

Leu Arg Gln Leu Leu Ala Gln Trp Ser Ala Lys Arg
            340                 345


<210> SEQ ID NO 14
<211> LENGTH: 867
<212> TYPE: DNA
<213> ORGANISM: Sphingomonas sp. ATCC53159
<220> FEATURE:
<221> NAME/KEY: CDS
<222> LOCATION: (1)..(867)

<400> SEQUENCE: 14

atg agc acg ccc cgg atc agc gtc gtc atc ccg cac tat aac gat ccg       48
Met Ser Thr Pro Arg Ile Ser Val Val Ile Pro His Tyr Asn Asp Pro
1               5                   10                  15

caa tcc ttg cgg ctc tgc ctg gat gcg ctg gag cgg cag acg atc ggt       96
Gln Ser Leu Arg Leu Cys Leu Asp Ala Leu Glu Arg Gln Thr Ile Gly
            20                  25                  30

cgc gac gcg ttc gag atc atc gtc ggc gac aac aat tcg ccc tgt ggg      144
Arg Asp Ala Phe Glu Ile Ile Val Gly Asp Asn Asn Ser Pro Cys Gly
        35                  40                  45

ctc gcg gcg gtg gag gcg gcg gtc gcc gga cgt gcg cgg atc gtg acc      192
Leu Ala Ala Val Glu Ala Ala Val Ala Gly Arg Ala Arg Ile Val Thr
    50                  55                  60

att ctg gaa aag ggg gcg ggc ccc gcg cgc aac ggg gcg gca gcc gca      240
Ile Leu Glu Lys Gly Ala Gly Pro Ala Arg Asn Gly Ala Ala Ala Ala
65                  70                  75                  80

gcg cgt ggc gag atc ctc gcc ttt acc gac agt gac tgc gtg gtg gag      288
Ala Arg Gly Glu Ile Leu Ala Phe Thr Asp Ser Asp Cys Val Val Glu
                85                  90                  95

ccc ggc tgg ctg gcg ggc ggc acg acc agg gtc gcg cct ggc cgt ttc      336
Pro Gly Trp Leu Ala Gly Gly Thr Thr Arg Val Ala Pro Gly Arg Phe
            100                 105                 110

atc ggc ggg cac atg tat gtg cgc aag ccc gaa ggg ccg ccg aac ggc      384
Ile Gly Gly His Met Tyr Val Arg Lys Pro Glu Gly Pro Pro Asn Gly
        115                 120                 125

gcc gag gcg ctg gag atg gcg ctg gcg ttc gac aat gaa ggc tat gtg      432
Ala Glu Ala Leu Glu Met Ala Leu Ala Phe Asp Asn Glu Gly Tyr Val
    130                 135                 140

cgg cgc acc cag ttc acg gtc acc gca aac ctg ttc gtg atg cgc gcc      480
Arg Arg Thr Gln Phe Thr Val Thr Ala Asn Leu Phe Val Met Arg Ala
145                 150                 155                 160

gat ttc gaa cgg gtc ggc ggc ttc cgc gtt ggc gtg tcc gag gat ctg      528
Asp Phe Glu Arg Val Gly Gly Phe Arg Val Gly Val Ser Glu Asp Leu
                165                 170                 175

gaa tgg tgc cac cgg gcg atc gcc agc ggc ctc acc atc aac tat gca      576
Glu Trp Cys His Arg Ala Ile Ala Ser Gly Leu Thr Ile Asn Tyr Ala
            180                 185                 190
```

```
ccg gat gca tcg gtg ggc cac ccg ccc cgg ccc gac tgg tcg gcc ctg      624
Pro Asp Ala Ser Val Gly His Pro Pro Arg Pro Asp Trp Ser Ala Leu
        195                 200                 205

ctg gtg aag acg cgg cgc atc cag cgc gaa ctc tat ctg ttc aac atc      672
Leu Val Lys Thr Arg Arg Ile Gln Arg Glu Leu Tyr Leu Phe Asn Ile
    210                 215                 220

gag cgg ccg aag ggc agg ctg cgc tgg ctg gtc cgt tcc gtg gcg caa      720
Glu Arg Pro Lys Gly Arg Leu Arg Trp Leu Val Arg Ser Val Ala Gln
225                 230                 235                 240

ccg gcg atg atc cca cag gac gtg gcc aag atc ctg cgc aca ccg ggt      768
Pro Ala Met Ile Pro Gln Asp Val Ala Lys Ile Leu Arg Thr Pro Gly
                245                 250                 255

acc aag ggc gcg cgc ctc gct gcg gtc acc acg ctg gtc cgg ctg cgg      816
Thr Lys Gly Ala Arg Leu Ala Ala Val Thr Thr Leu Val Arg Leu Arg
            260                 265                 270

ctg tgg cgc ggc ggc gcc ggc ttg ttg cag ttg ctc ggc cgc gac atc      864
Leu Trp Arg Gly Gly Ala Gly Leu Leu Gln Leu Leu Gly Arg Asp Ile
        275                 280                 285

tga                                                                  867


<210> SEQ ID NO 15
<211> LENGTH: 288
<212> TYPE: PRT
<213> ORGANISM: Sphingomonas sp. ATCC53159

<400> SEQUENCE: 15

Met Ser Thr Pro Arg Ile Ser Val Val Ile Pro His Tyr Asn Asp Pro
1               5                   10                  15

Gln Ser Leu Arg Leu Cys Leu Asp Ala Leu Glu Arg Gln Thr Ile Gly
            20                  25                  30

Arg Asp Ala Phe Glu Ile Ile Val Gly Asp Asn Asn Ser Pro Cys Gly
        35                  40                  45

Leu Ala Ala Val Glu Ala Ala Val Ala Gly Arg Ala Arg Ile Val Thr
    50                  55                  60

Ile Leu Glu Lys Gly Ala Gly Pro Ala Arg Asn Gly Ala Ala Ala Ala
65                  70                  75                  80

Ala Arg Gly Glu Ile Leu Ala Phe Thr Asp Ser Asp Cys Val Val Glu
                85                  90                  95

Pro Gly Trp Leu Ala Gly Gly Thr Thr Arg Val Ala Pro Gly Arg Phe
            100                 105                 110

Ile Gly Gly His Met Tyr Val Arg Lys Pro Glu Gly Pro Pro Asn Gly
        115                 120                 125

Ala Glu Ala Leu Glu Met Ala Leu Ala Phe Asp Asn Glu Gly Tyr Val
    130                 135                 140

Arg Arg Thr Gln Phe Thr Val Thr Ala Asn Leu Phe Val Met Arg Ala
145                 150                 155                 160

Asp Phe Glu Arg Val Gly Gly Phe Arg Val Gly Val Ser Glu Asp Leu
                165                 170                 175

Glu Trp Cys His Arg Ala Ile Ala Ser Gly Leu Thr Ile Asn Tyr Ala
            180                 185                 190

Pro Asp Ala Ser Val Gly His Pro Pro Arg Pro Asp Trp Ser Ala Leu
        195                 200                 205

Leu Val Lys Thr Arg Arg Ile Gln Arg Glu Leu Tyr Leu Phe Asn Ile
    210                 215                 220

Glu Arg Pro Lys Gly Arg Leu Arg Trp Leu Val Arg Ser Val Ala Gln
225                 230                 235                 240
```

```
Pro Ala Met Ile Pro Gln Asp Val Ala Lys Ile Leu Arg Thr Pro Gly
                245                 250                 255

Thr Lys Gly Ala Arg Leu Ala Ala Val Thr Thr Leu Val Arg Leu Arg
            260                 265                 270

Leu Trp Arg Gly Gly Ala Gly Leu Leu Gln Leu Leu Gly Arg Asp Ile
        275                 280                 285


<210> SEQ ID NO 16
<211> LENGTH: 1389
<212> TYPE: DNA
<213> ORGANISM: Sphingomonas sp. ATCC53159
<220> FEATURE:
<221> NAME/KEY: CDS
<222> LOCATION: (1)..(1389)

<400> SEQUENCE: 16

gtg gct gta ggt tcc gcg ctg aga ttc ttg tgg ccg ttc ggc cgt cga       48
Val Ala Val Gly Ser Ala Leu Arg Phe Leu Trp Pro Phe Gly Arg Arg
1               5                   10                  15

gaa gaa cct gaa gaa gag ggc tat ttc ccg ctg act gcg aca gtg gtg       96
Glu Glu Pro Glu Glu Glu Gly Tyr Phe Pro Leu Thr Ala Thr Val Val
            20                  25                  30

ccg cat cgc gat gcc cat agc ggc cgt ggt cgc ccg gat ttc cca acc      144
Pro His Arg Asp Ala His Ser Gly Arg Gly Arg Pro Asp Phe Pro Thr
        35                  40                  45

ttc cgt gcc tcc gcg ctg gac cgc ccg ctg gat cgc cgc cgc gac gag      192
Phe Arg Ala Ser Ala Leu Asp Arg Pro Leu Asp Arg Arg Arg Asp Glu
    50                  55                  60

cgc cgc gag atc acg cgc gcc cgg ttc gcg ctg gcg acc ttc ttc aca      240
Arg Arg Glu Ile Thr Arg Ala Arg Phe Ala Leu Ala Thr Phe Phe Thr
65                  70                  75                  80

ccc acc cag ccg gtg gcc gat cgg tcg agc ttc gcc ggg cgc ctc ggc      288
Pro Thr Gln Pro Val Ala Asp Arg Ser Ser Phe Ala Gly Arg Leu Gly
                85                  90                  95

gtg ctg gcg cgc cta atc tcc tcg atc gag agc cag cgc agc cat gtc      336
Val Leu Ala Arg Leu Ile Ser Ser Ile Glu Ser Gln Arg Ser His Val
            100                 105                 110

gtg ctc tat ggc gag cgc ggc atc ggc aag acc tcg ctg ctc cac gtg      384
Val Leu Tyr Gly Glu Arg Gly Ile Gly Lys Thr Ser Leu Leu His Val
        115                 120                 125

ctg acc gat gtc gcc cgc gaa tcc agc tat atc gtc agc tat gcg acc      432
Leu Thr Asp Val Ala Arg Glu Ser Ser Tyr Ile Val Ser Tyr Ala Thr
    130                 135                 140

tgc ggt gcg aac gcg aat ttc agc gat gtc ttc cgc gcc gtg ctg gaa      480
Cys Gly Ala Asn Ala Asn Phe Ser Asp Val Phe Arg Ala Val Leu Glu
145                 150                 155                 160

gac gtg ccg ctg ctg ttc cat cgc ggc gtg gcg ccc aac gcc ggc gag      528
Asp Val Pro Leu Leu Phe His Arg Gly Val Ala Pro Asn Ala Gly Glu
                165                 170                 175

gcg gag agc ggc ggc aac ttg gcc gac cgc ctg ccg acg ggc agc ttc      576
Ala Glu Ser Gly Gly Asn Leu Ala Asp Arg Leu Pro Thr Gly Ser Phe
            180                 185                 190

ggg ccc ggc gaa ctg gcc gac ctg tgc gcc gac atc acg ggc aca cgc      624
Gly Pro Gly Glu Leu Ala Asp Leu Cys Ala Asp Ile Thr Gly Thr Arg
        195                 200                 205

gtg ctg atc atc ctc gac gaa tat gat cgc gtc agc gat tcc gcc ttc      672
Val Leu Ile Ile Leu Asp Glu Tyr Asp Arg Val Ser Asp Ser Ala Phe
    210                 215                 220

cgt cag cag gtc gcc gag ctg atc aag aac ctg tcg gac cgt tcg gcg      720
Arg Gln Gln Val Ala Glu Leu Ile Lys Asn Leu Ser Asp Arg Ser Ala
225                 230                 235                 240
```

```
cgc gtc cag ctg gtg atc gcg ggc gtc gcc tcg aac ctg cag gag ctg      768
Arg Val Gln Leu Val Ile Ala Gly Val Ala Ser Asn Leu Gln Glu Leu
                245                 250                 255

atc ggt tat gcg ccg tcg atc cgc cgc aac gtc atc ggc ctg ccg atg      816
Ile Gly Tyr Ala Pro Ser Ile Arg Arg Asn Val Ile Gly Leu Pro Met
            260                 265                 270

ccc cgg ctg gag gaa tcg gag gtg cag gag atg atc gcg ctc ggc gaa      864
Pro Arg Leu Glu Glu Ser Glu Val Gln Glu Met Ile Ala Leu Gly Glu
        275                 280                 285

acc gcc tcg ggc gtt cgc ttc gat ccg gac ctg act cac atg atc cac      912
Thr Ala Ser Gly Val Arg Phe Asp Pro Asp Leu Thr His Met Ile His
    290                 295                 300

ctg ctc gcg ctg ggg tcg ccc tat ttc gcg cgg ctg ctg tgc cac cat      960
Leu Leu Ala Leu Gly Ser Pro Tyr Phe Ala Arg Leu Leu Cys His His
305                 310                 315                 320

tcc gcg ctg gaa gcc ctg gac cag ggc cgc ctc acg gtc gac gcc ggg     1008
Ser Ala Leu Glu Ala Leu Asp Gln Gly Arg Leu Thr Val Asp Ala Gly
                325                 330                 335

cat ctg cgt cgt gcg ctc gac cag gcg atc ctt gag atc gag ggc cgc     1056
His Leu Arg Arg Ala Leu Asp Gln Ala Ile Leu Glu Ile Glu Gly Arg
            340                 345                 350

atg ccg ccg cgc gcg gtg atc gag atg cgc aag ttc gtc ggc ggc cgc     1104
Met Pro Pro Arg Ala Val Ile Glu Met Arg Lys Phe Val Gly Gly Arg
        355                 360                 365

tac gat cca ctc gtc gcg gcg ctg ggc gag gcc tcg cgc tcg gcg gat     1152
Tyr Asp Pro Leu Val Ala Ala Leu Gly Glu Ala Ser Arg Ser Ala Asp
    370                 375                 380

ggc tgg ttc agc ggc caa gcc gtg gtg gat ctg ctg ccg ggc gcg cac     1200
Gly Trp Phe Ser Gly Gln Ala Val Val Asp Leu Leu Pro Gly Ala His
385                 390                 395                 400

atc acg gcg gcg cag gtc gag cag gag ctg ggc gag ctc acc ggt caa     1248
Ile Thr Ala Ala Gln Val Glu Gln Glu Leu Gly Glu Leu Thr Gly Gln
                405                 410                 415

ctc ggc ctc gaa tcc gaa acg cag gac ggc gat tgc cgc ttc cgc ttc     1296
Leu Gly Leu Glu Ser Glu Thr Gln Asp Gly Asp Cys Arg Phe Arg Phe
            420                 425                 430

acc gac gat acg ctg ccg gtc tat ctg tgg ctg atg atc ggc cgc ctg     1344
Thr Asp Asp Thr Leu Pro Val Tyr Leu Trp Leu Met Ile Gly Arg Leu
        435                 440                 445

cgg ctc gac agc ggc acg ctg gaa gac gcg ctg gcc acc gtc tga         1389
Arg Leu Asp Ser Gly Thr Leu Glu Asp Ala Leu Ala Thr Val
    450                 455                 460


<210> SEQ ID NO 17
<211> LENGTH: 462
<212> TYPE: PRT
<213> ORGANISM: Sphingomonas sp. ATCC53159

<400> SEQUENCE: 17

Val Ala Val Gly Ser Ala Leu Arg Phe Leu Trp Pro Phe Gly Arg Arg
1               5                   10                  15

Glu Glu Pro Glu Glu Glu Gly Tyr Phe Pro Leu Thr Ala Thr Val Val
            20                  25                  30

Pro His Arg Asp Ala His Ser Gly Arg Gly Arg Pro Asp Phe Pro Thr
        35                  40                  45

Phe Arg Ala Ser Ala Leu Asp Arg Pro Leu Asp Arg Arg Arg Asp Glu
    50                  55                  60

Arg Arg Glu Ile Thr Arg Ala Arg Phe Ala Leu Ala Thr Phe Phe Thr
65                  70                  75                  80
```

```
Pro Thr Gln Pro Val Ala Asp Arg Ser Ser Phe Ala Gly Arg Leu Gly
                85                  90                  95

Val Leu Ala Arg Leu Ile Ser Ser Ile Glu Ser Gln Arg Ser His Val
            100                 105                 110

Val Leu Tyr Gly Glu Arg Gly Ile Gly Lys Thr Ser Leu Leu His Val
        115                 120                 125

Leu Thr Asp Val Ala Arg Glu Ser Ser Tyr Ile Val Ser Tyr Ala Thr
    130                 135                 140

Cys Gly Ala Asn Ala Asn Phe Ser Asp Val Phe Arg Ala Val Leu Glu
145                 150                 155                 160

Asp Val Pro Leu Leu Phe His Arg Gly Val Ala Pro Asn Ala Gly Glu
                165                 170                 175

Ala Glu Ser Gly Gly Asn Leu Ala Asp Arg Leu Pro Thr Gly Ser Phe
            180                 185                 190

Gly Pro Gly Glu Leu Ala Asp Leu Cys Ala Asp Ile Thr Gly Thr Arg
        195                 200                 205

Val Leu Ile Ile Leu Asp Glu Tyr Asp Arg Val Ser Asp Ser Ala Phe
    210                 215                 220

Arg Gln Gln Val Ala Glu Leu Ile Lys Asn Leu Ser Asp Arg Ser Ala
225                 230                 235                 240

Arg Val Gln Leu Val Ile Ala Gly Val Ala Ser Asn Leu Gln Glu Leu
                245                 250                 255

Ile Gly Tyr Ala Pro Ser Ile Arg Arg Asn Val Ile Gly Leu Pro Met
            260                 265                 270

Pro Arg Leu Glu Glu Ser Glu Val Gln Glu Met Ile Ala Leu Gly Glu
        275                 280                 285

Thr Ala Ser Gly Val Arg Phe Asp Pro Asp Leu Thr His Met Ile His
    290                 295                 300

Leu Leu Ala Leu Gly Ser Pro Tyr Phe Ala Arg Leu Leu Cys His His
305                 310                 315                 320

Ser Ala Leu Glu Ala Leu Asp Gln Gly Arg Leu Thr Val Asp Ala Gly
                325                 330                 335

His Leu Arg Arg Ala Leu Asp Gln Ala Ile Leu Glu Ile Glu Gly Arg
            340                 345                 350

Met Pro Pro Arg Ala Val Ile Glu Met Arg Lys Phe Val Gly Gly Arg
        355                 360                 365

Tyr Asp Pro Leu Val Ala Ala Leu Gly Glu Ala Ser Arg Ser Ala Asp
    370                 375                 380

Gly Trp Phe Ser Gly Gln Ala Val Val Asp Leu Leu Pro Gly Ala His
385                 390                 395                 400

Ile Thr Ala Ala Gln Val Glu Gln Glu Leu Gly Glu Leu Thr Gly Gln
                405                 410                 415

Leu Gly Leu Glu Ser Glu Thr Gln Asp Gly Asp Cys Arg Phe Arg Phe
            420                 425                 430

Thr Asp Asp Thr Leu Pro Val Tyr Leu Trp Leu Met Ile Gly Arg Leu
        435                 440                 445

Arg Leu Asp Ser Gly Thr Leu Glu Asp Ala Leu Ala Thr Val
    450                 455                 460
```

<210> SEQ ID NO 18
<211> LENGTH: 1299
<212> TYPE: DNA
<213> ORGANISM: Sphingomonas sp. ATCC53159
<220> FEATURE:

```
<221> NAME/KEY: CDS
<222> LOCATION: (1)..(1299)

<400> SEQUENCE: 18

atg aag ccg aga ccc ggg gga acc ttt atg caa gta aat ttc aat cga       48
Met Lys Pro Arg Pro Gly Gly Thr Phe Met Gln Val Asn Phe Asn Arg
1               5                   10                  15

cag gct cgc aag ctc ggt gcc ggc aat gcg ctc gcg cgg ggg ggg ccc       96
Gln Ala Arg Lys Leu Gly Ala Gly Asn Ala Leu Ala Arg Gly Gly Pro
            20                  25                  30

gtg ctt gcg ctg ctt gcg acc gcg gca tgg aca caa cct gcg ctg gcg      144
Val Leu Ala Leu Leu Ala Thr Ala Ala Trp Thr Gln Pro Ala Leu Ala
        35                  40                  45

cag cga cag gca ttt gag tcc cgc ccc tcc ggt agc gag cga cag gtc      192
Gln Arg Gln Ala Phe Glu Ser Arg Pro Ser Gly Ser Glu Arg Gln Val
    50                  55                  60

gat att cgc gcg acg ggg tcg ctg gaa tat gac gac aac gtc gtg ctg      240
Asp Ile Arg Ala Thr Gly Ser Leu Glu Tyr Asp Asp Asn Val Val Leu
65                  70                  75                  80

aac gac cag cgg atc acg gac ggc gcg cgt ggc gat gtg atc gca tcg      288
Asn Asp Gln Arg Ile Thr Asp Gly Ala Arg Gly Asp Val Ile Ala Ser
                85                  90                  95

ccc ggg ctg gac gtg acc cta gtt ctg ccc cgc gcc acc ggg cag ctc      336
Pro Gly Leu Asp Val Thr Leu Val Leu Pro Arg Ala Thr Gly Gln Leu
            100                 105                 110

tac ctc acc ggc aat gtc gga tat cgc ttt tac aag cga tat acc aac      384
Tyr Leu Thr Gly Asn Val Gly Tyr Arg Phe Tyr Lys Arg Tyr Thr Asn
        115                 120                 125

ttt aac cgc gag cag atc tcg ctc acc ggc ggc gca gat cag cgg ttc      432
Phe Asn Arg Glu Gln Ile Ser Leu Thr Gly Gly Ala Asp Gln Arg Phe
    130                 135                 140

gcc tcc tgc gtc gtg cac ggg gaa gtc ggc tat cag cgc cac ctc acc      480
Ala Ser Cys Val Val His Gly Glu Val Gly Tyr Gln Arg His Leu Thr
145                 150                 155                 160

gac ctg tcc agc atc ttg atc cag gac acc acg cct gcg ctc aac aac      528
Asp Leu Ser Ser Ile Leu Ile Gln Asp Thr Thr Pro Ala Leu Asn Asn
                165                 170                 175

acc gaa gag gcc cgg cag tac acc gcg gat atc ggc tgc ggc gcg acc      576
Thr Glu Glu Ala Arg Gln Tyr Thr Ala Asp Ile Gly Cys Gly Ala Thr
            180                 185                 190

tac ggc ctg cgg cct gcc gtt tcc tac acc cgc aac gaa gtg cgc aac      624
Tyr Gly Leu Arg Pro Ala Val Ser Tyr Thr Arg Asn Glu Val Arg Asn
        195                 200                 205

agc ctt gcc gag cgc cga tac gcg gac tcg aat acc aac acc ttt acc      672
Ser Leu Ala Glu Arg Arg Tyr Ala Asp Ser Asn Thr Asn Thr Phe Thr
    210                 215                 220

gca cag ctt ggc ctg act tcg cct gcc ctg ggg acc gtg gcg gta ttt      720
Ala Gln Leu Gly Leu Thr Ser Pro Ala Leu Gly Thr Val Ala Val Phe
225                 230                 235                 240

ggg cgt atg tcc gac agc agc tat gtc cat cgc gtc ctt ccc ggc att      768
Gly Arg Met Ser Asp Ser Ser Tyr Val His Arg Val Leu Pro Gly Ile
                245                 250                 255

acc ggc cag gac ggg atg aag agc tac gcg gcc ggc gtc cag ctc gag      816
Thr Gly Gln Asp Gly Met Lys Ser Tyr Ala Ala Gly Val Gln Leu Glu
            260                 265                 270

cgc tcg gtg gcc aac cga ctc cat ttc aac ggc tcg gtg aat tac acc      864
Arg Ser Val Ala Asn Arg Leu His Phe Asn Gly Ser Val Asn Tyr Thr
        275                 280                 285

gag gtt gac cca aag ctc gca tcc acc aaa gga ttc aag ggc gta gga      912
Glu Val Asp Pro Lys Leu Ala Ser Thr Lys Gly Phe Lys Gly Val Gly
```

```
    290                 295                 300

ttt aac gtt tcc ggc gat tat gct ggt gat cag tac agc ctc caa ttg      960
Phe Asn Val Ser Gly Asp Tyr Ala Gly Asp Gln Tyr Ser Leu Gln Leu
305                 310                 315                 320

ctg gct tca cga tcg ccc cag cct tca ctt ctt ctg ttc gtg ggt tac     1008
Leu Ala Ser Arg Ser Pro Gln Pro Ser Leu Leu Leu Phe Val Gly Tyr
                325                 330                 335

gag att gtg aca gcg gtt tcg gcg aat gcg acg cgc cgg ctg agc gat     1056
Glu Ile Val Thr Ala Val Ser Ala Asn Ala Thr Arg Arg Leu Ser Asp
            340                 345                 350

cgc att cag ata tcg ctg caa ggc agc cga acc tgg cgc gag ctc gcg     1104
Arg Ile Gln Ile Ser Leu Gln Gly Ser Arg Thr Trp Arg Glu Leu Ala
        355                 360                 365

tct tcg cgg ctg ctc acc aac gtg ccg att tcc ggc aac gac aac acc     1152
Ser Ser Arg Leu Leu Thr Asn Val Pro Ile Ser Gly Asn Asp Asn Thr
    370                 375                 380

tcg acg ttg ttc gcc tcc gct acc ttc cgg ccg aat cgc cgg ctg agc     1200
Ser Thr Leu Phe Ala Ser Ala Thr Phe Arg Pro Asn Arg Arg Leu Ser
385                 390                 395                 400

ttt gtg ctg ggt gcc ggc ctt cag cgg cgc acc agc aac acg cag cta     1248
Phe Val Leu Gly Ala Gly Leu Gln Arg Arg Thr Ser Asn Thr Gln Leu
                405                 410                 415

tac agt tac agc tcc aaa cgc atc aat ctc tcg acg tcg ctt tcg ctc     1296
Tyr Ser Tyr Ser Ser Lys Arg Ile Asn Leu Ser Thr Ser Leu Ser Leu
            420                 425                 430

tga                                                                 1299


<210> SEQ ID NO 19
<211> LENGTH: 432
<212> TYPE: PRT
<213> ORGANISM: Sphingomonas sp. ATCC53159

<400> SEQUENCE: 19

Met Lys Pro Arg Pro Gly Gly Thr Phe Met Gln Val Asn Phe Asn Arg
1               5                   10                  15

Gln Ala Arg Lys Leu Gly Ala Gly Asn Ala Leu Ala Arg Gly Gly Pro
            20                  25                  30

Val Leu Ala Leu Leu Ala Thr Ala Ala Trp Thr Gln Pro Ala Leu Ala
        35                  40                  45

Gln Arg Gln Ala Phe Glu Ser Arg Pro Ser Gly Ser Glu Arg Gln Val
    50                  55                  60

Asp Ile Arg Ala Thr Gly Ser Leu Glu Tyr Asp Asp Asn Val Val Leu
65                  70                  75                  80

Asn Asp Gln Arg Ile Thr Asp Gly Ala Arg Gly Asp Val Ile Ala Ser
                85                  90                  95

Pro Gly Leu Asp Val Thr Leu Val Leu Pro Arg Ala Thr Gly Gln Leu
            100                 105                 110

Tyr Leu Thr Gly Asn Val Gly Tyr Arg Phe Tyr Lys Arg Tyr Thr Asn
        115                 120                 125

Phe Asn Arg Glu Gln Ile Ser Leu Thr Gly Gly Ala Asp Gln Arg Phe
    130                 135                 140

Ala Ser Cys Val Val His Gly Glu Val Gly Tyr Gln Arg His Leu Thr
145                 150                 155                 160

Asp Leu Ser Ser Ile Leu Ile Gln Asp Thr Thr Pro Ala Leu Asn Asn
                165                 170                 175

Thr Glu Glu Ala Arg Gln Tyr Thr Ala Asp Ile Gly Cys Gly Ala Thr
            180                 185                 190
```

```
Tyr Gly Leu Arg Pro Ala Val Ser Tyr Thr Arg Asn Glu Val Arg Asn
        195                 200                 205

Ser Leu Ala Glu Arg Arg Tyr Ala Asp Ser Asn Thr Asn Thr Phe Thr
    210                 215                 220

Ala Gln Leu Gly Leu Thr Ser Pro Ala Leu Gly Thr Val Ala Val Phe
225                 230                 235                 240

Gly Arg Met Ser Asp Ser Ser Tyr Val His Arg Val Leu Pro Gly Ile
                245                 250                 255

Thr Gly Gln Asp Gly Met Lys Ser Tyr Ala Ala Gly Val Gln Leu Glu
            260                 265                 270

Arg Ser Val Ala Asn Arg Leu His Phe Asn Gly Ser Val Asn Tyr Thr
        275                 280                 285

Glu Val Asp Pro Lys Leu Ala Ser Thr Lys Gly Phe Lys Gly Val Gly
    290                 295                 300

Phe Asn Val Ser Gly Asp Tyr Ala Gly Asp Gln Tyr Ser Leu Gln Leu
305                 310                 315                 320

Leu Ala Ser Arg Ser Pro Gln Pro Ser Leu Leu Leu Phe Val Gly Tyr
                325                 330                 335

Glu Ile Val Thr Ala Val Ser Ala Asn Ala Thr Arg Arg Leu Ser Asp
            340                 345                 350

Arg Ile Gln Ile Ser Leu Gln Gly Ser Arg Thr Trp Arg Glu Leu Ala
        355                 360                 365

Ser Ser Arg Leu Leu Thr Asn Val Pro Ile Ser Gly Asn Asp Asn Thr
    370                 375                 380

Ser Thr Leu Phe Ala Ser Ala Thr Phe Arg Pro Asn Arg Arg Leu Ser
385                 390                 395                 400

Phe Val Leu Gly Ala Gly Leu Gln Arg Arg Thr Ser Asn Thr Gln Leu
                405                 410                 415

Tyr Ser Tyr Ser Ser Lys Arg Ile Asn Leu Ser Thr Ser Leu Ser Leu
            420                 425                 430


<210> SEQ ID NO 20
<211> LENGTH: 918
<212> TYPE: DNA
<213> ORGANISM: Sphingomonas sp. ATCC53159
<220> FEATURE:
<221> NAME/KEY: CDS
<222> LOCATION: (1)..(918)

<400> SEQUENCE: 20

atg cat atc aag aat cgc ttc gtg aat atc tcg acg ttg gcc atc gcc       48
Met His Ile Lys Asn Arg Phe Val Asn Ile Ser Thr Leu Ala Ile Ala
1               5                   10                  15

gcc gcg ctg gcc acg ccg gcg gcg gcg cag atc ccc acg cgg tcc gtg       96
Ala Ala Leu Ala Thr Pro Ala Ala Ala Gln Ile Pro Thr Arg Ser Val
            20                  25                  30

ccc gcg ccg gcc cgc ccg cgg cct gca acg ccg ccg gcg caa cag cag      144
Pro Ala Pro Ala Arg Pro Arg Pro Ala Thr Pro Pro Ala Gln Gln Gln
        35                  40                  45

aac cag gcg ccg tcg acg ccc gca gcg gca acc ccg gcg cag acc gcc      192
Asn Gln Ala Pro Ser Thr Pro Ala Ala Ala Thr Pro Ala Gln Thr Ala
    50                  55                  60

gca acc gtt gcc cct gca gca acc gca ccc gca ggt tac aaa atc ggc      240
Ala Thr Val Ala Pro Ala Ala Thr Ala Pro Ala Gly Tyr Lys Ile Gly
65                  70                  75                  80

gtg gac gac gtg atc gag gcc gac gtg ctc ggc cag acc gac ttc aag      288
Val Asp Asp Val Ile Glu Ala Asp Val Leu Gly Gln Thr Asp Phe Lys
```

```
                85                  90                  95

acg cgc gcc cgt gtg cag gcg gac ggc acg gtg acc ctg ccc tat ctg      336
Thr Arg Ala Arg Val Gln Ala Asp Gly Thr Val Thr Leu Pro Tyr Leu
            100                 105                 110

ggc gcc gtg cag gtc aag ggc gag acc gcg acc tcg ctc gcc gaa aag      384
Gly Ala Val Gln Val Lys Gly Glu Thr Ala Thr Ser Leu Ala Glu Lys
        115                 120                 125

ctg gcc ggg ctg ctg cgc gcc ggc ggc tat tat gcc aag ccg atc gtc      432
Leu Ala Gly Leu Leu Arg Ala Gly Gly Tyr Tyr Ala Lys Pro Ile Val
    130                 135                 140

agc gtc gaa atc gtc ggt ttc gtc agc aac tat gtg acg gtg ctg ggc      480
Ser Val Glu Ile Val Gly Phe Val Ser Asn Tyr Val Thr Val Leu Gly
145                 150                 155                 160

cag gtg aac agt tcc ggc ctg cag ccg gtc gac cgc ggc tat cac gtt      528
Gln Val Asn Ser Ser Gly Leu Gln Pro Val Asp Arg Gly Tyr His Val
                165                 170                 175

tcc gag atc atc gcc cgt gcc ggc ggc ctg cgc ccc gaa gcg gcc gat      576
Ser Glu Ile Ile Ala Arg Ala Gly Gly Leu Arg Pro Glu Ala Ala Asp
            180                 185                 190

ttc gtc gtt ctc acc cgc gcc gat ggc tcc agc gcc aag ctg gac tac      624
Phe Val Val Leu Thr Arg Ala Asp Gly Ser Ser Ala Lys Leu Asp Tyr
        195                 200                 205

aag aag ctc gcc caa ggt ggc ccc aat gac gat ccg atg gtg acg ccc      672
Lys Lys Leu Ala Gln Gly Gly Pro Asn Asp Asp Pro Met Val Thr Pro
    210                 215                 220

ggg gac aag gtc ttt gtc ccg gaa gtc gag cat ttc tac att tat ggt      720
Gly Asp Lys Val Phe Val Pro Glu Val Glu His Phe Tyr Ile Tyr Gly
225                 230                 235                 240

caa att aac gcg cct ggc gta tac gcg att cga tcg gac atg acg ctc      768
Gln Ile Asn Ala Pro Gly Val Tyr Ala Ile Arg Ser Asp Met Thr Leu
                245                 250                 255

cgt cgc gcg ctg gcc cag ggc ggt ggg ctt gcc ccc gca ggc tcc gtc      816
Arg Arg Ala Leu Ala Gln Gly Gly Gly Leu Ala Pro Ala Gly Ser Val
            260                 265                 270

aag cgt gtg aag gtc acg cgg gat ggc aat gaa ctc aag ttg aag ctg      864
Lys Arg Val Lys Val Thr Arg Asp Gly Asn Glu Leu Lys Leu Lys Leu
        275                 280                 285

gac gat ccg att ctc cca ggc gac acg atc gtc atc ggc gaa cga ttg      912
Asp Asp Pro Ile Leu Pro Gly Asp Thr Ile Val Ile Gly Glu Arg Leu
    290                 295                 300

ttc tga                                                              918
Phe
305


<210> SEQ ID NO 21
<211> LENGTH: 305
<212> TYPE: PRT
<213> ORGANISM: Sphingomonas sp. ATCC53159

<400> SEQUENCE: 21

Met His Ile Lys Asn Arg Phe Val Asn Ile Ser Thr Leu Ala Ile Ala
1               5                   10                  15

Ala Ala Leu Ala Thr Pro Ala Ala Ala Gln Ile Pro Thr Arg Ser Val
            20                  25                  30

Pro Ala Pro Ala Arg Pro Arg Pro Ala Thr Pro Pro Ala Gln Gln Gln
        35                  40                  45

Asn Gln Ala Pro Ser Thr Pro Ala Ala Ala Thr Pro Ala Gln Thr Ala
    50                  55                  60

Ala Thr Val Ala Pro Ala Ala Thr Ala Pro Ala Gly Tyr Lys Ile Gly
```

```
65                  70                  75                  80

Val Asp Asp Val Ile Glu Ala Asp Val Leu Gly Gln Thr Asp Phe Lys
                85                  90                  95

Thr Arg Ala Arg Val Gln Ala Asp Gly Thr Val Thr Leu Pro Tyr Leu
            100                 105                 110

Gly Ala Val Gln Val Lys Gly Glu Thr Ala Thr Ser Leu Ala Glu Lys
        115                 120                 125

Leu Ala Gly Leu Leu Arg Ala Gly Gly Tyr Tyr Ala Lys Pro Ile Val
    130                 135                 140

Ser Val Glu Ile Val Gly Phe Val Ser Asn Tyr Val Thr Val Leu Gly
145                 150                 155                 160

Gln Val Asn Ser Ser Gly Leu Gln Pro Val Asp Arg Gly Tyr His Val
                165                 170                 175

Ser Glu Ile Ile Ala Arg Ala Gly Gly Leu Arg Pro Glu Ala Ala Asp
            180                 185                 190

Phe Val Val Leu Thr Arg Ala Asp Gly Ser Ser Ala Lys Leu Asp Tyr
        195                 200                 205

Lys Lys Leu Ala Gln Gly Gly Pro Asn Asp Asp Pro Met Val Thr Pro
    210                 215                 220

Gly Asp Lys Val Phe Val Pro Glu Val Glu His Phe Tyr Ile Tyr Gly
225                 230                 235                 240

Gln Ile Asn Ala Pro Gly Val Tyr Ala Ile Arg Ser Asp Met Thr Leu
                245                 250                 255

Arg Arg Ala Leu Ala Gln Gly Gly Gly Leu Ala Pro Ala Gly Ser Val
            260                 265                 270

Lys Arg Val Lys Val Thr Arg Asp Gly Asn Glu Leu Lys Leu Lys Leu
        275                 280                 285

Asp Asp Pro Ile Leu Pro Gly Asp Thr Ile Val Ile Gly Glu Arg Leu
    290                 295                 300

Phe
305


<210> SEQ ID NO 22
<211> LENGTH: 1347
<212> TYPE: DNA
<213> ORGANISM: Sphingomonas sp. ATCC53159
<220> FEATURE:
<221> NAME/KEY: CDS
<222> LOCATION: (1)..(1347)

<400> SEQUENCE: 22

gtg aat atc att cag ttc ttc cgc att ctg tgg gtg cgc cga tgg atc       48
Val Asn Ile Ile Gln Phe Phe Arg Ile Leu Trp Val Arg Arg Trp Ile
1               5                   10                  15

atc ctc ccg gcg ttt ctc gtt tgc gtt acc act gcc acc att gtg gtc       96
Ile Leu Pro Ala Phe Leu Val Cys Val Thr Thr Ala Thr Ile Val Val
            20                  25                  30

cag ttt ctg ccc gaa cgc tac aag gcc act acg cgg gtg gtg ctc gac      144
Gln Phe Leu Pro Glu Arg Tyr Lys Ala Thr Thr Arg Val Val Leu Asp
        35                  40                  45

acg ttt aag ccc gat ccc gtc acc gga cag gtg atg agc tcg cag ttc      192
Thr Phe Lys Pro Asp Pro Val Thr Gly Gln Val Met Ser Ser Gln Phe
    50                  55                  60

atg cgc gcc tat gtc gag act cag acc cag ctg atc gag gac tat gcg      240
Met Arg Ala Tyr Val Glu Thr Gln Thr Gln Leu Ile Glu Asp Tyr Ala
65                  70                  75                  80

acc gcc ggt cgc gtg gtc gac gaa ctg ggc tgg gtg aat gat ccg gcg      288
```

```
Thr Ala Gly Arg Val Val Asp Glu Leu Gly Trp Val Asn Asp Pro Ala
                85                  90                  95

aac atc tcc gcg ttc aac aac tcg tcc gcg gct gcc acc ggc gac atc      336
Asn Ile Ser Ala Phe Asn Asn Ser Ser Ala Ala Ala Thr Gly Asp Ile
            100                 105                 110

cgc cgc tgg ctc gcc aag cag atc atc gac aat acc aag gcc gat gtg      384
Arg Arg Trp Leu Ala Lys Gln Ile Ile Asp Asn Thr Lys Ala Asp Val
        115                 120                 125

atg gag ggg agc aac atc ctc gaa atc acc tat tcg gac agc tcg ccc      432
Met Glu Gly Ser Asn Ile Leu Glu Ile Thr Tyr Ser Asp Ser Ser Pro
    130                 135                 140

gag cgc gcc gaa cgc atc gcc aac ctg atc cgc acc tcg ttc ctc gcc      480
Glu Arg Ala Glu Arg Ile Ala Asn Leu Ile Arg Thr Ser Phe Leu Ala
145                 150                 155                 160

cag tcg ctc gcc gcc aag cgc cag gcc gcg acc aag tcg gcc gac tgg      528
Gln Ser Leu Ala Ala Lys Arg Gln Ala Ala Thr Lys Ser Ala Asp Trp
                165                 170                 175

tac gcc cag cag gcc gaa gct gcc cgc gat tcg ctc gct gcg gcg gtc      576
Tyr Ala Gln Gln Ala Glu Ala Ala Arg Asp Ser Leu Ala Ala Ala Val
            180                 185                 190

cag gcc cgc acc gat ttc gtg aag aag acc ggc atc gtg ctg acc gaa      624
Gln Ala Arg Thr Asp Phe Val Lys Lys Thr Gly Ile Val Leu Thr Glu
        195                 200                 205

acc ggc gcc gac ctg gaa acc cag aag ctc cag cag atc gag ggg cag      672
Thr Gly Ala Asp Leu Glu Thr Gln Lys Leu Gln Gln Ile Glu Gly Gln
    210                 215                 220

acg acg acc gcc acc gcc ccg gtt gcc atg gcc ccc agc ggc atg ggc      720
Thr Thr Thr Ala Thr Ala Pro Val Ala Met Ala Pro Ser Gly Met Gly
225                 230                 235                 240

ccg gcg cag atg cag ctc gcc cag atc gac cag cag atc cag cag gca      768
Pro Ala Gln Met Gln Leu Ala Gln Ile Asp Gln Gln Ile Gln Gln Ala
                245                 250                 255

gcg acc agc cta ggt ccg aac cac cca act ttc cag gcc ttg cag cgg      816
Ala Thr Ser Leu Gly Pro Asn His Pro Thr Phe Gln Ala Leu Gln Arg
            260                 265                 270

cag cgc gaa gtg ttc gcc aag gca gcg gcg gcg gaa cgc gcg cag gcg      864
Gln Arg Glu Val Phe Ala Lys Ala Ala Ala Ala Glu Arg Ala Gln Ala
        275                 280                 285

aac ggc gta tcc ggt ccg gca cgc ggg gcc atc gaa agc gca gcc aac      912
Asn Gly Val Ser Gly Pro Ala Arg Gly Ala Ile Glu Ser Ala Ala Asn
    290                 295                 300

gcc cag cgc gcg cgg gtt ctc ggc aat cgt cag gat gtc gac aag ctt      960
Ala Gln Arg Ala Arg Val Leu Gly Asn Arg Gln Asp Val Asp Lys Leu
305                 310                 315                 320

acg cag ctg cag cgt gac gtc tcg ctg aag cag gat cag tac atg aag     1008
Thr Gln Leu Gln Arg Asp Val Ser Leu Lys Gln Asp Gln Tyr Met Lys
                325                 330                 335

gcg gca cag cgc gtc gcc gat ctg cgg ctg gaa gca agc agc aac gat     1056
Ala Ala Gln Arg Val Ala Asp Leu Arg Leu Glu Ala Ser Ser Asn Asp
            340                 345                 350

gtc ggc atg tcg acg ctc agc gaa gca tcg gcg ccg gaa acg ccc tat     1104
Val Gly Met Ser Thr Leu Ser Glu Ala Ser Ala Pro Glu Thr Pro Tyr
        355                 360                 365

tac ccc aag gtg ccg ctc atc atc ggt ggt gca gcc ggc ttc ggc ctc     1152
Tyr Pro Lys Val Pro Leu Ile Ile Gly Gly Ala Ala Gly Phe Gly Leu
    370                 375                 380

ggg ctc ggt ctg ctg gtc gcg ctg ctc gtc gag ctg ctc ggc cgc cgc     1200
Gly Leu Gly Leu Leu Val Ala Leu Leu Val Glu Leu Leu Gly Arg Arg
385                 390                 395                 400
```

```
gtc cgc agc ccc gag gat ctg gaa gtt gcg atc gat gca ccg gtg ctg     1248
Val Arg Ser Pro Glu Asp Leu Glu Val Ala Ile Asp Ala Pro Val Leu
                405                 410                 415

ggc gtg atc cag agc cgc gcc tcg ctt gcc gcc cgc ctt cgc cgc gcc     1296
Gly Val Ile Gln Ser Arg Ala Ser Leu Ala Ala Arg Leu Arg Arg Ala
            420                 425                 430

caa gaa acc ctc ggc gaa ggt gcc gac acg cac gga gct tca gta aac     1344
Gln Glu Thr Leu Gly Glu Gly Ala Asp Thr His Gly Ala Ser Val Asn
        435                 440                 445

tga                                                                 1347


<210> SEQ ID NO 23
<211> LENGTH: 448
<212> TYPE: PRT
<213> ORGANISM: Sphingomonas sp. ATCC53159

<400> SEQUENCE: 23

Val Asn Ile Ile Gln Phe Phe Arg Ile Leu Trp Val Arg Arg Trp Ile
1               5                   10                  15

Ile Leu Pro Ala Phe Leu Val Cys Val Thr Thr Ala Thr Ile Val Val
            20                  25                  30

Gln Phe Leu Pro Glu Arg Tyr Lys Ala Thr Thr Arg Val Val Leu Asp
        35                  40                  45

Thr Phe Lys Pro Asp Pro Val Thr Gly Gln Val Met Ser Ser Gln Phe
    50                  55                  60

Met Arg Ala Tyr Val Glu Thr Gln Thr Gln Leu Ile Glu Asp Tyr Ala
65                  70                  75                  80

Thr Ala Gly Arg Val Val Asp Glu Leu Gly Trp Val Asn Asp Pro Ala
                85                  90                  95

Asn Ile Ser Ala Phe Asn Asn Ser Ser Ala Ala Ala Thr Gly Asp Ile
            100                 105                 110

Arg Arg Trp Leu Ala Lys Gln Ile Ile Asp Asn Thr Lys Ala Asp Val
        115                 120                 125

Met Glu Gly Ser Asn Ile Leu Glu Ile Thr Tyr Ser Asp Ser Ser Pro
    130                 135                 140

Glu Arg Ala Glu Arg Ile Ala Asn Leu Ile Arg Thr Ser Phe Leu Ala
145                 150                 155                 160

Gln Ser Leu Ala Ala Lys Arg Gln Ala Ala Thr Lys Ser Ala Asp Trp
                165                 170                 175

Tyr Ala Gln Gln Ala Glu Ala Ala Arg Asp Ser Leu Ala Ala Ala Val
            180                 185                 190

Gln Ala Arg Thr Asp Phe Val Lys Lys Thr Gly Ile Val Leu Thr Glu
        195                 200                 205

Thr Gly Ala Asp Leu Glu Thr Gln Lys Leu Gln Gln Ile Glu Gly Gln
    210                 215                 220

Thr Thr Thr Ala Thr Ala Pro Val Ala Met Ala Pro Ser Gly Met Gly
225                 230                 235                 240

Pro Ala Gln Met Gln Leu Ala Gln Ile Asp Gln Gln Ile Gln Gln Ala
                245                 250                 255

Ala Thr Ser Leu Gly Pro Asn His Pro Thr Phe Gln Ala Leu Gln Arg
            260                 265                 270

Gln Arg Glu Val Phe Ala Lys Ala Ala Ala Ala Glu Arg Ala Gln Ala
        275                 280                 285

Asn Gly Val Ser Gly Pro Ala Arg Gly Ala Ile Glu Ser Ala Ala Asn
    290                 295                 300
```

```
Ala Gln Arg Ala Arg Val Leu Gly Asn Arg Gln Asp Val Asp Lys Leu
305                 310                 315                 320

Thr Gln Leu Gln Arg Asp Val Ser Leu Lys Gln Asp Gln Tyr Met Lys
                325                 330                 335

Ala Ala Gln Arg Val Ala Asp Leu Arg Leu Glu Ala Ser Ser Asn Asp
            340                 345                 350

Val Gly Met Ser Thr Leu Ser Glu Ala Ser Ala Pro Glu Thr Pro Tyr
        355                 360                 365

Tyr Pro Lys Val Pro Leu Ile Ile Gly Gly Ala Ala Gly Phe Gly Leu
    370                 375                 380

Gly Leu Gly Leu Leu Val Ala Leu Leu Val Glu Leu Leu Gly Arg Arg
385                 390                 395                 400

Val Arg Ser Pro Glu Asp Leu Glu Val Ala Ile Asp Ala Pro Val Leu
                405                 410                 415

Gly Val Ile Gln Ser Arg Ala Ser Leu Ala Ala Arg Leu Arg Arg Ala
            420                 425                 430

Gln Glu Thr Leu Gly Glu Gly Ala Asp Thr His Gly Ala Ser Val Asn
        435                 440                 445


<210> SEQ ID NO 24
<211> LENGTH: 708
<212> TYPE: DNA
<213> ORGANISM: Sphingomonas sp. ATCC53159
<220> FEATURE:
<221> NAME/KEY: CDS
<222> LOCATION: (1)..(708)

<400> SEQUENCE: 24

atg gac gcg atg acc agc gaa ccg ctg ccc gaa ggc gat cgt ccg agc       48
Met Asp Ala Met Thr Ser Glu Pro Leu Pro Glu Gly Asp Arg Pro Ser
1               5                   10                  15

gcc gtg ccg acc acg ccg gat acg atc ggc atg ctc gaa tac cag ctc       96
Ala Val Pro Thr Thr Pro Asp Thr Ile Gly Met Leu Glu Tyr Gln Leu
            20                  25                  30

gtc ctc tcc gat ccg acc ggg atc gag gcg gaa gcg atc cgc gcg cta      144
Val Leu Ser Asp Pro Thr Gly Ile Glu Ala Glu Ala Ile Arg Ala Leu
        35                  40                  45

cgc acg cgc atc atg acc cag cac ctc cgc gag ggc cgg cgc gcg ctc      192
Arg Thr Arg Ile Met Thr Gln His Leu Arg Glu Gly Arg Arg Ala Leu
    50                  55                  60

gcg atc tgc gcc gcc tcg gcg gga tcc ggc tgc agc ttc acc gcc gtc      240
Ala Ile Cys Ala Ala Ser Ala Gly Ser Gly Cys Ser Phe Thr Ala Val
65                  70                  75                  80

aat ctg gcg acg gcg ctg gcg cag atc ggc gtt aag act gcg ctg gtc      288
Asn Leu Ala Thr Ala Leu Ala Gln Ile Gly Val Lys Thr Ala Leu Val
                85                  90                  95

gat gcc aat ctg cgc gat ccc agc atc ggc gca gcc ttc ggc ctc gcc      336
Asp Ala Asn Leu Arg Asp Pro Ser Ile Gly Ala Ala Phe Gly Leu Ala
            100                 105                 110

gcc gac aag ccc ggc ctg gcc gat tat ctc gcc tcg ggc gat gtc gac      384
Ala Asp Lys Pro Gly Leu Ala Asp Tyr Leu Ala Ser Gly Asp Val Asp
        115                 120                 125

ctc gcc tcg atc atc cat gcg acc cgc ctc gac cag ctc tcg atc atc      432
Leu Ala Ser Ile Ile His Ala Thr Arg Leu Asp Gln Leu Ser Ile Ile
    130                 135                 140

ccg gcc ggg cat gtc gag cac agc ccg cag gaa ctg ctc gcg tcc gaa      480
Pro Ala Gly His Val Glu His Ser Pro Gln Glu Leu Leu Ala Ser Glu
145                 150                 155                 160

cag ttc cat gat ctg gcg acg cag ctg ctg cgc gag ttc gac atc acg      528
```

```
Gln Phe His Asp Leu Ala Thr Gln Leu Leu Arg Glu Phe Asp Ile Thr
                165                 170                 175

atc ttc gac acc acg gcg tcc aac acc tgc gcc gac gcg cag cgt gtc      576
Ile Phe Asp Thr Thr Ala Ser Asn Thr Cys Ala Asp Ala Gln Arg Val
            180                 185                 190

gcg cat atc gcc ggc tat gcg atc atc gtg gcg cgc aag gat gcg agc      624
Ala His Ile Ala Gly Tyr Ala Ile Ile Val Ala Arg Lys Asp Ala Ser
        195                 200                 205

tac atc cgc gac gtg aac acg ctc agc cgc acg ctg cgt gca gac cgc      672
Tyr Ile Arg Asp Val Asn Thr Leu Ser Arg Thr Leu Arg Ala Asp Arg
    210                 215                 220

acc aac gtc atc ggc tgc gta ctg aac ggc tat tga                      708
Thr Asn Val Ile Gly Cys Val Leu Asn Gly Tyr
225                 230                 235


<210> SEQ ID NO 25
<211> LENGTH: 235
<212> TYPE: PRT
<213> ORGANISM: Sphingomonas sp. ATCC53159

<400> SEQUENCE: 25

Met Asp Ala Met Thr Ser Glu Pro Leu Pro Glu Gly Asp Arg Pro Ser
1               5                   10                  15

Ala Val Pro Thr Thr Pro Asp Thr Ile Gly Met Leu Glu Tyr Gln Leu
            20                  25                  30

Val Leu Ser Asp Pro Thr Gly Ile Glu Ala Glu Ala Ile Arg Ala Leu
        35                  40                  45

Arg Thr Arg Ile Met Thr Gln His Leu Arg Glu Gly Arg Arg Ala Leu
    50                  55                  60

Ala Ile Cys Ala Ala Ser Ala Gly Ser Gly Cys Ser Phe Thr Ala Val
65                  70                  75                  80

Asn Leu Ala Thr Ala Leu Ala Gln Ile Gly Val Lys Thr Ala Leu Val
                85                  90                  95

Asp Ala Asn Leu Arg Asp Pro Ser Ile Gly Ala Ala Phe Gly Leu Ala
            100                 105                 110

Ala Asp Lys Pro Gly Leu Ala Asp Tyr Leu Ala Ser Gly Asp Val Asp
        115                 120                 125

Leu Ala Ser Ile Ile His Ala Thr Arg Leu Asp Gln Leu Ser Ile Ile
    130                 135                 140

Pro Ala Gly His Val Glu His Ser Pro Gln Glu Leu Leu Ala Ser Glu
145                 150                 155                 160

Gln Phe His Asp Leu Ala Thr Gln Leu Leu Arg Glu Phe Asp Ile Thr
                165                 170                 175

Ile Phe Asp Thr Thr Ala Ser Asn Thr Cys Ala Asp Ala Gln Arg Val
            180                 185                 190

Ala His Ile Ala Gly Tyr Ala Ile Ile Val Ala Arg Lys Asp Ala Ser
        195                 200                 205

Tyr Ile Arg Asp Val Asn Thr Leu Ser Arg Thr Leu Arg Ala Asp Arg
    210                 215                 220

Thr Asn Val Ile Gly Cys Val Leu Asn Gly Tyr
225                 230                 235


<210> SEQ ID NO 26
<211> LENGTH: 882
<212> TYPE: DNA
<213> ORGANISM: Sphingomonas sp. ATCC53159
<220> FEATURE:
<221> NAME/KEY: CDS
```

<222> LOCATION: (1)..(882)

<400> SEQUENCE: 26

```
atg gca gcg acc gcg atg acg cgg cag cag gag agg aag ggc ggt ggc      48
Met Ala Ala Thr Ala Met Thr Arg Gln Gln Glu Arg Lys Gly Gly Gly
1               5                   10                  15

tat tgg ctg gcc gtt gcc ggt ctt gcc gcg cta acc atc ccg acc ttc      96
Tyr Trp Leu Ala Val Ala Gly Leu Ala Ala Leu Thr Ile Pro Thr Phe
            20                  25                  30

atc acc ctg ggt cgc gag gtt tgg agt gcg gaa ggc ggc gtg cag ggt     144
Ile Thr Leu Gly Arg Glu Val Trp Ser Ala Glu Gly Gly Val Gln Gly
        35                  40                  45

ccg atc gtg ctc gcc acg ggc gcc tgg atg ctg gcc cgc cag tgc tcg     192
Pro Ile Val Leu Ala Thr Gly Ala Trp Met Leu Ala Arg Gln Cys Ser
    50                  55                  60

acg atc gag gcg cta cgc cgc ccc ggc agc gtg ctg ctc ggc gcg ctg     240
Thr Ile Glu Ala Leu Arg Arg Pro Gly Ser Val Leu Leu Gly Ala Leu
65                  70                  75                  80

ttc ctg ctg gcg acg ctt gcc ttc tac acc gtt gga cgg gtg ttc gac     288
Phe Leu Leu Ala Thr Leu Ala Phe Tyr Thr Val Gly Arg Val Phe Asp
                85                  90                  95

ttc atc agt gtc gaa acc ttc gga ctg gtc gcg acc tat ctg gtc gtc     336
Phe Ile Ser Val Glu Thr Phe Gly Leu Val Ala Thr Tyr Leu Val Val
            100                 105                 110

gcc tat ctc tat ttc ggt gcc agg gtg ctc cgt gcc gcc tgg ttc ccg     384
Ala Tyr Leu Tyr Phe Gly Ala Arg Val Leu Arg Ala Ala Trp Phe Pro
        115                 120                 125

gtg ctg tgg ctg ttc ttc ctg gtg ccg ccg ccc ggc tgg gcc gtc gac     432
Val Leu Trp Leu Phe Phe Leu Val Pro Pro Pro Gly Trp Ala Val Asp
    130                 135                 140

cgc atc acc gca ccg ctc aag gag ttc gtc tcc tat gcg gca acg ggc     480
Arg Ile Thr Ala Pro Leu Lys Glu Phe Val Ser Tyr Ala Ala Thr Gly
145                 150                 155                 160

ctg ctt tcc tgg gtg gat tat ccg atc ctg cgc cag ggc gtg aca ctg     528
Leu Leu Ser Trp Val Asp Tyr Pro Ile Leu Arg Gln Gly Val Thr Leu
                165                 170                 175

ttc gtc ggc ccc tat cag ctg ctc gtc gaa gat gcc tgt tcg ggt ctg     576
Phe Val Gly Pro Tyr Gln Leu Leu Val Glu Asp Ala Cys Ser Gly Leu
            180                 185                 190

cgc tcg ctg tcc agc ctg gtc gtc gtg acg ctg ctc tac atc tac atc     624
Arg Ser Leu Ser Ser Leu Val Val Val Thr Leu Leu Tyr Ile Tyr Ile
        195                 200                 205

aag aac aag ccg tcc tgg cgc tac gcg gcg ttc atc gca gcg ctg gtg     672
Lys Asn Lys Pro Ser Trp Arg Tyr Ala Ala Phe Ile Ala Ala Leu Val
    210                 215                 220

atc ccg gtg gca gtg gtg acc aac gtc ctg cgg atc atc atc ctg gta     720
Ile Pro Val Ala Val Val Thr Asn Val Leu Arg Ile Ile Ile Leu Val
225                 230                 235                 240

ctg atc acc tat cat ctg ggc gac gag gcg gcg cag agc ttc ctc cac     768
Leu Ile Thr Tyr His Leu Gly Asp Glu Ala Ala Gln Ser Phe Leu His
                245                 250                 255

gtc tcc acc ggc atg gtg atg ttc gtg gtc gcc ctg ctt tgc atc ttc     816
Val Ser Thr Gly Met Val Met Phe Val Val Ala Leu Leu Cys Ile Phe
            260                 265                 270

gcg atc gac tgg gtg gtc gag caa ctt ctt ctc ctg cgt cgg agg cat     864
Ala Ile Asp Trp Val Val Glu Gln Leu Leu Leu Leu Arg Arg Arg His
        275                 280                 285

cat gtt caa ccg gcg tga                                             882
His Val Gln Pro Ala
    290
```

<210> SEQ ID NO 27
<211> LENGTH: 293
<212> TYPE: PRT
<213> ORGANISM: Sphingomonas sp. ATCC53159

<400> SEQUENCE: 27

```
Met Ala Ala Thr Ala Met Thr Arg Gln Gln Glu Arg Lys Gly Gly Gly
1               5                   10                  15

Tyr Trp Leu Ala Val Ala Gly Leu Ala Ala Leu Thr Ile Pro Thr Phe
            20                  25                  30

Ile Thr Leu Gly Arg Glu Val Trp Ser Ala Glu Gly Gly Val Gln Gly
        35                  40                  45

Pro Ile Val Leu Ala Thr Gly Ala Trp Met Leu Ala Arg Gln Cys Ser
    50                  55                  60

Thr Ile Glu Ala Leu Arg Arg Pro Gly Ser Val Leu Leu Gly Ala Leu
65                  70                  75                  80

Phe Leu Leu Ala Thr Leu Ala Phe Tyr Thr Val Gly Arg Val Phe Asp
                85                  90                  95

Phe Ile Ser Val Glu Thr Phe Gly Leu Val Ala Thr Tyr Leu Val Val
            100                 105                 110

Ala Tyr Leu Tyr Phe Gly Ala Arg Val Leu Arg Ala Ala Trp Phe Pro
        115                 120                 125

Val Leu Trp Leu Phe Phe Leu Val Pro Pro Pro Gly Trp Ala Val Asp
    130                 135                 140

Arg Ile Thr Ala Pro Leu Lys Glu Phe Val Ser Tyr Ala Ala Thr Gly
145                 150                 155                 160

Leu Leu Ser Trp Val Asp Tyr Pro Ile Leu Arg Gln Gly Val Thr Leu
                165                 170                 175

Phe Val Gly Pro Tyr Gln Leu Leu Val Glu Asp Ala Cys Ser Gly Leu
            180                 185                 190

Arg Ser Leu Ser Ser Leu Val Val Val Thr Leu Leu Tyr Ile Tyr Ile
        195                 200                 205

Lys Asn Lys Pro Ser Trp Arg Tyr Ala Ala Phe Ile Ala Ala Leu Val
    210                 215                 220

Ile Pro Val Ala Val Val Thr Asn Val Leu Arg Ile Ile Ile Leu Val
225                 230                 235                 240

Leu Ile Thr Tyr His Leu Gly Asp Glu Ala Ala Gln Ser Phe Leu His
                245                 250                 255

Val Ser Thr Gly Met Val Met Phe Val Val Ala Leu Leu Cys Ile Phe
            260                 265                 270

Ala Ile Asp Trp Val Val Glu Gln Leu Leu Leu Leu Arg Arg Arg His
        275                 280                 285

His Val Gln Pro Ala
    290
```

<210> SEQ ID NO 28
<211> LENGTH: 699
<212> TYPE: DNA
<213> ORGANISM: Sphingomonas sp. ATCC53159
<220> FEATURE:
<221> NAME/KEY: CDS
<222> LOCATION: (1)..(699)

<400> SEQUENCE: 28

```
atg ttc aac cgg cgt gac ctg ctg atc ggc gca ggc tgc ttc gcc gcc       48
Met Phe Asn Arg Arg Asp Leu Leu Ile Gly Ala Gly Cys Phe Ala Ala
```

```
1               5                   10                  15

gct ggc gcc tcg ctc ggc ctg aag ccg cac cgg cgg atg gac ctg ctg       96
Ala Gly Ala Ser Leu Gly Leu Lys Pro His Arg Arg Met Asp Leu Leu
            20                  25                  30

ggc ggc acc aag ctc gac acg ctg atg ccc aag gca ttc ggc gca tgg      144
Gly Gly Thr Lys Leu Asp Thr Leu Met Pro Lys Ala Phe Gly Ala Trp
        35                  40                  45

aag gca gag gat acc ggt tcg ctg atc gcg ccg gcg cgc gaa ggc agc      192
Lys Ala Glu Asp Thr Gly Ser Leu Ile Ala Pro Ala Arg Glu Gly Ser
    50                  55                  60

ctg gag gac aag ctc tac aac cag gtg gtc acc cgc gcc ttc tcc cgc      240
Leu Glu Asp Lys Leu Tyr Asn Gln Val Val Thr Arg Ala Phe Ser Arg
65                  70                  75                  80

gcg gac ggt gcc caa gtg atg ctg ctg atc gcc tat ggc aac gcc cag      288
Ala Asp Gly Ala Gln Val Met Leu Leu Ile Ala Tyr Gly Asn Ala Gln
                85                  90                  95

acc gat cta ctg cag ctg cac cgg ccg gaa ata tgc tac ccg ttc ttc      336
Thr Asp Leu Leu Gln Leu His Arg Pro Glu Ile Cys Tyr Pro Phe Phe
            100                 105                 110

ggc ttc acc gtg gtg gaa agc cat gag cag acc atc ccg gtg acg ccg      384
Gly Phe Thr Val Val Glu Ser His Glu Gln Thr Ile Pro Val Thr Pro
        115                 120                 125

cag gtg acg atc ccc ggt cgc gcg ctg acc gcc acc aac ttc aac cgc      432
Gln Val Thr Ile Pro Gly Arg Ala Leu Thr Ala Thr Asn Phe Asn Arg
    130                 135                 140

acc gag cag atc ctc tac tgg acc cgc gtc ggc gaa tat ctg ccg cag      480
Thr Glu Gln Ile Leu Tyr Trp Thr Arg Val Gly Glu Tyr Leu Pro Gln
145                 150                 155                 160

aac ggc aat cag cag atg ctc gcg cgg ctg aag agc cag gtc cag ggc      528
Asn Gly Asn Gln Gln Met Leu Ala Arg Leu Lys Ser Gln Val Gln Gly
                165                 170                 175

tgg atc gtc gac ggt gtg ctg gtg cgc atc tcg acg gtg acg ccc gag      576
Trp Ile Val Asp Gly Val Leu Val Arg Ile Ser Thr Val Thr Pro Glu
            180                 185                 190

gcg gaa gat ggc ctg agc gcc aat ctc gat ttc gcg cgc gag ctg gtg      624
Ala Glu Asp Gly Leu Ser Ala Asn Leu Asp Phe Ala Arg Glu Leu Val
        195                 200                 205

aag acg ctc gac ccg cgc gtg ctg cgc ccg ctg ctc ggg aac ggg ctc      672
Lys Thr Leu Asp Pro Arg Val Leu Arg Pro Leu Leu Gly Asn Gly Leu
    210                 215                 220

aca cgg cag ctc ggt cac cag gtc tga                                  699
Thr Arg Gln Leu Gly His Gln Val
225                 230


<210> SEQ ID NO 29
<211> LENGTH: 232
<212> TYPE: PRT
<213> ORGANISM: Sphingomonas sp. ATCC53159

<400> SEQUENCE: 29

Met Phe Asn Arg Arg Asp Leu Leu Ile Gly Ala Gly Cys Phe Ala Ala
1               5                   10                  15

Ala Gly Ala Ser Leu Gly Leu Lys Pro His Arg Arg Met Asp Leu Leu
            20                  25                  30

Gly Gly Thr Lys Leu Asp Thr Leu Met Pro Lys Ala Phe Gly Ala Trp
        35                  40                  45

Lys Ala Glu Asp Thr Gly Ser Leu Ile Ala Pro Ala Arg Glu Gly Ser
    50                  55                  60

Leu Glu Asp Lys Leu Tyr Asn Gln Val Val Thr Arg Ala Phe Ser Arg
```

```
65                  70                  75                  80

Ala Asp Gly Ala Gln Val Met Leu Leu Ile Ala Tyr Gly Asn Ala Gln
                85                  90                  95

Thr Asp Leu Leu Gln Leu His Arg Pro Glu Ile Cys Tyr Pro Phe Phe
            100                 105                 110

Gly Phe Thr Val Val Glu Ser His Glu Gln Thr Ile Pro Val Thr Pro
        115                 120                 125

Gln Val Thr Ile Pro Gly Arg Ala Leu Thr Ala Thr Asn Phe Asn Arg
    130                 135                 140

Thr Glu Gln Ile Leu Tyr Trp Thr Arg Val Gly Glu Tyr Leu Pro Gln
145                 150                 155                 160

Asn Gly Asn Gln Gln Met Leu Ala Arg Leu Lys Ser Gln Val Gln Gly
                165                 170                 175

Trp Ile Val Asp Gly Val Leu Val Arg Ile Ser Thr Val Thr Pro Glu
            180                 185                 190

Ala Glu Asp Gly Leu Ser Ala Asn Leu Asp Phe Ala Arg Glu Leu Val
        195                 200                 205

Lys Thr Leu Asp Pro Arg Val Leu Arg Pro Leu Leu Gly Asn Gly Leu
    210                 215                 220

Thr Arg Gln Leu Gly His Gln Val
225                 230


<210> SEQ ID NO 30
<211> LENGTH: 1395
<212> TYPE: DNA
<213> ORGANISM: Sphingomonas sp. ATCC53159
<220> FEATURE:
<221> NAME/KEY: CDS
<222> LOCATION: (1)..(1395)

<400> SEQUENCE: 30

atg aac gcc gtt gtt ccg atg cgc cgc ggc ggc ccg ctc gcc cgc atg       48
Met Asn Ala Val Val Pro Met Arg Arg Gly Gly Pro Leu Ala Arg Met
1               5                   10                  15

cgc gat acc gtg ctg cct gcc cgc gtc gac gct tat gac acc gcc ttc       96
Arg Asp Thr Val Leu Pro Ala Arg Val Asp Ala Tyr Asp Thr Ala Phe
            20                  25                  30

ctg cct gcc gcg ctg gag atc atc gag cgg ccg gtt tcg ccc acc gcg      144
Leu Pro Ala Ala Leu Glu Ile Ile Glu Arg Pro Val Ser Pro Thr Ala
        35                  40                  45

cgg ctt acc gcc aag gtg atg ctg gcc ggg ctg gcg atc acc gcc gcc      192
Arg Leu Thr Ala Lys Val Met Leu Ala Gly Leu Ala Ile Thr Ala Ala
    50                  55                  60

tgg ctg gcg atc ggc aag gtc gaa gtc gtc gcg ccg acg cag ggg cgg      240
Trp Leu Ala Ile Gly Lys Val Glu Val Val Ala Pro Thr Gln Gly Arg
65                  70                  75                  80

atc gcg ccg atc ggc gag acc aag atc gtc cag tcg ccc gaa tcg ggg      288
Ile Ala Pro Ile Gly Glu Thr Lys Ile Val Gln Ser Pro Glu Ser Gly
                85                  90                  95

atc gtc cgc cgc atc ctg gtg ggc gag ggg cag aag gtc gcc aag ggc      336
Ile Val Arg Arg Ile Leu Val Gly Glu Gly Gln Lys Val Ala Lys Gly
            100                 105                 110

cag gtg ctg atc acg ctc gac ccg acc gtg tcg tcg gcg gag gcg gca      384
Gln Val Leu Ile Thr Leu Asp Pro Thr Val Ser Ser Ala Glu Ala Ala
        115                 120                 125

cag gcg aag gtg gcg ctg ctc agc gcc cag ctc gac gcc gca cgc aac      432
Gln Ala Lys Val Ala Leu Leu Ser Ala Gln Leu Asp Ala Ala Arg Asn
    130                 135                 140
```

```
cag gcg atc atc gac gcg ctg gac ggc agg ggc ttc cgc ttc gtc gcg      480
Gln Ala Ile Ile Asp Ala Leu Asp Gly Arg Gly Phe Arg Phe Val Ala
145                 150                 155                 160

cct gcc gcc gcc agc ccg ggc gaa gtg gcg acg cat cgc ggc ctc gcc      528
Pro Ala Ala Ala Ser Pro Gly Glu Val Ala Thr His Arg Gly Leu Ala
                165                 170                 175

cgc gcc cgg ctg ggc cag atc gag gcg gcg ctg gcc ggc ggc cgc tcc      576
Arg Ala Arg Leu Gly Gln Ile Glu Ala Ala Leu Ala Gly Gly Arg Ser
            180                 185                 190

gat cgc ggt gcc gcc gtc tcg gcc gcg gcc gag gcg cag gca cag gtg      624
Asp Arg Gly Ala Ala Val Ser Ala Ala Ala Glu Ala Gln Ala Gln Val
        195                 200                 205

cgg aag ctc gaa cag tcg ctg ccg ctg ctc gaa cag cag atc gcc gcg      672
Arg Lys Leu Glu Gln Ser Leu Pro Leu Leu Glu Gln Gln Ile Ala Ala
    210                 215                 220

aac gag acg atg gcc gcc aag ggc tat gtc tcg aag ctg cgc gtc gtg      720
Asn Glu Thr Met Ala Ala Lys Gly Tyr Val Ser Lys Leu Arg Val Val
225                 230                 235                 240

gag atg cgt cgc cag ctg atc gcc gag cgg cag gac ctg acg gcg gcg      768
Glu Met Arg Arg Gln Leu Ile Ala Glu Arg Gln Asp Leu Thr Ala Ala
                245                 250                 255

cgc gct acg ctc gcc aaa ctc ggc cag cag tcg ctg agc gtc tcc agc      816
Arg Ala Thr Leu Ala Lys Leu Gly Gln Gln Ser Leu Ser Val Ser Ser
            260                 265                 270

ctg tcg gcc aag acg cgc gag gag gcg cgg gcg cag gtg ctg cag gat      864
Leu Ser Ala Lys Thr Arg Glu Glu Ala Arg Ala Gln Val Leu Gln Asp
        275                 280                 285

ctg gtc aag gcg cag gac gag gtg cgt gcc cgc ggc gag gac gtc gcc      912
Leu Val Lys Ala Gln Asp Glu Val Arg Ala Arg Gly Glu Asp Val Ala
    290                 295                 300

aag gcg aat ctg cgc agc tcg ttc cgc gaa ctg cgc gcg ccg gtg agc      960
Lys Ala Asn Leu Arg Ser Ser Phe Arg Glu Leu Arg Ala Pro Val Ser
305                 310                 315                 320

ggt acc gtc tcg cag ctg cag gtc cac acc gaa ggc ggc gtg gtg gaa     1008
Gly Thr Val Ser Gln Leu Gln Val His Thr Glu Gly Gly Val Val Glu
                325                 330                 335

ggg gcc aag ccg ctc ctc agc ctg gtt ccc gac aat gcc cgg ctc gag     1056
Gly Ala Lys Pro Leu Leu Ser Leu Val Pro Asp Asn Ala Arg Leu Glu
            340                 345                 350

gcc gag gtg atg gtc gac aac agc gac atc ggc ttc gtc cac atc ggc     1104
Ala Glu Val Met Val Asp Asn Ser Asp Ile Gly Phe Val His Ile Gly
        355                 360                 365

atg ccg gta aag gtg aag ctg cag gcc ttt ccc tat acc cgc tac ggc     1152
Met Pro Val Lys Val Lys Leu Gln Ala Phe Pro Tyr Thr Arg Tyr Gly
    370                 375                 380

atg att ccc ggc acg gtg gcg ggc atc agc ccc gag gcg gtg cag atg     1200
Met Ile Pro Gly Thr Val Ala Gly Ile Ser Pro Glu Ala Val Gln Met
385                 390                 395                 400

aag gag aac cag ccg ccg gtc tac aag gcg cgg atc gcg ctg gcg cgc     1248
Lys Glu Asn Gln Pro Pro Val Tyr Lys Ala Arg Ile Ala Leu Ala Arg
                405                 410                 415

ggg tat gtg ctg gcc cat ggc gca cag gtg ccg ctg cgg ccg ggg atg     1296
Gly Tyr Val Leu Ala His Gly Ala Gln Val Pro Leu Arg Pro Gly Met
            420                 425                 430

ctc gcg agc gcg gac atc gtc acc ggc aag cga acc ctg ttc agc tat     1344
Leu Ala Ser Ala Asp Ile Val Thr Gly Lys Arg Thr Leu Phe Ser Tyr
        435                 440                 445

ctg gtg ggg ccc gtg ctc gag acg ggg agt gac gcg ctg cac gag cgg     1392
Leu Val Gly Pro Val Leu Glu Thr Gly Ser Asp Ala Leu His Glu Arg
    450                 455                 460
```

```
tga                                                                1395


<210> SEQ ID NO 31
<211> LENGTH: 464
<212> TYPE: PRT
<213> ORGANISM: Sphingomonas sp. ATCC53159

<400> SEQUENCE: 31

Met Asn Ala Val Val Pro Met Arg Arg Gly Gly Pro Leu Ala Arg Met
1               5                   10                  15

Arg Asp Thr Val Leu Pro Ala Arg Val Asp Ala Tyr Asp Thr Ala Phe
            20                  25                  30

Leu Pro Ala Ala Leu Glu Ile Ile Glu Arg Pro Val Ser Pro Thr Ala
        35                  40                  45

Arg Leu Thr Ala Lys Val Met Leu Ala Gly Leu Ala Ile Thr Ala Ala
    50                  55                  60

Trp Leu Ala Ile Gly Lys Val Glu Val Val Ala Pro Thr Gln Gly Arg
65                  70                  75                  80

Ile Ala Pro Ile Gly Glu Thr Lys Ile Val Gln Ser Pro Glu Ser Gly
                85                  90                  95

Ile Val Arg Arg Ile Leu Val Gly Glu Gly Gln Lys Val Ala Lys Gly
            100                 105                 110

Gln Val Leu Ile Thr Leu Asp Pro Thr Val Ser Ser Ala Glu Ala Ala
        115                 120                 125

Gln Ala Lys Val Ala Leu Leu Ser Ala Gln Leu Asp Ala Ala Arg Asn
    130                 135                 140

Gln Ala Ile Ile Asp Ala Leu Asp Gly Arg Gly Phe Arg Phe Val Ala
145                 150                 155                 160

Pro Ala Ala Ala Ser Pro Gly Glu Val Ala Thr His Arg Gly Leu Ala
                165                 170                 175

Arg Ala Arg Leu Gly Gln Ile Glu Ala Ala Leu Ala Gly Gly Arg Ser
            180                 185                 190

Asp Arg Gly Ala Ala Val Ser Ala Ala Ala Glu Ala Gln Ala Gln Val
        195                 200                 205

Arg Lys Leu Glu Gln Ser Leu Pro Leu Leu Glu Gln Gln Ile Ala Ala
    210                 215                 220

Asn Glu Thr Met Ala Ala Lys Gly Tyr Val Ser Lys Leu Arg Val Val
225                 230                 235                 240

Glu Met Arg Arg Gln Leu Ile Ala Glu Arg Gln Asp Leu Thr Ala Ala
                245                 250                 255

Arg Ala Thr Leu Ala Lys Leu Gly Gln Gln Ser Leu Ser Val Ser Ser
            260                 265                 270

Leu Ser Ala Lys Thr Arg Glu Glu Ala Arg Ala Gln Val Leu Gln Asp
        275                 280                 285

Leu Val Lys Ala Gln Asp Glu Val Arg Ala Arg Gly Glu Asp Val Ala
    290                 295                 300

Lys Ala Asn Leu Arg Ser Ser Phe Arg Glu Leu Arg Ala Pro Val Ser
305                 310                 315                 320

Gly Thr Val Ser Gln Leu Gln Val His Thr Glu Gly Gly Val Val Glu
                325                 330                 335

Gly Ala Lys Pro Leu Leu Ser Leu Val Pro Asp Asn Ala Arg Leu Glu
            340                 345                 350

Ala Glu Val Met Val Asp Asn Ser Asp Ile Gly Phe Val His Ile Gly
        355                 360                 365
```

```
Met Pro Val Lys Val Lys Leu Gln Ala Phe Pro Tyr Thr Arg Tyr Gly
    370                 375                 380

Met Ile Pro Gly Thr Val Ala Gly Ile Ser Pro Glu Ala Val Gln Met
385                 390                 395                 400

Lys Glu Asn Gln Pro Pro Val Tyr Lys Ala Arg Ile Ala Leu Ala Arg
                405                 410                 415

Gly Tyr Val Leu Ala His Gly Ala Gln Val Pro Leu Arg Pro Gly Met
            420                 425                 430

Leu Ala Ser Ala Asp Ile Val Thr Gly Lys Arg Thr Leu Phe Ser Tyr
        435                 440                 445

Leu Val Gly Pro Val Leu Glu Thr Gly Ser Asp Ala Leu His Glu Arg
    450                 455                 460


<210> SEQ ID NO 32
<211> LENGTH: 2187
<212> TYPE: DNA
<213> ORGANISM: Sphingomonas sp. ATCC53159
<220> FEATURE:
<221> NAME/KEY: CDS
<222> LOCATION: (1)..(2187)

<400> SEQUENCE: 32

atg aca cgc gac gaa atg cag gcc acc ctg cag agc gcg ctc gcg gcc      48
Met Thr Arg Asp Glu Met Gln Ala Thr Leu Gln Ser Ala Leu Ala Ala
1               5                   10                  15

cat ggg gcg gcg gag cgc gag gcg gag ctg cgc gaa tcc gga ctg gtg      96
His Gly Ala Ala Glu Arg Glu Ala Glu Leu Arg Glu Ser Gly Leu Val
            20                  25                  30

gcg ttg tcg ctg ctg ctc ggc gcg cac aac atc gcc atc acg ccc gaa     144
Ala Leu Ser Leu Leu Leu Gly Ala His Asn Ile Ala Ile Thr Pro Glu
        35                  40                  45

cag ctg cgc cac gcg ctg ggc cat gcc gag gcg gca agc gcc gac gac     192
Gln Leu Arg His Ala Leu Gly His Ala Glu Ala Ala Ser Ala Asp Asp
    50                  55                  60

ctg atc ctc ctg gcc aag cgc cag cag ggc gtg cgc gcc aag gcc gtc     240
Leu Ile Leu Leu Ala Lys Arg Gln Gln Gly Val Arg Ala Lys Ala Val
65                  70                  75                  80

gag gtg ccg cgc ggc gga ctc gcc cgc cag ccg ctg ccc gcg atc gcc     288
Glu Val Pro Arg Gly Gly Leu Ala Arg Gln Pro Leu Pro Ala Ile Ala
                85                  90                  95

gac ggg ccc gaa ggc tgg ttc gtg atc ggc ggc ctg acc gaa cat ggc     336
Asp Gly Pro Glu Gly Trp Phe Val Ile Gly Gly Leu Thr Glu His Gly
            100                 105                 110

gtg atc atc cag cgc ccg ggc cat gcc ccg gaa cag gtc gac cgg gac     384
Val Ile Ile Gln Arg Pro Gly His Ala Pro Glu Gln Val Asp Arg Asp
        115                 120                 125

gcg ctg gac gcg atc tgg tcc ggc gcg ctg gtg ctg ctc acc acc cgc     432
Ala Leu Asp Ala Ile Trp Ser Gly Ala Leu Val Leu Leu Thr Thr Arg
    130                 135                 140

gcg gtg gcg gga cgg ccg ctg cgg ttc ggc ctc tcc tgg ttc acc gcg     480
Ala Val Ala Gly Arg Pro Leu Arg Phe Gly Leu Ser Trp Phe Thr Ala
145                 150                 155                 160

cag ttc cgg cgc tat cgc acg ctg ttc ctc gag gtg ctc ggc atc acc     528
Gln Phe Arg Arg Tyr Arg Thr Leu Phe Leu Glu Val Leu Gly Ile Thr
                165                 170                 175

ctc gcg ctc aac ctg ctc ggc ctc gcc gcg ccg ctg ttg ttc cag agc     576
Leu Ala Leu Asn Leu Leu Gly Leu Ala Ala Pro Leu Leu Phe Gln Ser
            180                 185                 190

gtg atc gac aag gtg ctg atc cac aac agc atg agc acg ctg agc gtg     624
```

```
Val Ile Asp Lys Val Leu Ile His Asn Ser Met Ser Thr Leu Ser Val
        195                 200                 205

ctc gcc ttc gcc ttc ctg gcg gtt tcg gtg tgg gaa gtg gcg ctc ggc      672
Leu Ala Phe Ala Phe Leu Ala Val Ser Val Trp Glu Val Ala Leu Gly
    210                 215                 220

tgg atc cgc acc cgc ctg ttc acc gag acg acg cag aag atc gac gtc      720
Trp Ile Arg Thr Arg Leu Phe Thr Glu Thr Thr Gln Lys Ile Asp Val
225                 230                 235                 240

gag ctg ggt gcc cgg ctg ttc cac cac ctg ctg gcg ctg ccg ctc gcc      768
Glu Leu Gly Ala Arg Leu Phe His His Leu Leu Ala Leu Pro Leu Ala
                245                 250                 255

tat ttc gag aag cgc cgc gtg ggc gac acc gtc acc cgc gtc cgc cag      816
Tyr Phe Glu Lys Arg Arg Val Gly Asp Thr Val Thr Arg Val Arg Gln
            260                 265                 270

ctc gag acg atc cgc gaa ttc ctt acc agc gcc tcg ctg acg gtg atg      864
Leu Glu Thr Ile Arg Glu Phe Leu Thr Ser Ala Ser Leu Thr Val Met
        275                 280                 285

gtg gac ccg ctg ttc acc ttc gtg ttc ctc gcc gcg atg ctg ttc tac      912
Val Asp Pro Leu Phe Thr Phe Val Phe Leu Ala Ala Met Leu Phe Tyr
    290                 295                 300

tcg ccg atg ctc tcg ggc atc gtg ctc gtg tcg ctg atc gcc tat gcg      960
Ser Pro Met Leu Ser Gly Ile Val Leu Val Ser Leu Ile Ala Tyr Ala
305                 310                 315                 320

atc gta tcg ttc agc gtc gcc ggg ccg ctc cgc gcg cgg gtg gag gac     1008
Ile Val Ser Phe Ser Val Ala Gly Pro Leu Arg Ala Arg Val Glu Asp
                325                 330                 335

aag ttc gag aag agc tcc gcc agc aac gcg ctg ctc gtc gag agc gtc     1056
Lys Phe Glu Lys Ser Ser Ala Ser Asn Ala Leu Leu Val Glu Ser Val
            340                 345                 350

tcg ggc atc cac acg atc aag gcg acc gcg gtc gag ccg cac tgg cag     1104
Ser Gly Ile His Thr Ile Lys Ala Thr Ala Val Glu Pro His Trp Gln
        355                 360                 365

aat cgc tgg gag cgc cag ctc gcc gcc cat acc gcc gcg tcg cag cgg     1152
Asn Arg Trp Glu Arg Gln Leu Ala Ala His Thr Ala Ala Ser Gln Arg
    370                 375                 380

ctg atc aat acc gcc aac acc ggc agc cag gcg atc gag ctg atc tcg     1200
Leu Ile Asn Thr Ala Asn Thr Gly Ser Gln Ala Ile Glu Leu Ile Ser
385                 390                 395                 400

aag ctg agc ttc gcg gcg atc ctg ttc ttc ggc gcc aag gcg gtg atc     1248
Lys Leu Ser Phe Ala Ala Ile Leu Phe Phe Gly Ala Lys Ala Val Ile
                405                 410                 415

ggc ggc gcg atg agc gta ggc gcg ctg gtg gcg ttc aac atg ttc gcc     1296
Gly Gly Ala Met Ser Val Gly Ala Leu Val Ala Phe Asn Met Phe Ala
            420                 425                 430

cag cgc gtg tcc ggg ccg gtg atc cgc atg gcg cag ctg tgg cag gat     1344
Gln Arg Val Ser Gly Pro Val Ile Arg Met Ala Gln Leu Trp Gln Asp
        435                 440                 445

ttc cag cag gtg cgc atc tcg gtc gag cgg ctg ggc gac gtg ctc aac     1392
Phe Gln Gln Val Arg Ile Ser Val Glu Arg Leu Gly Asp Val Leu Asn
    450                 455                 460

cat ccg gtg gaa ccg cgc ccg gcc tcg gcg gcg acg ctg ccg gtg ctg     1440
His Pro Val Glu Pro Arg Pro Ala Ser Ala Ala Thr Leu Pro Val Leu
465                 470                 475                 480

cgc ggt gcg att cgc ttc gag aat gtc agc ttc cgc tat gcc gag gac     1488
Arg Gly Ala Ile Arg Phe Glu Asn Val Ser Phe Arg Tyr Ala Glu Asp
                485                 490                 495

cag ccg ccg gtg ctg agc gac atc acg ctc gac att ccg gcg ggc acc     1536
Gln Pro Pro Val Leu Ser Asp Ile Thr Leu Asp Ile Pro Ala Gly Thr
            500                 505                 510
```

```
tcg ctc ggc atc gtc ggt tcg tcg ggc tcg ggc aag tcg acg ctg gcc     1584
Ser Leu Gly Ile Val Gly Ser Ser Gly Ser Gly Lys Ser Thr Leu Ala
        515                 520                 525

aag ctg ctc cag cgg ctc aac ctg ccg aat ctc ggc cgc gtg ctg gtc     1632
Lys Leu Leu Gln Arg Leu Asn Leu Pro Asn Leu Gly Arg Val Leu Val
    530                 535                 540

gac gag gtc gac gtg gcg cag ctc gat ccc gcc tgg ctg cgt cgc cag     1680
Asp Glu Val Asp Val Ala Gln Leu Asp Pro Ala Trp Leu Arg Arg Gln
545                 550                 555                 560

atc ggc gtc gtg ctg cag gag aat ctg ctg ttc agc cgc tcg atc cgc     1728
Ile Gly Val Val Leu Gln Glu Asn Leu Leu Phe Ser Arg Ser Ile Arg
                565                 570                 575

gag aac atc gcg ctc tcc aac ccc gcc atg ccg ttc gag aat gtc gtc     1776
Glu Asn Ile Ala Leu Ser Asn Pro Ala Met Pro Phe Glu Asn Val Val
            580                 585                 590

gcg gcg gcg acg ctg gcc ggc gcg cat gat ttc atc ctg cgc cag ccg     1824
Ala Ala Ala Thr Leu Ala Gly Ala His Asp Phe Ile Leu Arg Gln Pro
        595                 600                 605

cgc ggc tat gac acc gag atc gtc gag cgc ggc gtc aat ctc tcc ggc     1872
Arg Gly Tyr Asp Thr Glu Ile Val Glu Arg Gly Val Asn Leu Ser Gly
    610                 615                 620

ggc cag cgc cag cgg ctc gcc atc gcc cgc gcg ctc gtc ggc aat ccg     1920
Gly Gln Arg Gln Arg Leu Ala Ile Ala Arg Ala Leu Val Gly Asn Pro
625                 630                 635                 640

cgc atc ctg gtg ttc gac gaa gcg acc tcg gcg ctc gat gcc gag agc     1968
Arg Ile Leu Val Phe Asp Glu Ala Thr Ser Ala Leu Asp Ala Glu Ser
                645                 650                 655

gag gag ctg atc cag aac aac ctg cgc gcc atc tcg gcc ggc cgc acg     2016
Glu Glu Leu Ile Gln Asn Asn Leu Arg Ala Ile Ser Ala Gly Arg Thr
            660                 665                 670

ctc gtg gtg atc gcg cat cgc ctg agc gcg gtg cgc agc tgc gac cgg     2064
Leu Val Val Ile Ala His Arg Leu Ser Ala Val Arg Ser Cys Asp Arg
        675                 680                 685

atc atc acg ctc gaa cag ggc cgc atc gtc gag agc ggc cga cac gac     2112
Ile Ile Thr Leu Glu Gln Gly Arg Ile Val Glu Ser Gly Arg His Asp
    690                 695                 700

gaa ttg ttg cgc ctg ggc ggc cgc tat gcc gac ctg cac cgc cgc cag     2160
Glu Leu Leu Arg Leu Gly Gly Arg Tyr Ala Asp Leu His Arg Arg Gln
705                 710                 715                 720

ggc ggc tat ggg gag att gcc gca tga                                 2187
Gly Gly Tyr Gly Glu Ile Ala Ala
                725


<210> SEQ ID NO 33
<211> LENGTH: 728
<212> TYPE: PRT
<213> ORGANISM: Sphingomonas sp. ATCC53159

<400> SEQUENCE: 33

Met Thr Arg Asp Glu Met Gln Ala Thr Leu Gln Ser Ala Leu Ala Ala
1               5                   10                  15

His Gly Ala Ala Glu Arg Glu Ala Glu Leu Arg Glu Ser Gly Leu Val
            20                  25                  30

Ala Leu Ser Leu Leu Leu Gly Ala His Asn Ile Ala Ile Thr Pro Glu
        35                  40                  45

Gln Leu Arg His Ala Leu Gly His Ala Glu Ala Ala Ser Ala Asp Asp
    50                  55                  60

Leu Ile Leu Leu Ala Lys Arg Gln Gln Gly Val Arg Ala Lys Ala Val
65                  70                  75                  80
```

```
Glu Val Pro Arg Gly Gly Leu Ala Arg Gln Pro Leu Pro Ala Ile Ala
                85                  90                  95

Asp Gly Pro Glu Gly Trp Phe Val Ile Gly Gly Leu Thr Glu His Gly
            100                 105                 110

Val Ile Ile Gln Arg Pro Gly His Ala Pro Glu Gln Val Asp Arg Asp
        115                 120                 125

Ala Leu Asp Ala Ile Trp Ser Gly Ala Leu Val Leu Leu Thr Thr Arg
    130                 135                 140

Ala Val Ala Gly Arg Pro Leu Arg Phe Gly Leu Ser Trp Phe Thr Ala
145                 150                 155                 160

Gln Phe Arg Arg Tyr Arg Thr Leu Phe Leu Glu Val Leu Gly Ile Thr
                165                 170                 175

Leu Ala Leu Asn Leu Leu Gly Leu Ala Ala Pro Leu Leu Phe Gln Ser
            180                 185                 190

Val Ile Asp Lys Val Leu Ile His Asn Ser Met Ser Thr Leu Ser Val
        195                 200                 205

Leu Ala Phe Ala Phe Leu Ala Val Ser Val Trp Glu Val Ala Leu Gly
    210                 215                 220

Trp Ile Arg Thr Arg Leu Phe Thr Glu Thr Thr Gln Lys Ile Asp Val
225                 230                 235                 240

Glu Leu Gly Ala Arg Leu Phe His His Leu Leu Ala Leu Pro Leu Ala
                245                 250                 255

Tyr Phe Glu Lys Arg Arg Val Gly Asp Thr Val Thr Arg Val Arg Gln
            260                 265                 270

Leu Glu Thr Ile Arg Glu Phe Leu Thr Ser Ala Ser Leu Thr Val Met
        275                 280                 285

Val Asp Pro Leu Phe Thr Phe Val Phe Leu Ala Ala Met Leu Phe Tyr
    290                 295                 300

Ser Pro Met Leu Ser Gly Ile Val Leu Val Ser Leu Ile Ala Tyr Ala
305                 310                 315                 320

Ile Val Ser Phe Ser Val Ala Gly Pro Leu Arg Ala Arg Val Glu Asp
                325                 330                 335

Lys Phe Glu Lys Ser Ser Ala Ser Asn Ala Leu Leu Val Glu Ser Val
            340                 345                 350

Ser Gly Ile His Thr Ile Lys Ala Thr Ala Val Glu Pro His Trp Gln
        355                 360                 365

Asn Arg Trp Glu Arg Gln Leu Ala Ala His Thr Ala Ala Ser Gln Arg
    370                 375                 380

Leu Ile Asn Thr Ala Asn Thr Gly Ser Gln Ala Ile Glu Leu Ile Ser
385                 390                 395                 400

Lys Leu Ser Phe Ala Ala Ile Leu Phe Phe Gly Ala Lys Ala Val Ile
                405                 410                 415

Gly Gly Ala Met Ser Val Gly Ala Leu Val Ala Phe Asn Met Phe Ala
            420                 425                 430

Gln Arg Val Ser Gly Pro Val Ile Arg Met Ala Gln Leu Trp Gln Asp
        435                 440                 445

Phe Gln Gln Val Arg Ile Ser Val Glu Arg Leu Gly Asp Val Leu Asn
    450                 455                 460

His Pro Val Glu Pro Arg Pro Ala Ser Ala Ala Thr Leu Pro Val Leu
465                 470                 475                 480

Arg Gly Ala Ile Arg Phe Glu Asn Val Ser Phe Arg Tyr Ala Glu Asp
                485                 490                 495

Gln Pro Pro Val Leu Ser Asp Ile Thr Leu Asp Ile Pro Ala Gly Thr
```

```
            500                 505                 510

Ser Leu Gly Ile Val Gly Ser Ser Gly Ser Gly Lys Ser Thr Leu Ala
        515                 520                 525

Lys Leu Leu Gln Arg Leu Asn Leu Pro Asn Leu Gly Arg Val Leu Val
    530                 535                 540

Asp Glu Val Asp Val Ala Gln Leu Asp Pro Ala Trp Leu Arg Arg Gln
545                 550                 555                 560

Ile Gly Val Val Leu Gln Glu Asn Leu Leu Phe Ser Arg Ser Ile Arg
                565                 570                 575

Glu Asn Ile Ala Leu Ser Asn Pro Ala Met Pro Phe Glu Asn Val Val
            580                 585                 590

Ala Ala Ala Thr Leu Ala Gly Ala His Asp Phe Ile Leu Arg Gln Pro
        595                 600                 605

Arg Gly Tyr Asp Thr Glu Ile Val Glu Arg Gly Val Asn Leu Ser Gly
    610                 615                 620

Gly Gln Arg Gln Arg Leu Ala Ile Ala Arg Ala Leu Val Gly Asn Pro
625                 630                 635                 640

Arg Ile Leu Val Phe Asp Glu Ala Thr Ser Ala Leu Asp Ala Glu Ser
                645                 650                 655

Glu Glu Leu Ile Gln Asn Asn Leu Arg Ala Ile Ser Ala Gly Arg Thr
            660                 665                 670

Leu Val Val Ile Ala His Arg Leu Ser Ala Val Arg Ser Cys Asp Arg
        675                 680                 685

Ile Ile Thr Leu Glu Gln Gly Arg Ile Val Glu Ser Gly Arg His Asp
    690                 695                 700

Glu Leu Leu Arg Leu Gly Gly Arg Tyr Ala Asp Leu His Arg Arg Gln
705                 710                 715                 720

Gly Gly Tyr Gly Glu Ile Ala Ala
                725


<210> SEQ ID NO 34
<211> LENGTH: 1413
<212> TYPE: DNA
<213> ORGANISM: Sphingomonas sp. ATCC53159
<220> FEATURE:
<221> NAME/KEY: CDS
<222> LOCATION: (1)..(1413)

<400> SEQUENCE: 34

atg aac gct ttc gaa gca cag cgc gcc ttt gag gag caa ctt cgg gcg       48
Met Asn Ala Phe Glu Ala Gln Arg Ala Phe Glu Glu Gln Leu Arg Ala
1               5                   10                  15

cat tcc cgg gtt acg cca tct gcc gct ccc gtg tgg cgt cgc tcg acg       96
His Ser Arg Val Thr Pro Ser Ala Ala Pro Val Trp Arg Arg Ser Thr
            20                  25                  30

ctg cgg atg gtc ctc tat acc gag ttg ctg ctg ctg gac agt ctc tcg      144
Leu Arg Met Val Leu Tyr Thr Glu Leu Leu Leu Leu Asp Ser Leu Ser
        35                  40                  45

atc ctg gcc gga ttc cac gtc gcg gcg ggc acg cgc gac ggc aac tgg      192
Ile Leu Ala Gly Phe His Val Ala Ala Gly Thr Arg Asp Gly Asn Trp
    50                  55                  60

ctg tcg ctg gcg ggc atc aac gtc ggc gtc ttc ctg ctg ccg atc gct      240
Leu Ser Leu Ala Gly Ile Asn Val Gly Val Phe Leu Leu Pro Ile Ala
65                  70                  75                  80

ctc ggc acc gcg ctc gca agc ggc acc tac tcg ctg aac tgc ctg cgc      288
Leu Gly Thr Ala Leu Ala Ser Gly Thr Tyr Ser Leu Asn Cys Leu Arg
                85                  90                  95
```

```
tac ccg gtc agc ggc gtg aag agc atc ttc tcg gca ttc ttc ttc tcg      336
Tyr Pro Val Ser Gly Val Lys Ser Ile Phe Ser Ala Phe Phe Phe Ser
            100                 105                 110

atc ttc gtc gtc ctg ctc ggc agc tac ctg ctg acg gcc gag ctg ccg      384
Ile Phe Val Val Leu Leu Gly Ser Tyr Leu Leu Thr Ala Glu Leu Pro
        115                 120                 125

ctg tcc cgc gtg cag ctg gcg gag ggc gcg atc ctc tcg ctg gtc ctc      432
Leu Ser Arg Val Gln Leu Ala Glu Gly Ala Ile Leu Ser Leu Val Leu
    130                 135                 140

ctg atg gtg ggc cgc ctg atg ttc cgc cgc cac gtc cgc gcg gtt acc      480
Leu Met Val Gly Arg Leu Met Phe Arg Arg His Val Arg Ala Val Thr
145                 150                 155                 160

ggc ggc agg ctg ctc gac gaa ctg gtc atc atc gac ggc gtc tcg ctc      528
Gly Gly Arg Leu Leu Asp Glu Leu Val Ile Ile Asp Gly Val Ser Leu
                165                 170                 175

gac gtc gcg ggc aat gcg gtc gcg ctc gac gcg cgg atc atc aat ctc      576
Asp Val Ala Gly Asn Ala Val Ala Leu Asp Ala Arg Ile Ile Asn Leu
            180                 185                 190

tcg ccg aac ccg cgc gat ccg caa atg ctg cat cgc ctg ggc acc acc      624
Ser Pro Asn Pro Arg Asp Pro Gln Met Leu His Arg Leu Gly Thr Thr
        195                 200                 205

gtg atc ggg ttc gac cgg gtg atc gtc gcc tgc acc aag gag cat cgc      672
Val Ile Gly Phe Asp Arg Val Ile Val Ala Cys Thr Lys Glu His Arg
    210                 215                 220

gcg gtc tgg gcg ctg ctg ctc aag ggc atg aac atc aag ggc gag atc      720
Ala Val Trp Ala Leu Leu Leu Lys Gly Met Asn Ile Lys Gly Glu Ile
225                 230                 235                 240

ctc gtc ccc cag ttc aat gcg ctg ggc gcg atc ggc gtg gac gcc ttt      768
Leu Val Pro Gln Phe Asn Ala Leu Gly Ala Ile Gly Val Asp Ala Phe
                245                 250                 255

gac ggg aag gat acg ctg gtc gtc tcg cag ggc ccg ctc aac atg ccc      816
Asp Gly Lys Asp Thr Leu Val Val Ser Gln Gly Pro Leu Asn Met Pro
            260                 265                 270

aac cgc gcg aag aag cgc gcg ctc gat ctc gcg atc acc gta ccg gcc      864
Asn Arg Ala Lys Lys Arg Ala Leu Asp Leu Ala Ile Thr Val Pro Ala
        275                 280                 285

gtg ctc gcg ctg gcg ccg ctg atg atc ctg gtg gcg atc ctg atc aag      912
Val Leu Ala Leu Ala Pro Leu Met Ile Leu Val Ala Ile Leu Ile Lys
    290                 295                 300

ctg gag agc ccg ggc ccg gtg ttg ttc gcg cag gat cgc gtc ggc cgc      960
Leu Glu Ser Pro Gly Pro Val Leu Phe Ala Gln Asp Arg Val Gly Arg
305                 310                 315                 320

ggc aac cgg ctg ttc aag atc atg aag ttc cgc tcg atg cgc gta acg     1008
Gly Asn Arg Leu Phe Lys Ile Met Lys Phe Arg Ser Met Arg Val Thr
                325                 330                 335

ctg tgc gac gcg aac ggc aac gtc tcg gcc agc cgc gac gac gat cgc     1056
Leu Cys Asp Ala Asn Gly Asn Val Ser Ala Ser Arg Asp Asp Asp Arg
            340                 345                 350

atc acc aag gtc ggc cgc ttc atc cgc aag acc agc atc gac gaa ctg     1104
Ile Thr Lys Val Gly Arg Phe Ile Arg Lys Thr Ser Ile Asp Glu Leu
        355                 360                 365

ccg cag ctg ctg aac gtg ctg cgc ggc gac atg agc gtc gtc ggc ccg     1152
Pro Gln Leu Leu Asn Val Leu Arg Gly Asp Met Ser Val Val Gly Pro
    370                 375                 380

cgg ccg cat gcg ctg ggc tcg cgc gcc gcc gat cac ctg ttc tgg gaa     1200
Arg Pro His Ala Leu Gly Ser Arg Ala Ala Asp His Leu Phe Trp Glu
385                 390                 395                 400

atc gac gag cgc tac tgg cac cgc cac acg ctc aag ccg ggc atg acc     1248
Ile Asp Glu Arg Tyr Trp His Arg His Thr Leu Lys Pro Gly Met Thr
                405                 410                 415
```

```
ggt ctg gcc cag gtg cgc ggt ttc cgc ggg gcg acc gat cgc cgc gtc     1296
Gly Leu Ala Gln Val Arg Gly Phe Arg Gly Ala Thr Asp Arg Arg Val
            420                 425                 430

gat ctg acc aac cgg ctc cag gca gac atg gaa tat atc gac gga tgg     1344
Asp Leu Thr Asn Arg Leu Gln Ala Asp Met Glu Tyr Ile Asp Gly Trp
        435                 440                 445

gat atc tgg cgc gat atc acg atc ctg ttc aag acg ctg cgg gtg atc     1392
Asp Ile Trp Arg Asp Ile Thr Ile Leu Phe Lys Thr Leu Arg Val Ile
    450                 455                 460

gtg cat tcg aac gca ttc tga                                         1413
Val His Ser Asn Ala Phe
465                 470


<210> SEQ ID NO 35
<211> LENGTH: 470
<212> TYPE: PRT
<213> ORGANISM: Sphingomonas sp. ATCC53159

<400> SEQUENCE: 35

Met Asn Ala Phe Glu Ala Gln Arg Ala Phe Glu Glu Gln Leu Arg Ala
1               5                   10                  15

His Ser Arg Val Thr Pro Ser Ala Ala Pro Val Trp Arg Arg Ser Thr
            20                  25                  30

Leu Arg Met Val Leu Tyr Thr Glu Leu Leu Leu Leu Asp Ser Leu Ser
        35                  40                  45

Ile Leu Ala Gly Phe His Val Ala Ala Gly Thr Arg Asp Gly Asn Trp
    50                  55                  60

Leu Ser Leu Ala Gly Ile Asn Val Gly Val Phe Leu Leu Pro Ile Ala
65                  70                  75                  80

Leu Gly Thr Ala Leu Ala Ser Gly Thr Tyr Ser Leu Asn Cys Leu Arg
                85                  90                  95

Tyr Pro Val Ser Gly Val Lys Ser Ile Phe Ser Ala Phe Phe Phe Ser
            100                 105                 110

Ile Phe Val Val Leu Leu Gly Ser Tyr Leu Leu Thr Ala Glu Leu Pro
        115                 120                 125

Leu Ser Arg Val Gln Leu Ala Glu Gly Ala Ile Leu Ser Leu Val Leu
    130                 135                 140

Leu Met Val Gly Arg Leu Met Phe Arg Arg His Val Arg Ala Val Thr
145                 150                 155                 160

Gly Gly Arg Leu Leu Asp Glu Leu Val Ile Ile Asp Gly Val Ser Leu
                165                 170                 175

Asp Val Ala Gly Asn Ala Val Ala Leu Asp Ala Arg Ile Ile Asn Leu
            180                 185                 190

Ser Pro Asn Pro Arg Asp Pro Gln Met Leu His Arg Leu Gly Thr Thr
        195                 200                 205

Val Ile Gly Phe Asp Arg Val Ile Val Ala Cys Thr Lys Glu His Arg
    210                 215                 220

Ala Val Trp Ala Leu Leu Leu Lys Gly Met Asn Ile Lys Gly Glu Ile
225                 230                 235                 240

Leu Val Pro Gln Phe Asn Ala Leu Gly Ala Ile Gly Val Asp Ala Phe
                245                 250                 255

Asp Gly Lys Asp Thr Leu Val Val Ser Gln Gly Pro Leu Asn Met Pro
            260                 265                 270

Asn Arg Ala Lys Lys Arg Ala Leu Asp Leu Ala Ile Thr Val Pro Ala
        275                 280                 285
```

```
Val Leu Ala Leu Ala Pro Leu Met Ile Leu Val Ala Ile Leu Ile Lys
    290                 295                 300

Leu Glu Ser Pro Gly Pro Val Leu Phe Ala Gln Asp Arg Val Gly Arg
305                 310                 315                 320

Gly Asn Arg Leu Phe Lys Ile Met Lys Phe Arg Ser Met Arg Val Thr
                325                 330                 335

Leu Cys Asp Ala Asn Gly Asn Val Ser Ala Ser Arg Asp Asp Asp Arg
            340                 345                 350

Ile Thr Lys Val Gly Arg Phe Ile Arg Lys Thr Ser Ile Asp Glu Leu
        355                 360                 365

Pro Gln Leu Leu Asn Val Leu Arg Gly Asp Met Ser Val Val Gly Pro
    370                 375                 380

Arg Pro His Ala Leu Gly Ser Arg Ala Ala Asp His Leu Phe Trp Glu
385                 390                 395                 400

Ile Asp Glu Arg Tyr Trp His Arg His Thr Leu Lys Pro Gly Met Thr
                405                 410                 415

Gly Leu Ala Gln Val Arg Gly Phe Arg Gly Ala Thr Asp Arg Arg Val
            420                 425                 430

Asp Leu Thr Asn Arg Leu Gln Ala Asp Met Glu Tyr Ile Asp Gly Trp
        435                 440                 445

Asp Ile Trp Arg Asp Ile Thr Ile Leu Phe Lys Thr Leu Arg Val Ile
    450                 455                 460

Val His Ser Asn Ala Phe
465                 470


<210> SEQ ID NO 36
<211> LENGTH: 879
<212> TYPE: DNA
<213> ORGANISM: Sphingomonas sp. ATCC53159
<220> FEATURE:
<221> NAME/KEY: CDS
<222> LOCATION: (1)..(879)

<400> SEQUENCE: 36

atg aag ggc atc atc ctt gcg ggg ggc agc ggg acg cgc ctg tac ccc       48
Met Lys Gly Ile Ile Leu Ala Gly Gly Ser Gly Thr Arg Leu Tyr Pro
1               5                   10                  15

gca acg cta tcg atc tcg aag cag ctg ctt ccc gtc tat gac aag ccg       96
Ala Thr Leu Ser Ile Ser Lys Gln Leu Leu Pro Val Tyr Asp Lys Pro
            20                  25                  30

atg atc ttc tat ccg ctg tcg gtg ctg atg ctc acc ggc atc cgg gac      144
Met Ile Phe Tyr Pro Leu Ser Val Leu Met Leu Thr Gly Ile Arg Asp
        35                  40                  45

atc ctg att atc tcc acc ccg cgc gac ctg ccg atg ttc cag gcg ctg      192
Ile Leu Ile Ile Ser Thr Pro Arg Asp Leu Pro Met Phe Gln Ala Leu
    50                  55                  60

ctg ggc gac ggc tcg gcc ttc ggc atc aac ctc agc tat gcc gag cag      240
Leu Gly Asp Gly Ser Ala Phe Gly Ile Asn Leu Ser Tyr Ala Glu Gln
65                  70                  75                  80

ccc tcc ccc aac ggg ctg gcc gaa gcg ttc atc atc ggc gcg gat ttc      288
Pro Ser Pro Asn Gly Leu Ala Glu Ala Phe Ile Ile Gly Ala Asp Phe
                85                  90                  95

gtc ggc aac gat ccc agc gcg ctg atc ctg ggc gac aac atc tat cac      336
Val Gly Asn Asp Pro Ser Ala Leu Ile Leu Gly Asp Asn Ile Tyr His
            100                 105                 110

ggc gaa aag atg ggc gag cgc tgc cag gca gcc gca gcg cag gca gcg      384
Gly Glu Lys Met Gly Glu Arg Cys Gln Ala Ala Ala Ala Gln Ala Ala
        115                 120                 125
```

```
cag ggc ggt gca aac gtc ttc gcc tat cat gtc gac gac ccc gag cgc      432
Gln Gly Gly Ala Asn Val Phe Ala Tyr His Val Asp Asp Pro Glu Arg
    130                 135                 140

tac ggc gtg gtc gcg ttc gac ccg gag acg ggc gtc gcc acc agc gtc      480
Tyr Gly Val Val Ala Phe Asp Pro Glu Thr Gly Val Ala Thr Ser Val
145                 150                 155                 160

gag gaa aag ccg gcc gag ccc aag tcc aac tgg gcg atc acc ggc ctg      528
Glu Glu Lys Pro Ala Glu Pro Lys Ser Asn Trp Ala Ile Thr Gly Leu
                165                 170                 175

tat ttc tac gac aag gac gtg gtc gac atc gcc aag tcg atc cag ccc      576
Tyr Phe Tyr Asp Lys Asp Val Val Asp Ile Ala Lys Ser Ile Gln Pro
            180                 185                 190

tcg gcg cgc ggc gaa ctc gag atc acc gac gtc aac cgc gtt tac atg      624
Ser Ala Arg Gly Glu Leu Glu Ile Thr Asp Val Asn Arg Val Tyr Met
        195                 200                 205

gag cgc ggc gac ctg cac atc acg cgc ctc ggc cgc ggc tat gcc tgg      672
Glu Arg Gly Asp Leu His Ile Thr Arg Leu Gly Arg Gly Tyr Ala Trp
    210                 215                 220

ctc gac acc ggc acg cat gac agc ctg cac gaa gcc ggc tcg ttc gtt      720
Leu Asp Thr Gly Thr His Asp Ser Leu His Glu Ala Gly Ser Phe Val
225                 230                 235                 240

cgc acg ctc gag cat cgg acg ggc gtg aag atc gcc tgc ccg gag gaa      768
Arg Thr Leu Glu His Arg Thr Gly Val Lys Ile Ala Cys Pro Glu Glu
                245                 250                 255

atc gcc ttc gaa agc ggc tgg ctc ggc gcc gaa gac ctg ctc aag cgc      816
Ile Ala Phe Glu Ser Gly Trp Leu Gly Ala Glu Asp Leu Leu Lys Arg
            260                 265                 270

gcc gcc ggc ctc ggc aag acc ggc tat gcc gcc tat ctc cgc aag gtt      864
Ala Ala Gly Leu Gly Lys Thr Gly Tyr Ala Ala Tyr Leu Arg Lys Val
        275                 280                 285

gcg acc gca gca tga                                                  879
Ala Thr Ala Ala
    290


<210> SEQ ID NO 37
<211> LENGTH: 292
<212> TYPE: PRT
<213> ORGANISM: Sphingomonas sp. ATCC53159

<400> SEQUENCE: 37

Met Lys Gly Ile Ile Leu Ala Gly Gly Ser Gly Thr Arg Leu Tyr Pro
1               5                   10                  15

Ala Thr Leu Ser Ile Ser Lys Gln Leu Leu Pro Val Tyr Asp Lys Pro
            20                  25                  30

Met Ile Phe Tyr Pro Leu Ser Val Leu Met Leu Thr Gly Ile Arg Asp
        35                  40                  45

Ile Leu Ile Ile Ser Thr Pro Arg Asp Leu Pro Met Phe Gln Ala Leu
    50                  55                  60

Leu Gly Asp Gly Ser Ala Phe Gly Ile Asn Leu Ser Tyr Ala Glu Gln
65                  70                  75                  80

Pro Ser Pro Asn Gly Leu Ala Glu Ala Phe Ile Ile Gly Ala Asp Phe
                85                  90                  95

Val Gly Asn Asp Pro Ser Ala Leu Ile Leu Gly Asp Asn Ile Tyr His
            100                 105                 110

Gly Glu Lys Met Gly Glu Arg Cys Gln Ala Ala Ala Ala Gln Ala Ala
        115                 120                 125

Gln Gly Gly Ala Asn Val Phe Ala Tyr His Val Asp Asp Pro Glu Arg
    130                 135                 140
```

```
Tyr Gly Val Val Ala Phe Asp Pro Glu Thr Gly Val Ala Thr Ser Val
145                 150                 155                 160

Glu Glu Lys Pro Ala Glu Pro Lys Ser Asn Trp Ala Ile Thr Gly Leu
                165                 170                 175

Tyr Phe Tyr Asp Lys Asp Val Val Asp Ile Ala Lys Ser Ile Gln Pro
            180                 185                 190

Ser Ala Arg Gly Glu Leu Glu Ile Thr Asp Val Asn Arg Val Tyr Met
        195                 200                 205

Glu Arg Gly Asp Leu His Ile Thr Arg Leu Gly Arg Gly Tyr Ala Trp
    210                 215                 220

Leu Asp Thr Gly Thr His Asp Ser Leu His Glu Ala Gly Ser Phe Val
225                 230                 235                 240

Arg Thr Leu Glu His Arg Thr Gly Val Lys Ile Ala Cys Pro Glu Glu
                245                 250                 255

Ile Ala Phe Glu Ser Gly Trp Leu Gly Ala Glu Asp Leu Leu Lys Arg
            260                 265                 270

Ala Ala Gly Leu Gly Lys Thr Gly Tyr Ala Ala Tyr Leu Arg Lys Val
        275                 280                 285

Ala Thr Ala Ala
    290


<210> SEQ ID NO 38
<211> LENGTH: 567
<212> TYPE: DNA
<213> ORGANISM: Sphingomonas sp. ATCC53159
<220> FEATURE:
<221> NAME/KEY: CDS
<222> LOCATION: (1)..(567)

<400> SEQUENCE: 38

atg acc cag gtc cat cat cac gaa ctg tcc ggc gtc atc gag ttc acg       48
Met Thr Gln Val His His His Glu Leu Ser Gly Val Ile Glu Phe Thr
1               5                   10                  15

ccg ccc aaa tat ggc gac cac cgc ggc ttc ttc tcc gaa gtg ttc aag       96
Pro Pro Lys Tyr Gly Asp His Arg Gly Phe Phe Ser Glu Val Phe Lys
            20                  25                  30

cag tcg gtg ctc gat gcc gaa ggc gtc gag gca cgc tgg gtg cag gac      144
Gln Ser Val Leu Asp Ala Glu Gly Val Glu Ala Arg Trp Val Gln Asp
        35                  40                  45

aat cag agc ttc tcg gcg gcc ccg ggc acg atc cgc ggc ctg cat ctc      192
Asn Gln Ser Phe Ser Ala Ala Pro Gly Thr Ile Arg Gly Leu His Leu
    50                  55                  60

cag gcg ccg ccc ttc gcc cag gcc aag ctg gtc cgc gtg ttg cgc ggc      240
Gln Ala Pro Pro Phe Ala Gln Ala Lys Leu Val Arg Val Leu Arg Gly
65                  70                  75                  80

gcg atc ttc gac gtc gcg gtc gac atc cgt cgc ggc tcg ccc acc tat      288
Ala Ile Phe Asp Val Ala Val Asp Ile Arg Arg Gly Ser Pro Thr Tyr
                85                  90                  95

ggc aaa tgg gtc ggc gtc gag ctc tcg gcc gag aag tgg aac cag ctg      336
Gly Lys Trp Val Gly Val Glu Leu Ser Ala Glu Lys Trp Asn Gln Leu
            100                 105                 110

ctg gtc ccc gcc ggc tat gcg cac ggc ttc atg acg ctc gtt ccg gat      384
Leu Val Pro Ala Gly Tyr Ala His Gly Phe Met Thr Leu Val Pro Asp
        115                 120                 125

tgc gag atc ctc tac aag gtc agc gcc aaa tat tcg aag gat tcg gag      432
Cys Glu Ile Leu Tyr Lys Val Ser Ala Lys Tyr Ser Lys Asp Ser Glu
    130                 135                 140

atg gcg atc cgt tgg gac gat ccc gat ctc gcc atc gcc tgg ccg gac      480
Met Ala Ile Arg Trp Asp Asp Pro Asp Leu Ala Ile Ala Trp Pro Asp
```

```
145                 150                 155                 160

atc ggc gtc gag ccg gtc ctc tcc gaa aag gac gcg gtc gcc acg ccc      528
Ile Gly Val Glu Pro Val Leu Ser Glu Lys Asp Ala Val Ala Thr Pro
                165                 170                 175

ttc gcc gaa ttc aac acc ccc ttc ttc tat cag ggc tga                  567
Phe Ala Glu Phe Asn Thr Pro Phe Phe Tyr Gln Gly
            180                 185


<210> SEQ ID NO 39
<211> LENGTH: 188
<212> TYPE: PRT
<213> ORGANISM: Sphingomonas sp. ATCC53159

<400> SEQUENCE: 39

Met Thr Gln Val His His His Glu Leu Ser Gly Val Ile Glu Phe Thr
1               5                   10                  15

Pro Pro Lys Tyr Gly Asp His Arg Gly Phe Phe Ser Glu Val Phe Lys
            20                  25                  30

Gln Ser Val Leu Asp Ala Glu Gly Val Glu Ala Arg Trp Val Gln Asp
        35                  40                  45

Asn Gln Ser Phe Ser Ala Ala Pro Gly Thr Ile Arg Gly Leu His Leu
    50                  55                  60

Gln Ala Pro Pro Phe Ala Gln Ala Lys Leu Val Arg Val Leu Arg Gly
65                  70                  75                  80

Ala Ile Phe Asp Val Ala Val Asp Ile Arg Arg Gly Ser Pro Thr Tyr
                85                  90                  95

Gly Lys Trp Val Gly Val Glu Leu Ser Ala Glu Lys Trp Asn Gln Leu
            100                 105                 110

Leu Val Pro Ala Gly Tyr Ala His Gly Phe Met Thr Leu Val Pro Asp
        115                 120                 125

Cys Glu Ile Leu Tyr Lys Val Ser Ala Lys Tyr Ser Lys Asp Ser Glu
    130                 135                 140

Met Ala Ile Arg Trp Asp Asp Pro Asp Leu Ala Ile Ala Trp Pro Asp
145                 150                 155                 160

Ile Gly Val Glu Pro Val Leu Ser Glu Lys Asp Ala Val Ala Thr Pro
                165                 170                 175

Phe Ala Glu Phe Asn Thr Pro Phe Phe Tyr Gln Gly
            180                 185


<210> SEQ ID NO 40
<211> LENGTH: 1062
<212> TYPE: DNA
<213> ORGANISM: Sphingomonas sp. ATCC53159
<220> FEATURE:
<221> NAME/KEY: CDS
<222> LOCATION: (1)..(1062)

<400> SEQUENCE: 40

atg cag cag acc ttc ctc gtc acc ggc ggc gcc ggc ttc atc ggc tcg       48
Met Gln Gln Thr Phe Leu Val Thr Gly Gly Ala Gly Phe Ile Gly Ser
1               5                   10                  15

gcg gtg gtg cgc cac ctc gtc cgc cag ggc gcg cgc gtc atc aat ctc       96
Ala Val Val Arg His Leu Val Arg Gln Gly Ala Arg Val Ile Asn Leu
            20                  25                  30

gac aag ctc acc tat gcc ggc aac ccg gcc tcg ctg act gcg atc gag      144
Asp Lys Leu Thr Tyr Ala Gly Asn Pro Ala Ser Leu Thr Ala Ile Glu
        35                  40                  45

aac gcg ccc aac tat cgc ttc gtc cat gcc gac atc gcc gac acc gcg      192
Asn Ala Pro Asn Tyr Arg Phe Val His Ala Asp Ile Ala Asp Thr Ala
```

```
    50                  55                  60

acg atc cta ccg ctg ctg cgc gag gag cag gtc gat gtg gtg atg cac      240
Thr Ile Leu Pro Leu Leu Arg Glu Glu Gln Val Asp Val Val Met His
65                  70                  75                  80

ctc gcc gcc gag agc cat gtc gat cgc tcg atc gac ggc cct ggc gag      288
Leu Ala Ala Glu Ser His Val Asp Arg Ser Ile Asp Gly Pro Gly Glu
                85                  90                  95

ttc atc gag acc aat gtc gtc ggc acc ttc aag ctg ctc cag tcg gcg      336
Phe Ile Glu Thr Asn Val Val Gly Thr Phe Lys Leu Leu Gln Ser Ala
            100                 105                 110

ctg caa tat tgg cgc gag ctg gag ggc gag aaa cgc gac gcg ttc cgc      384
Leu Gln Tyr Trp Arg Glu Leu Glu Gly Glu Lys Arg Asp Ala Phe Arg
        115                 120                 125

ttc cac cac atc tcc acc gac gaa gtg ttc ggc gac ctg ccg ttc gac      432
Phe His His Ile Ser Thr Asp Glu Val Phe Gly Asp Leu Pro Phe Asp
    130                 135                 140

agc ggc atc ttc acc gaa gag acg ccc tat gat ccc tcc tcg ccc tat      480
Ser Gly Ile Phe Thr Glu Glu Thr Pro Tyr Asp Pro Ser Ser Pro Tyr
145                 150                 155                 160

tcg gcg tcg aag gcg gcg agc gac cat ctg gtg cgc gcc tgg ggc cac      528
Ser Ala Ser Lys Ala Ala Ser Asp His Leu Val Arg Ala Trp Gly His
                165                 170                 175

acc tat ggc ctg ccg gtg gtg ctg tcg aac tgc tcg aac aat tac ggg      576
Thr Tyr Gly Leu Pro Val Val Leu Ser Asn Cys Ser Asn Asn Tyr Gly
            180                 185                 190

ccg ttc cac ttc ccc gag aag ctg atc ccg ttg acc atc ctc aac gcg      624
Pro Phe His Phe Pro Glu Lys Leu Ile Pro Leu Thr Ile Leu Asn Ala
        195                 200                 205

ctc gag ggc aag ccg ctg ccg gtc tac ggc aag ggc gag aat atc cgc      672
Leu Glu Gly Lys Pro Leu Pro Val Tyr Gly Lys Gly Glu Asn Ile Arg
    210                 215                 220

gac tgg ctg tat gtc gac gat cac gcc aag gcg ctg gcg acc atc gcc      720
Asp Trp Leu Tyr Val Asp Asp His Ala Lys Ala Leu Ala Thr Ile Ala
225                 230                 235                 240

acc acc ggc aag gtc ggc cag agc tac aat gtc ggc ggc cgc aac gag      768
Thr Thr Gly Lys Val Gly Gln Ser Tyr Asn Val Gly Gly Arg Asn Glu
                245                 250                 255

cgg acc aac ctg cag gtg gtc gag acg atc tgc gac ctg ctc gac cag      816
Arg Thr Asn Leu Gln Val Val Glu Thr Ile Cys Asp Leu Leu Asp Gln
            260                 265                 270

cgc att ccg ctg gcc gac ggt cgc aag cgc cgc gaa ctg atc acc ttc      864
Arg Ile Pro Leu Ala Asp Gly Arg Lys Arg Arg Glu Leu Ile Thr Phe
        275                 280                 285

gtc acc gat cgc ccc ggc cat gac cgc cgc tac gcg atc gac gcg acc      912
Val Thr Asp Arg Pro Gly His Asp Arg Arg Tyr Ala Ile Asp Ala Thr
    290                 295                 300

aag ctc gag acc gag ctg ggc tgg aag gct gag gag aat ttc gac acc      960
Lys Leu Glu Thr Glu Leu Gly Trp Lys Ala Glu Glu Asn Phe Asp Thr
305                 310                 315                 320

ggc atc gcc gcg acg atc gac tgg tat ctg gcg aac gag tgg tgg tgg     1008
Gly Ile Ala Ala Thr Ile Asp Trp Tyr Leu Ala Asn Glu Trp Trp Trp
                325                 330                 335

ggc ccg atc cgc tcc ggc aaa tat gcc ggc gag cgg ctg ggg cag acc     1056
Gly Pro Ile Arg Ser Gly Lys Tyr Ala Gly Glu Arg Leu Gly Gln Thr
            340                 345                 350

gcc tga                                                             1062
Ala
```

<210> SEQ ID NO 41

```
<211> LENGTH: 353
<212> TYPE: PRT
<213> ORGANISM: Sphingomonas sp. ATCC53159

<400> SEQUENCE: 41

Met Gln Gln Thr Phe Leu Val Thr Gly Gly Ala Gly Phe Ile Gly Ser
1               5                   10                  15

Ala Val Val Arg His Leu Val Arg Gln Gly Ala Arg Val Ile Asn Leu
            20                  25                  30

Asp Lys Leu Thr Tyr Ala Gly Asn Pro Ala Ser Leu Thr Ala Ile Glu
        35                  40                  45

Asn Ala Pro Asn Tyr Arg Phe Val His Ala Asp Ile Ala Asp Thr Ala
    50                  55                  60

Thr Ile Leu Pro Leu Leu Arg Glu Glu Gln Val Asp Val Val Met His
65                  70                  75                  80

Leu Ala Ala Glu Ser His Val Asp Arg Ser Ile Asp Gly Pro Gly Glu
                85                  90                  95

Phe Ile Glu Thr Asn Val Val Gly Thr Phe Lys Leu Leu Gln Ser Ala
            100                 105                 110

Leu Gln Tyr Trp Arg Glu Leu Glu Gly Glu Lys Arg Asp Ala Phe Arg
        115                 120                 125

Phe His His Ile Ser Thr Asp Glu Val Phe Gly Asp Leu Pro Phe Asp
    130                 135                 140

Ser Gly Ile Phe Thr Glu Glu Thr Pro Tyr Asp Pro Ser Ser Pro Tyr
145                 150                 155                 160

Ser Ala Ser Lys Ala Ala Ser Asp His Leu Val Arg Ala Trp Gly His
                165                 170                 175

Thr Tyr Gly Leu Pro Val Val Leu Ser Asn Cys Ser Asn Asn Tyr Gly
            180                 185                 190

Pro Phe His Phe Pro Glu Lys Leu Ile Pro Leu Thr Ile Leu Asn Ala
        195                 200                 205

Leu Glu Gly Lys Pro Leu Pro Val Tyr Gly Lys Gly Glu Asn Ile Arg
    210                 215                 220

Asp Trp Leu Tyr Val Asp Asp His Ala Lys Ala Leu Ala Thr Ile Ala
225                 230                 235                 240

Thr Thr Gly Lys Val Gly Gln Ser Tyr Asn Val Gly Gly Arg Asn Glu
                245                 250                 255

Arg Thr Asn Leu Gln Val Val Glu Thr Ile Cys Asp Leu Leu Asp Gln
            260                 265                 270

Arg Ile Pro Leu Ala Asp Gly Arg Lys Arg Arg Glu Leu Ile Thr Phe
        275                 280                 285

Val Thr Asp Arg Pro Gly His Asp Arg Arg Tyr Ala Ile Asp Ala Thr
    290                 295                 300

Lys Leu Glu Thr Glu Leu Gly Trp Lys Ala Glu Glu Asn Phe Asp Thr
305                 310                 315                 320

Gly Ile Ala Ala Thr Ile Asp Trp Tyr Leu Ala Asn Glu Trp Trp Trp
                325                 330                 335

Gly Pro Ile Arg Ser Gly Lys Tyr Ala Gly Glu Arg Leu Gly Gln Thr
            340                 345                 350

Ala


<210> SEQ ID NO 42
<211> LENGTH: 867
<212> TYPE: DNA
<213> ORGANISM: Sphingomonas sp. ATCC53159
```

```
<220> FEATURE:
<221> NAME/KEY: CDS
<222> LOCATION: (1)..(867)

<400> SEQUENCE: 42

atg cgt atc ctc gtc acc ggg cat gac ggc cag gtc gcc cag tcg ctg       48
Met Arg Ile Leu Val Thr Gly His Asp Gly Gln Val Ala Gln Ser Leu
1               5                   10                  15

gcc gag cag gcg gtg ggc cac gag ctg gtc ttc acc acc tac ccc gaa       96
Ala Glu Gln Ala Val Gly His Glu Leu Val Phe Thr Thr Tyr Pro Glu
            20                  25                  30

ttc gat ctc tcc aag ccg gag acg atc gag gcc ggt gtg gcg cgg gtg      144
Phe Asp Leu Ser Lys Pro Glu Thr Ile Glu Ala Gly Val Ala Arg Val
        35                  40                  45

cac ccg gac ctg atc gtc tcc gcc gcc gcc tac acg gcg gtc gac aag      192
His Pro Asp Leu Ile Val Ser Ala Ala Ala Tyr Thr Ala Val Asp Lys
    50                  55                  60

gcg gaa agc gaa ccc gag ctg gcg atg gcg atc aac ggc gac ggt ccc      240
Ala Glu Ser Glu Pro Glu Leu Ala Met Ala Ile Asn Gly Asp Gly Pro
65                  70                  75                  80

ggc gtg ctg gcg cgc gcg ggc gcg aag atc ggc gcg ccg atc atc cac      288
Gly Val Leu Ala Arg Ala Gly Ala Lys Ile Gly Ala Pro Ile Ile His
                85                  90                  95

ctg tcg acc gat tat gtg ttc gac ggc agt ctc gac cgc cct tgg cgc      336
Leu Ser Thr Asp Tyr Val Phe Asp Gly Ser Leu Asp Arg Pro Trp Arg
            100                 105                 110

gag gac gat ccc acc ggc ccg ctc ggc gtc tat ggc gcg acc aag ctg      384
Glu Asp Asp Pro Thr Gly Pro Leu Gly Val Tyr Gly Ala Thr Lys Leu
        115                 120                 125

gcc ggc gag cag gcg gtg cag gcc tcg ggt gcc acc aac gcc gtg atc      432
Ala Gly Glu Gln Ala Val Gln Ala Ser Gly Ala Thr Asn Ala Val Ile
    130                 135                 140

cgg ctg gcc tgg gtc tac agc ccg ttc ggc aac aat ttc gtc aag acg      480
Arg Leu Ala Trp Val Tyr Ser Pro Phe Gly Asn Asn Phe Val Lys Thr
145                 150                 155                 160

atg ctc cgc ctc gcc gag acg cgc gac gcg ctg aac gtc gtg gag gac      528
Met Leu Arg Leu Ala Glu Thr Arg Asp Ala Leu Asn Val Val Glu Asp
                165                 170                 175

cag tgg ggc tgc ccc agt tcg gcg ctg gac atc gcg acc gcg atc ctg      576
Gln Trp Gly Cys Pro Ser Ser Ala Leu Asp Ile Ala Thr Ala Ile Leu
            180                 185                 190

acg gtg gtc ggg cac tgg cag cag gac ggc gcg acg agc ggc ctc tac      624
Thr Val Val Gly His Trp Gln Gln Asp Gly Ala Thr Ser Gly Leu Tyr
        195                 200                 205

cat ttc gcc ggc acc ggc gag acc aac tgg gcc gac ttc gca tcg acg      672
His Phe Ala Gly Thr Gly Glu Thr Asn Trp Ala Asp Phe Ala Ser Thr
    210                 215                 220

atc ttc gcc gag agc gcc aag cgc ggt ggc ccc tcg gcc acc gtc acc      720
Ile Phe Ala Glu Ser Ala Lys Arg Gly Gly Pro Ser Ala Thr Val Thr
225                 230                 235                 240

ggc att ccc agc tcg ggc tat ccg act ccg gcc acg cgc ccg gcc aat      768
Gly Ile Pro Ser Ser Gly Tyr Pro Thr Pro Ala Thr Arg Pro Ala Asn
                245                 250                 255

tcg cgg ctg gac tgc acc cgc ttc gcg gag acc ttc ggc tac cgg gcg      816
Ser Arg Leu Asp Cys Thr Arg Phe Ala Glu Thr Phe Gly Tyr Arg Ala
            260                 265                 270

cct gcc tgg cag gat tcg ctg aac gtc gta ctg gat cgc ctg ctc ggc      864
Pro Ala Trp Gln Asp Ser Leu Asn Val Val Leu Asp Arg Leu Leu Gly
        275                 280                 285

tga                                                                  867
```

```
<210> SEQ ID NO 43
<211> LENGTH: 288
<212> TYPE: PRT
<213> ORGANISM: Sphingomonas sp. ATCC53159

<400> SEQUENCE: 43

Met Arg Ile Leu Val Thr Gly His Asp Gly Gln Val Ala Gln Ser Leu
1               5                   10                  15

Ala Glu Gln Ala Val Gly His Glu Leu Val Phe Thr Thr Tyr Pro Glu
            20                  25                  30

Phe Asp Leu Ser Lys Pro Glu Thr Ile Glu Ala Gly Val Ala Arg Val
        35                  40                  45

His Pro Asp Leu Ile Val Ser Ala Ala Ala Tyr Thr Ala Val Asp Lys
    50                  55                  60

Ala Glu Ser Glu Pro Glu Leu Ala Met Ala Ile Asn Gly Asp Gly Pro
65                  70                  75                  80

Gly Val Leu Ala Arg Ala Gly Ala Lys Ile Gly Ala Pro Ile Ile His
                85                  90                  95

Leu Ser Thr Asp Tyr Val Phe Asp Gly Ser Leu Asp Arg Pro Trp Arg
            100                 105                 110

Glu Asp Asp Pro Thr Gly Pro Leu Gly Val Tyr Gly Ala Thr Lys Leu
        115                 120                 125

Ala Gly Glu Gln Ala Val Gln Ala Ser Gly Ala Thr Asn Ala Val Ile
    130                 135                 140

Arg Leu Ala Trp Val Tyr Ser Pro Phe Gly Asn Asn Phe Val Lys Thr
145                 150                 155                 160

Met Leu Arg Leu Ala Glu Thr Arg Asp Ala Leu Asn Val Val Glu Asp
                165                 170                 175

Gln Trp Gly Cys Pro Ser Ser Ala Leu Asp Ile Ala Thr Ala Ile Leu
            180                 185                 190

Thr Val Val Gly His Trp Gln Gln Asp Gly Ala Thr Ser Gly Leu Tyr
        195                 200                 205

His Phe Ala Gly Thr Gly Glu Thr Asn Trp Ala Asp Phe Ala Ser Thr
    210                 215                 220

Ile Phe Ala Glu Ser Ala Lys Arg Gly Gly Pro Ser Ala Thr Val Thr
225                 230                 235                 240

Gly Ile Pro Ser Ser Gly Tyr Pro Thr Pro Ala Thr Arg Pro Ala Asn
                245                 250                 255

Ser Arg Leu Asp Cys Thr Arg Phe Ala Glu Thr Phe Gly Tyr Arg Ala
            260                 265                 270

Pro Ala Trp Gln Asp Ser Leu Asn Val Val Leu Asp Arg Leu Leu Gly
        275                 280                 285


<210> SEQ ID NO 44
<211> LENGTH: 132
<212> TYPE: DNA
<213> ORGANISM: Sphingomonas sp. ATCC53159
<220> FEATURE:
<221> NAME/KEY: CDS
<222> LOCATION: (1)..(132)

<400> SEQUENCE: 44

atc cgg ctg tgc ctg ggg tgc tgg cgg tcg ccc aag gaa atc gcc ggc       48
Ile Arg Leu Cys Leu Gly Cys Trp Arg Ser Pro Lys Glu Ile Ala Gly
1               5                   10                  15

tgg agc gag ctg agt cct aag gga aag cgc gcg gtg cta gag gca ttg       96
```

-continued

```
Trp Ser Glu Leu Ser Pro Lys Gly Lys Arg Ala Val Leu Glu Ala Leu
            20                  25                  30

ccg gcg cgc gaa cgg gag cat ggc ggg ggg cgc tga                  132
Pro Ala Arg Glu Arg Glu His Gly Gly Gly Arg
        35                  40


<210> SEQ ID NO 45
<211> LENGTH: 43
<212> TYPE: PRT
<213> ORGANISM: Sphingomonas sp. ATCC53159

<400> SEQUENCE: 45

Ile Arg Leu Cys Leu Gly Cys Trp Arg Ser Pro Lys Glu Ile Ala Gly
1               5                   10                  15

Trp Ser Glu Leu Ser Pro Lys Gly Lys Arg Ala Val Leu Glu Ala Leu
            20                  25                  30

Pro Ala Arg Glu Arg Glu His Gly Gly Gly Arg
        35                  40
```